US008895003B2

(12) United States Patent
Gaide et al.

(10) Patent No.: US 8,895,003 B2
(45) **Date of Patent: *Nov. 25, 2014**

(54) PHARMACEUTICAL COMPOSITION COMPRISING EDA-1 FUSION PROTEIN

(71) Applicant: Topotarget Switzerland SA, Lausanne (CH)

(72) Inventors: Olivier Gaide, Geneva (CH); Pascal Schneider, Epalinges (CH); Jurg Tschopp, Epalinges (CH)

(73) Assignee: Topotarget Switzerland SA, Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/922,897

(22) Filed: Jun. 20, 2013

(65) Prior Publication Data

US 2013/0295093 A1 Nov. 7, 2013

Related U.S. Application Data

(63) Continuation of application No. 12/756,268, filed on Apr. 8, 2010, now Pat. No. 8,501,177, which is a continuation of application No. 10/503,999, filed as application No. PCT/EP02/09354 on Aug. 21, 2002, now Pat. No. 7,736,657.

(30) Foreign Application Priority Data

Feb. 10, 2002 (DE) .................................. 102 05 368
Feb. 11, 2002 (DE) .................................. 102 05 583

(51) Int. Cl.
*A61K 39/395* (2006.01)
*C07K 14/705* (2006.01)
*A61K 38/00* (2006.01)

(52) U.S. Cl.
CPC ....... *A61K 39/3955* (2013.01); *C07K 14/70578* (2013.01); *C07K 2319/30* (2013.01); *A61K 38/00* (2013.01)
USPC .................................... 424/134.1; 530/387.3

(58) Field of Classification Search
CPC .............. A61K 38/00; A61K 39/3955; A61K 2039/505; A61K 51/088; A61K 38/212; A61K 51/08; A61K 47/48423; A61K 49/16; A61K 38/191; A61K 38/217; A61K 51/10; C07K 2319/00; C07K 14/7151; C07K 2319/30; C07K 14/70578; C07K 16/2878; C07K 14/52; C07K 14/525; C07K 14/555; A01K 2217/05; A01K 2217/056; A01K 2207/15; A01K 2217/075; A01K 2227/105; A01K 2267/0318; A01K 67/0276
USPC ............. 424/1.53, 85.2, 133.1, 134.1, 178.1; 435/69.7; 530/387.3; 514/1.1
See application file for complete search history.

(56) References Cited

U.S. PATENT DOCUMENTS

| | | | |
|---|---|---|---|
| 6,046,310 A | 4/2000 | Queen et al. |
| 6,316,256 B1 | 11/2001 | Tykocinski et al. |
| 6,617,135 B1 | 9/2003 | Gillies et al. |
| 7,115,555 B2 | 10/2006 | Zonana et al. |
| 7,385,032 B2 | 6/2008 | Tschopp et al. |

FOREIGN PATENT DOCUMENTS

| | | |
|---|---|---|
| WO | 94/04678 A1 | 3/1994 |
| WO | 00/63253 A1 | 10/2000 |
| WO | 01/49866 | 7/2001 |
| WO | 01/24811 A1 | 3/2002 |

OTHER PUBLICATIONS

Tsutsumi et al. Chemical modification of natural human tumor necrosis factor-alpha with polyethylene glycol increases its anti-tumor potency. Jpn J Cancer Res. Jan. 1994;85(1):9-12.*
Baum Peter R. et al., EMBO Journal, vol. 13, No. 17, 3992-4001, 1994.
Bodmer et al., Trends in Biochemical Sciences, vol. 27, No. 1. 19-26, 2002.
Bulfone-Paus et al., Transplantation, vol. 69, No. 7, 1386-1391, 2000.
Definition of "hexamer", http://www.biology-online.org/dictionary/Hexamer, retrieved onJun. 8, 2009.
Fanslow et al., Seminars in Immunology, vol. 6, No. 5, 267-278, 1994.
Gaide, Am J Med Genet Part A, 149A:2042-2044 (2009). "Gene Therapy and Protein Therapy of Ectodermal Dysplasias: A Perspective."
Holler et al., Journal of Immunological Methods, vol. 237, No. 1-2, 159-173, 2000.
Holler et al., Molecular and Cellular Biology, vol. 23, No. 4, 1428-1440, 2003.
Kondo et al., Curr. Biol. 11(15):1202-1206, 2001.
Mohler et al., Journal of Immunology, 151(3):1548-1561 (1993). "Soluble Tumor Necrosis Factor (TNF) Receptors Are Effective Therapeutic Agents in Lethal Endotoxemia and Function Simultaneously as Both TNF Carriers and TNF Antagonists."
Peppel et al., J. Exp. Med., 174(6):1483-9, 1991.
Smahi et al., Human Molecular Genetics, 11(20):2371-2375 (2002). "The NF-κb signalling pathway in human diseases: from incontinentia pigmenti to ectodermal dysplasias and immune-deficiency syndromes."
Schneider et al., Pharmaceutica Acta Helvetiae, vol. 74, No. 2/3, 281-286, 2000.
Schneider et al., J. Biol. Chem. 276(22):18819-27, 2001.

* cited by examiner

*Primary Examiner* — Gregory S Emch
(74) *Attorney, Agent, or Firm* — Donna T. Ward; Lingyun Jia; DT Ward P.C.

(57) ABSTRACT

Disclosed is a recombinant fusion protein containing an amino-acid sequence which comprises: (a) the Fc section or part of an Fc section of an immunoglobulin as component (A) or a functional variant of component (A); (b) the extracellular part of a TNF ligand or a partial sequence of the extracellular part of a TNF ligand as component (B) or a functional variant of component (B); and optionally (c) a transition area between component (A) and component (B), containing a linker.

15 Claims, 24 Drawing Sheets

FIG. 1A
COOH PORTION OF ANY TNF FAMILY LIGAND
PROTEASE SITE
LINKER
Fc PORTION OF tgG
SIGNAL PEPTIDE

PS1158 Fc-PS:FasL

HA SIGNAL

Figure 1A:
Figure 1C:
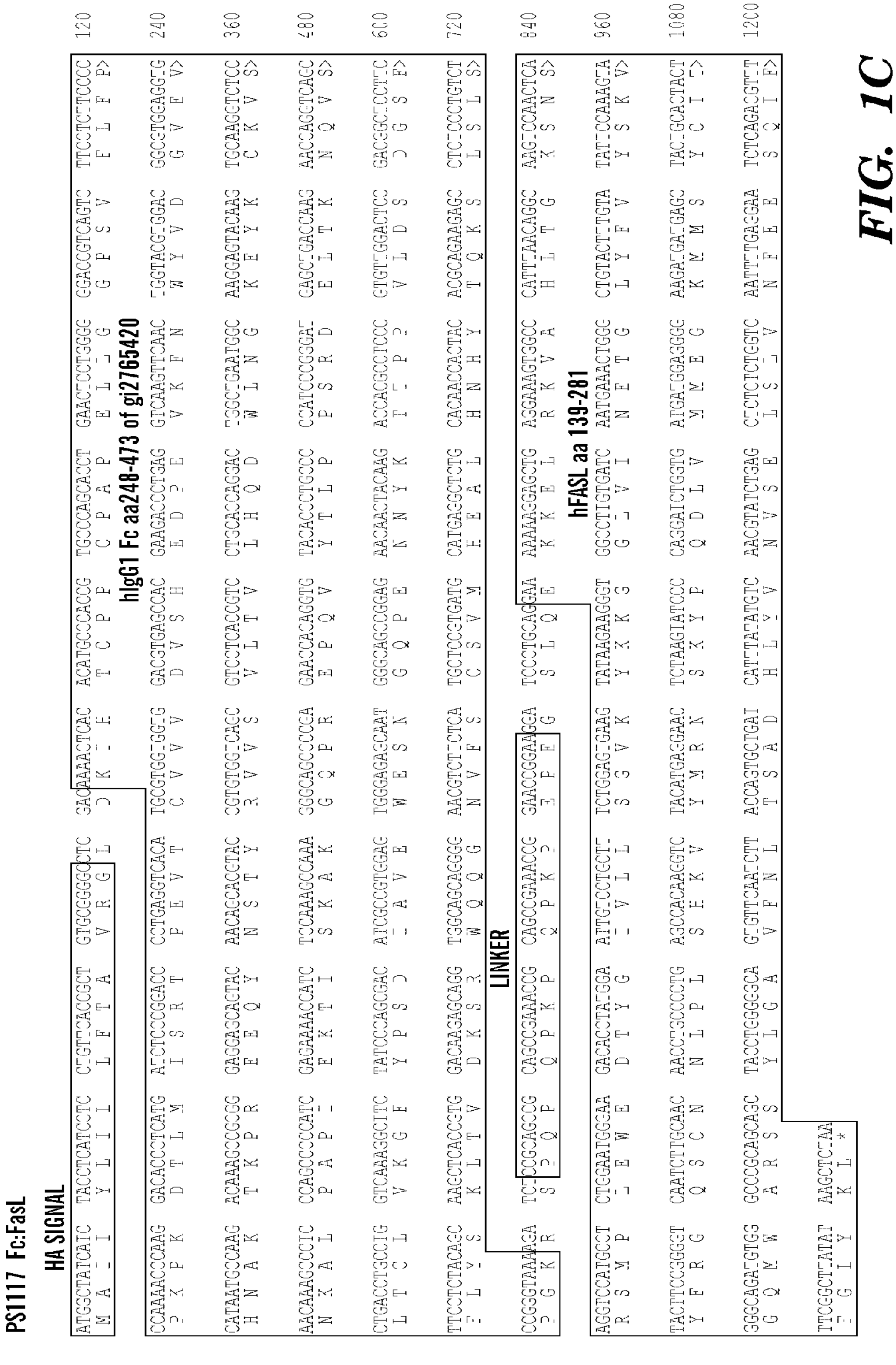
Figure 1G:
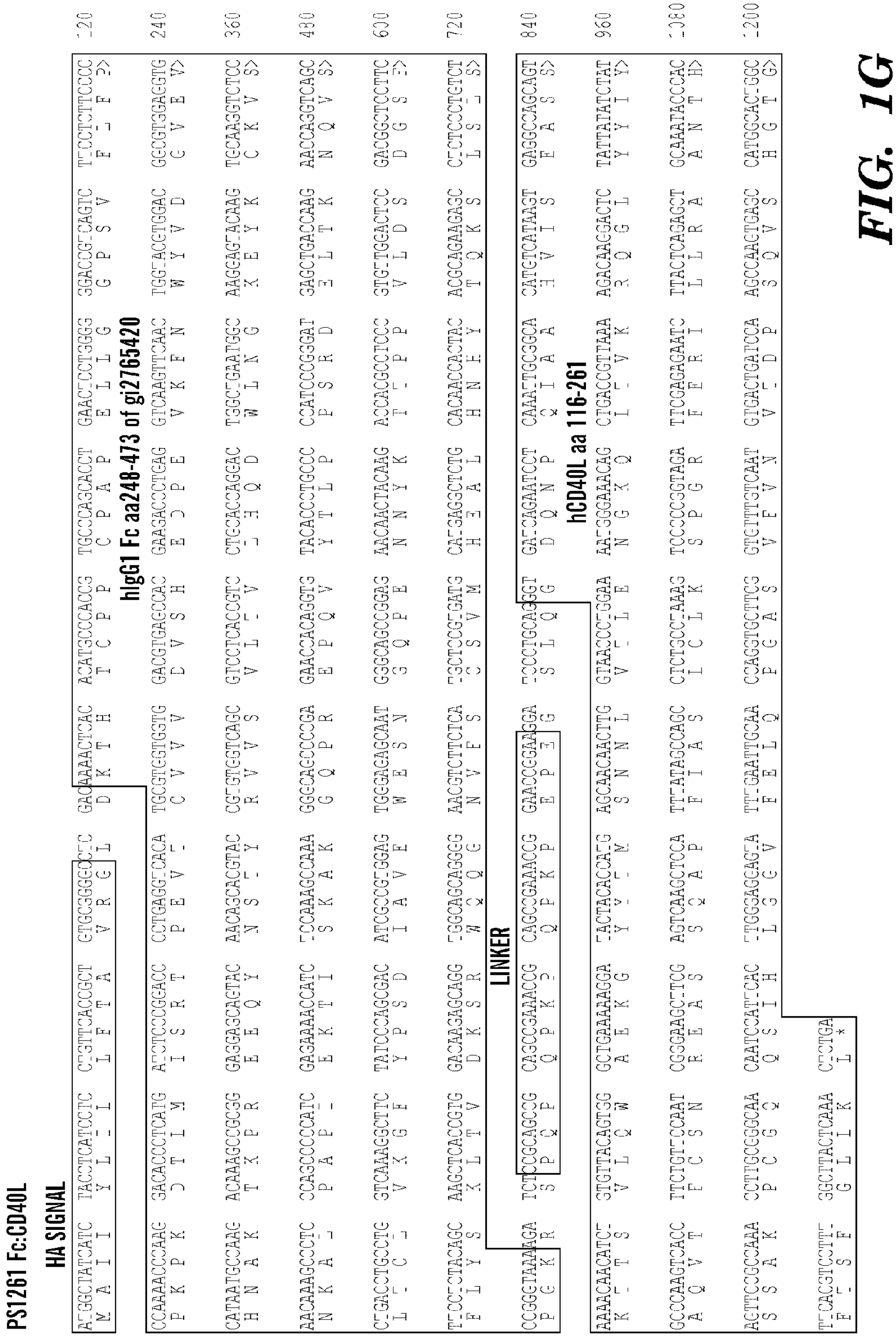
Figure 1H:
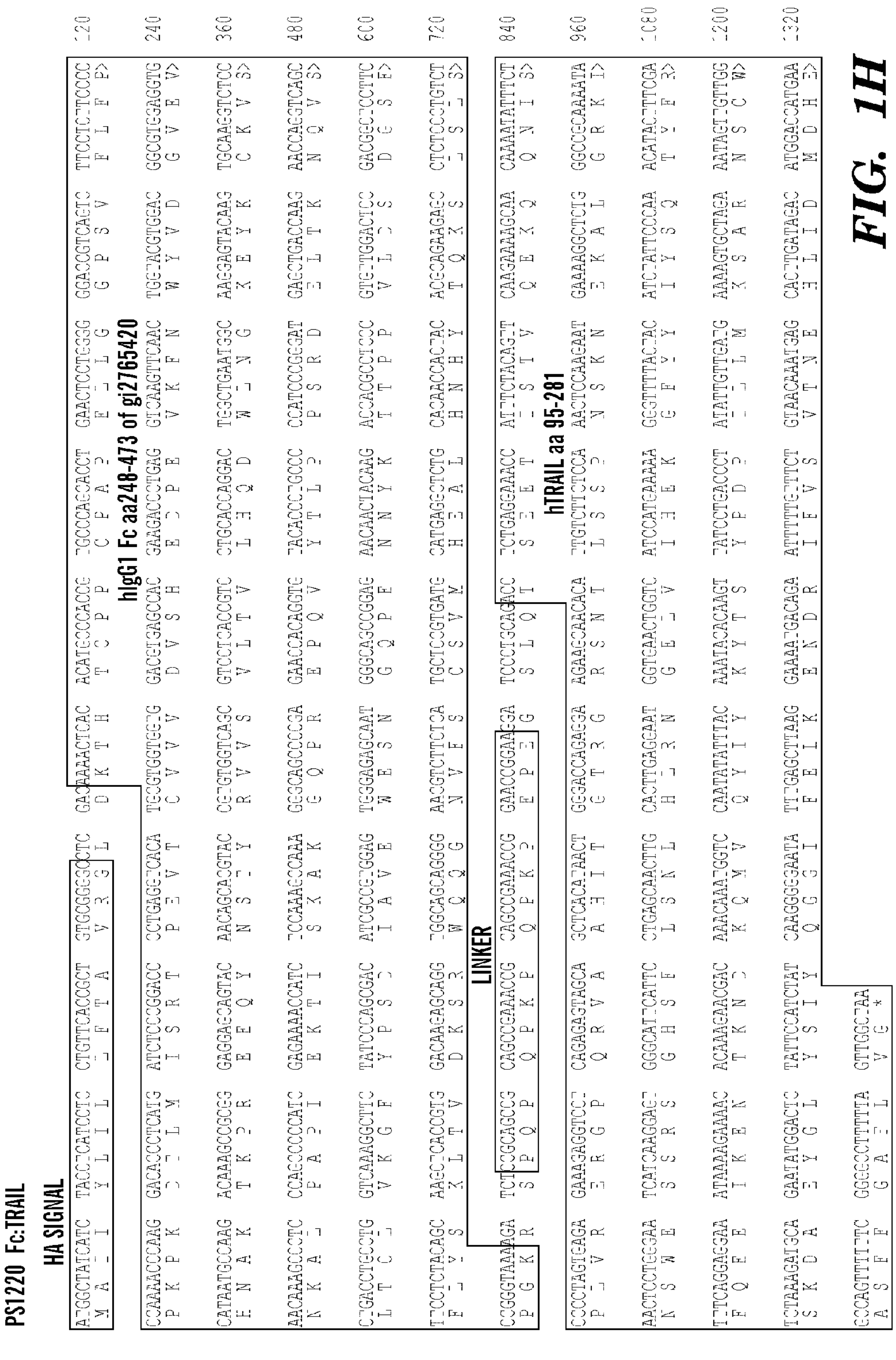

```
ATGGCTATCATC TACCTCATCCTC CTGTTCACCGCT GTGCGGGGCCTC GACAAAACTCAC ACATGCCCACCG TGCCCAGCACCT GAACTCCTGGGG GGACCGTCAGTC TTCCTCTTCCCC  120
 M  A  I  I   Y  L  I  L   L  F  T  A   V  R  G  L   D  K  T  H   T  C  P  P   C  P  A  P   E  L  L  G   G  P  S  V   F  L  F  P>
```

hIgG1 Fc aa248-473 of gi2765420

```
CCAAAACCCAAG GACACCCTCATG ATCTCCCGGACC CCTGAGGTCACA TGCGTGGTGGTG GACGTGAGCCAC GAAGACCCTGAG GTCAAGTTCAAC TGGTACGTGGAC GGCGTGGAGGTG  240
 P  K  P  K   D  T  L  M   I  S  R  T   P  E  V  T   C  V  V  V   D  V  S  H   E  D  P  E   V  K  F  N   W  Y  V  D   G  V  E  V>

CATAATGCCAAG ACAAAGCCGCGG GAGGAGCAGTAC AACAGCACGTAC CGTGTGGTCAGC GTCCTCACCGTC CTGCACCAGGAC TGGCTGAATGGC AAGGAGTACAAG TGCAAGGTCTCC  360
 H  N  A  K   T  K  P  R   E  E  Q  Y   N  S  T  Y   R  V  V  S   V  L  T  V   L  H  Q  D   W  L  N  G   K  E  Y  K   C  K  V  S>

AACAAAGCCCTC CCAGCCCCCATC GAGAAAACCATC TCCAAAGCCAAA GGGCAGCCCCGA GAACCACAGGTG TACACCCTGCCC CCATCCCGGGAT GAGCTGACCAAG AACCAGGTCAGC  480
 N  K  A  L   P  A  P  I   E  K  T  I   S  K  A  K   G  Q  P  R   E  P  Q  V   Y  T  L  P   P  S  R  D   E  L  T  K   N  Q  V  S>

CTGACCTGCCTG GTCAAAGGCTTC TATCCCAGCGAC ATCGCCGTGGAG TGGGAGAGCAAT GGGCAGCCGGAG AACAACTACAAG ACCACGCCTCCC GTGTTGGACTCC GACGGCTCCTTC  600
 L  T  C  L   V  K  G  F   Y  P  S  D   I  A  V  E   W  E  S  N   G  Q  P  E   N  N  Y  K   T  T  P  P   V  L  D  S   D  G  S  F>

TTCCTCTACAGC AAGCTCACCGTG GACAAGAGCAGG TGGCAGCAGGGG AACGTCTTCTCA TGCTCCGTGATG CATGAGGCTCTG CACAACCACTAC ACGCAGAAGAGC CTCTCCCTGTCT  720
 F  L  Y  S   K  L  T  V   D  K  S  R   W  Q  Q  G   N  V  F  S   C  S  V  M   H  E  A  L   H  N  H  Y   T  Q  K  S   L  S  L  S>
```

LINKER

PRESCISSION

```
CCGGGTAAAAGA TCTCCGCAGCCG CAGCCGAAACCG CAGCCGAAACCG GAACCGGAAGGA TCTCTGGAGGTG CTGTTCCAGGGG CCCGGATCCCTG CAGGAAAAAAAG GAGCTGAGGAAA  840
 P  G  K  R   S  P  Q  P   Q  P  K  P   Q  P  K  P   E  P  E  G   S  L  E  V   L  F  Q  G   P  G  S  L   Q  E  K  K   E  L  R  K>

GTGGCCCATTTA ACAGGCAAGTCC AACTCAAGGTCC ATGCCTCTGGAA TGGGAAGACACC TATGGAATTGTC CTGCTTTCTGGA GTGAAGTATAAG AAGGGTGGCCTT GTGATCAATGAA  960
 V  A  H  L   T  G  K  S   N  S  R  S   M  P  L  E   W  E  D  T   Y  G  I  V   L  L  S  G   V  K  Y  K   K  G  G  L   V  I  N  E>
```

hFASL aa 139-281

```
ACTGGGCTGTAC TTTGTATATTCC AAAGTATACTTC CGGGGTCAATCT TGCAACAACCTG CCCCTGAGCCAC AAGGTCTACATG AGGAACTCTAAG TATCCCCAGGAT CTGGTGATGATG  1080
 T  G  L  Y   F  V  Y  S   K  V  Y  F   R  G  Q  S   C  N  N  L   P  L  S  H   K  V  Y  M   R  N  S  K   Y  P  Q  D   L  V  M  M>

GAGGGGAAGATG ATGAGCTACTGC ACTACTGGGCAG ATGTGGGCCCGC AGCAGCTACCTG GGGGCAGTGTTC AATCTTACCAGT GCTGATCATTTA TATGTCAACGTA TCTGAGCTCTCT  1200
 E  G  K  M   M  S  Y  C   T  T  G  Q   M  W  A  R   S  S  Y  L   G  A  V  F   N  L  T  S   A  D  H  L   Y  V  N  V   S  E  L  S>

CTGGTCAATTTT GAGGAATCTCAG ACGTTTTTCGGC TTATATAAGCTC TAA
 L  V  N  F   E  E  S  Q   T  F  F  G   L  Y  K  L   *
```

*FIG. 1B*

PS1236 Fc:EDA1

HA SIGNAL hIgG1 Fc aa248-473 of gi2765420

LINKER hEDA1 aa 245-391

```
ATGGCTATCATC TACCTCATCCTC CTGTTCACCGCT GTGCGGGGCCTC GACAAAACTCAC ACATGCCCACCG TGCCCAGCACCT GAACTCCTGGGG GGACCGTCAGTC TTCCTCTTCCCC 120
 M  A  I  I   Y  L  I  L   L  F  T  A   V  R  G  L   D  K  T  H   T  C  P  P   C  P  A  P   E  L  L  G   G  P  S  V   F  L  F  P>

CCAAAACCCAAG GACACCCTCATG ATCTCCCGGACC CCTGAGGTCACA TGCGTGGTGGTG GACGTGAGCCAC GAAGACCCTGAG GTCAAGTTCAAC TGGTACGTGGAC GGCGTGGAGGTG 240
 P  K  P  K   D  T  L  M   I  S  R  T   P  E  V  T   C  V  V  V   D  V  S  H   E  D  P  E   V  K  F  N   W  Y  V  D   G  V  E  V>

CATAATGCCAAG ACAAAGCCGCGG GAGGAGCAGTAC AACAGCACGTAC CGTGTGGTCAGC GTCCTCACCGTC CTGCACCAGGAC TGGCTGAATGGC AAGGAGTACAAG TGCAAGGTCTCC 360
 H  N  A  K   T  K  P  R   E  E  Q  Y   N  S  T  Y   R  V  V  S   V  L  T  V   L  H  Q  D   W  L  N  G   K  E  Y  K   C  K  V  S>

AACAAAGCCCTC CCAGCCCCCATC GAGAAAACCATC TCCAAAGCCAAA GGGCAGCCCCGA GAACCACAGGTG TACACCCTGCCC CCATCCCGGGAT GAGCTGACCAAG AACCAGGTCAGC 480
 N  K  A  L   P  A  P  I   E  K  T  I   S  K  A  K   G  Q  P  R   E  P  Q  V   Y  T  L  P   P  S  R  D   E  L  T  K   N  Q  V  S>

CTGACCTGCCTG GTCAAAGGCTTC TATCCCAGCGAC ATCGCCGTGGAG TGGGAGAGCAAT GGGCAGCCGGAG AACAACTACAAG ACCACGCCTCCC GTGTTGGACTCC GACGGCTCCTTC 600
 L  T  C  L   V  K  G  F   Y  P  S  D   I  A  V  E   W  E  S  N   G  Q  P  E   N  N  Y  K   T  T  P  P   V  L  D  S   D  G  S  F>

TTCCTCTACAGC AAGCTCACCGTG GACAAGAGCAGG TGGCAGCAGGGG AACGTCTTCTCA TGCTCCGTGATG CATGAGGCTCTG CACAACCACTAC ACGCAGAAGAGC CTCTCCCTGTCT 720
 F  L  Y  S   K  L  T  V   D  K  S  R   W  Q  Q  G   N  V  F  S   C  S  V  M   H  E  A  L   H  N  H  Y   T  Q  K  S   L  S  L  S>

CCGGGTAAAAGA TCTCCGCAGCCG CAGCCGAAACCG CAGCCGAAACCG GAACCGGAAGGA TCCCTGCAGGTC GACGAAAATCAG CCAGCTGTGGTG CATCTGCAGGGC CAAGGGTCAGCA 840
 P  G  K  R   S  P  Q  P   Q  P  K  P   Q  P  K  P   E  P  E  G   S  L  Q  V   D  E  N  Q   P  A  V  V   H  L  Q  G   Q  G  S  A>

ATTCAAGTCAAA AATGATCTTTCA GGTGGACTGCTC AATGACTGGTCT CGCATCACTATG AACCCTAAGGTG TTTAAACTACAT CCCCGCAGCGGG GAGCTGGAGGTA CTGGTGGACGGC 960
 I  Q  V  K   N  D  L  S   G  G  V  L   N  D  W  S   R  I  T  M   N  P  K  V   F  K  L  H   P  R  S  G   E  L  E  V   L  V  D  G>

ACCTACTTCATC TATAGTCAGGTA GAAGTCTACTAC ATCAACTTCACT GACTTTGCCAGC TACGAGGTGGTG GTGGATGAGAAG CCCTTCCTGCAG TGCACCCGCAGC ATTGAGACAGGG 1080
 T  Y  F  I   Y  S  Q  V   E  V  Y  Y   I  N  F  T   D  F  A  S   Y  E  V  V   V  D  E  K   P  F  L  Q   C  T  R  S   I  E  T  G>

AAGACCAACTAC AACACTTGCTAT ACTGCAGGCGTG TGCCTCCTCAAG GCCAGGCAGAAA ATCGCCGTGAAG ATGGTGCACGCT GACATCTCTATC AATATGAGCAAG CACACCACCTTC 1200
 K  T  N  Y   N  T  C  Y   T  A  G  V   C  L  L  K   A  R  Q  K   I  A  V  K   M  V  H  A   D  I  S  I   N  M  S  K   H  T  T  F>

TTCGGGGCCATC AGGCTGGGCGAA GCCCCTGCATCC TAG
 F  G  A  I   R  L  G  E   A  P  A  S   *
```

*FIG. 1D*

PS1235 Fc:EDA2

HA SIGNAL hIgG1 Fc aa248-473 of gi2765420

LINKER hEDA2 aa 245-389

```
ATGGCTATCATC TACCTCATCCTC CTGTTCACCGCT GTGCGGGGCCTC GACAAAACTCAC ACATGCCCACCG TGCCCAGCACCT GAACTCCTGGGG GGACCGTCAGTC TTCCTCTTCCCC 120
 M  A  I  I   Y  L  I  L   L  F  T  A   V  R  G  L   D  K  T  H   T  C  P  P   C  P  A  P   E  L  L  G   G  P  S  V   F  L  F  P>

CCAAAACCCAAG GACACCCTCATG ATCTCCCGGACC CCTGAGGTCACA TGCGTGGTGGTG GACGTGAGCCAC GAAGACCCTGAG GTCAAGTTCAAC TGGTACGTGGAC GGCGTGGAGGTG 240
 P  K  P  K   D  T  L  M   I  S  R  T   P  E  V  T   C  V  V  V   D  V  S  H   E  D  P  E   V  K  F  N   W  Y  V  D   G  V  E  V>

CATAATGCCAAG ACAAAGCCGCGG GAGGAGCAGTAC AACAGCACGTAC CGTGTGGTCAGC GTCCTCACCGTC CTGCACCAGGAC TGGCTGAATGGC AAGGAGTACAAG TGCAAGGTCTCC 360
 H  N  A  K   T  K  P  R   E  E  Q  Y   N  S  T  Y   R  V  V  S   V  L  T  V   L  H  Q  D   W  L  N  G   K  E  Y  K   C  K  V  S>

AACAAAGCCCTC CCAGCCCCCATC GAGAAAACCATC TCCAAAGCCAAA GGGCAGCCCCGA GAACCACAGGTG TACACCCTGCCC CCATCCCGGGAT GAGCTGACCAAG AACCAGGTCAGC 480
 N  K  A  L   P  A  P  I   E  K  T  I   S  K  A  K   G  Q  P  R   E  P  Q  V   Y  T  L  P   P  S  R  D   E  L  T  K   N  Q  V  S>

CTGACCTGCCTG GTCAAAGGCTTC TATCCCAGCGAC ATCGCCGTGGAG TGGGAGAGCAAT GGGCAGCCGGAG AACAACTACAAG ACCACGCCTCCC GTGTTGGACTCC GACGGCTCCTTC 600
 L  T  C  L   V  K  G  F   Y  P  S  D   I  A  V  E   W  E  S  N   G  Q  P  E   N  N  Y  K   T  T  P  P   V  L  D  S   D  G  S  F>

TTCCTCTACAGC AAGCTCACCGTG GACAAGAGCAGG TGGCAGCAGGGG AACGTCTTCTCA TGCTCCGTGATG CATGAGGCTCTG CACAACCACTAC ACGCAGAAGAGC CTCTCCCTGTCT 720
 F  L  Y  S   K  L  T  V   D  K  S  R   W  Q  Q  G   N  V  F  S   C  S  V  M   H  E  A  L   H  N  H  Y   T  Q  K  S   L  S  L  S>

CCGGGTAAAAGA TCTCCGCAGCCG CAGCCGAAACCG CAGCCGAAACCG GAACCGGAAGGA TCCCTGCAGGTC GACGAAAATCAG CCAGCTGTGGTG CATCTGCAGGGC CAAGGCTCAGCA 840
 P  G  K  R   S  P  Q  P   Q  P  K  P   Q  P  K  P   E  P  E  G   S  L  Q  V   D  E  N  Q   P  A  V  V   H  L  Q  G   Q  G  S  A>

ATTCAAGTCAAA AATGATCTTTCA GGTGGAGTGCTC AATGACTGGTCT CGCATCACTATG AACCCTAAGGTG TTTAAACTACAT CCCCGCAGCGGG GAGCTGGAGGTA CTGGTGGACGGC 960
 I  Q  V  K   N  D  L  S   G  G  V  L   N  D  W  S   R  I  T  M   N  P  K  V   F  K  L  H   P  R  S  G   E  L  E  V   L  V  D  G>

ACCTACTTCATC TATAGTCAGGTA TACTACATCAAC TTCACTGACTTT GCCAGCTACGAG GTGGTGGTGGAT GAGAAGCCCTTC CTGCAGTGCACC CGCAGCATTGAG ACAGGGAAGACC 1080
 T  Y  F  I   Y  S  Q  V   Y  Y  I  N   F  T  D  F   A  S  Y  E   V  V  V  D   E  K  P  F   L  Q  C  T   R  S  I  E   T  G  K  T>

AACTACAACACT TGCTATACTGCA GGCGTGTGCCTC CTCAAGGCCAGG CAGAAAATCGCC GTGAAGATGGTG CACGCTGACATC TCTATCAATATG AGCAAGCACACC ACCTTCTTCGGC 1200
 N  Y  N  T   C  Y  T  A   G  V  C  L   L  K  A  R   Q  K  I  A   V  K  M  V   H  A  D  I   S  I  N  M   S  K  H  T   T  F  F  G>

GCCATCAGGCTG GGCGAAGCCCCT GCATCCTAG
 A  I  R  L   G  E  A  P   A  S  *
```

*FIG. 1E*

PS1181 Fc:TNFα

HA SIGNAL hIgG1 Fc aa248-473 of gi2765420

LINKER hTNFα aa 80-228

```
ATGGCTATCATC TACCTCATCCTC CTGTTCACCGCT GTGCGGGGCCTC GACAAAACTCAC ACATGCCCACCG TGCCCAGCACCT GAACTCCTGGGG GGACCGTCAGTC TTCCTCTTCCCC 120
 M  A  I  I   Y  L  I  L   L  F  T  A   V  R  G  L   D  K  T  H   T  C  P  P   C  P  A  P   E  L  L  G   G  P  S  V   F  L  F  P>

CCAAAACCCAAG GACACCCTCATG ATCTCCCGGACC CCTGAGGTCACA TGCGTGGTGGTG GACGTGAGCCAC GAAGACCCTGAG GTCAAGTTCAAC TGGTACGTGGAC GGCGTGGAGGTG 240
 P  K  P  K   D  T  L  M   I  S  R  T   P  E  V  T   C  V  V  V   D  V  S  H   E  D  P  E   V  K  F  N   W  Y  V  D   G  V  E  V>

CATAATGCCAAG ACAAAGCCGCGG GAGGAGCAGTAC AACAGCACGTAC CGTGTGGTCAGC GTCCTCACCGTC CTGCACCAGGAC TGGCTGAATGGC AAGGAGTACAAG TGCAAGGTCTCC 360
 H  N  A  K   T  K  P  R   E  E  Q  Y   N  S  T  Y   R  V  V  S   V  L  T  V   L  H  Q  D   W  L  N  G   K  E  Y  K   C  K  V  S>

AACAAAGCCCTC CCAGCCCCCATC GAGAAAACCATC TCCAAAGCCAAA GGGCAGCCCCGA GAACCACAGGTG TACACCCTGCCC CCATCCCGGGAT GAGCTGACCAAG AACCAGGTCAGC 480
 N  K  A  L   P  A  P  I   E  K  T  I   S  K  A  K   G  Q  P  R   E  P  Q  V   Y  T  L  P   P  S  R  D   E  L  T  K   N  Q  V  S>

CTGACCTGCCTG GTCAAAGGCTTC TATCCCAGCGAC ATCGCCGTGGAG TGGGAGAGCAAT GGGCAGCCGGAG AACAACTACAAG ACCACGCCTCCC GTGTTGGACTCC GACGGCTCCTTC 600
 L  T  C  L   V  K  G  F   Y  P  S  D   I  A  V  E   W  E  S  N   G  Q  P  E   N  N  Y  K   T  T  P  P   V  L  D  S   D  G  S  F>

TTCCTCTACAGC AAGCTCACCGTG GACAAGAGCAGG TGGCAGCAGGGG AACGTCTTCTCA TGCTCCGTGATG CATGAGGCTCTG CACAACCACTAC ACGCAGAAGAGC CTCTCCCTGTCT 720
 F  L  Y  S   K  L  T  V   D  K  S  R   W  Q  Q  G   N  V  F  S   C  S  V  M   H  E  A  L   H  N  H  Y   T  Q  K  S   L  S  L  S>

CCGGGTAAAAGA TCTCCGCAGCCG CAGCCGAAACCG CAGCCGAAACCG GAACCGGAAGGA TCCCTGCAGAGT GACAAGCCTGTA GCCCATGTTGTA GCAAACCCTCAA GCTGAGGGGCAG 840
 P  G  K  R   S  P  Q  P   Q  P  K  P   Q  P  K  P   E  P  E  G   S  L  Q  S   D  K  P  V   A  H  V  V   A  N  P  Q   A  E  G  Q>

CTCCAGTGGCTG AACCGCCGGGCC AATGCCCTCCTG GCCAATGGCGTG GAGCTGAGAGAT AACCAGCTGGTG GTGCCATCAGAG GGCCTGTACCTC ATCTACTCCCAG GTCCTCTTCAAG 960
 L  Q  W  L   N  R  R  A   N  A  L  L   A  N  G  V   E  L  R  D   N  Q  L  V   V  P  S  E   G  L  Y  L   I  Y  S  Q   V  L  F  K>

GGCCAAGGCTGC CCCTCCACCCAT GTGCTCCTCACC CACACCATCAGC CGCATCGCCGTC TCCTACCAGACC AAGGTCAACCTC CTCTCTGCCATC AAGAGCCCCTGC CAGAGGGAGACC 1080
 G  Q  G  C   P  S  T  H   V  L  L  T   H  T  I  S   R  I  A  V   S  Y  Q  T   K  V  N  L   L  S  A  I   K  S  P  C   Q  R  E  T>

CCAGAGGGGGCT GAGGCCAAGCCC TGGTATGAGCCC ATCTATCTGGGA GGGGTCTTCCAG CTGGAGAAGGGT GACCGACTCAGC GCTGAGATCAAT CGGCCCGACTAT CTCGACTTTGCC 1200
 P  E  G  A   E  A  K  P   W  Y  E  P   I  Y  L  G   G  V  F  Q   L  E  K  G   D  R  L  S   A  E  I  N   R  P  D  Y   L  D  F  A>

GAGTCTGGGCAG GTCTACTTTGGG ATCATTGCCCTG TGA
 E  S  G  Q   V  Y  F  G   I  I  A  L   *
```

FIG. 1F

PS1196 Fc-PS:BAFF

HA SIGNAL

```
ATGGCTATCATC TACCTCATCCTC CTGTTCACGGCT GTGTCGGGGCTC                                                                                                              
 M  A  I  I    Y  L  I  L     L  F  T  A    V  S  G  L

CCAAAACCCAAG GACACCCTCATG ATCTCCCGGACC CCTAGTCAGACA CAGCCTGAGTCAG GAACAGCAGGAC AGATGCCCACCGT GCCCAGCACCT GAACTCCTGGGG GGACCGTCAGTC    120
 P  K  P  K    D  T  L  M     I  S  R  T    P  E  V  T   C  V  V  V  D         V  S  H  E     D  P  E     A  P  E  L  L  G         G  P  S  V
                                                                         hIgG1 Fc aa248-473 of gi2765420                         F  L  F  P

CATAAGGCCAAG ACAAAGCCGCGG GAGGAGCAGTAC AACAGCACGTAC CGTGTGGTCAGC GTCCTCACCGTC CTGCACCAGGAC TGGCTGAATGGC AAGGAGTACAAG TGCAAGGTCTCC    240
 H  K  A  K    T  K  P  R     E  E  Q  Y    N  S  T  Y   R  V  V  S         V  L  T  V      L  H  Q  D    W  L  N  G    K  E  Y  K    C  K  V  S

AACAAAGCCCTC CCAGCCCCCATC GAGAAAACCATC TCCAAAGCCAAA GGGCAGCCCCGA GAACCACAGGTG TACACCCTGCCC CCATCCCGGGAT GAGCTGACCAAG AACCAGGTCAGC    360
 N  K  A  L    P  A  P  I     E  K  T  I    S  K  A  K   G  Q  P  R         E  P  Q  V     Y  T  L  P     P  S  R  D    E  L  T  K    N  Q  V  S

CTGACCTGCCTG GTCAAAGGCTTC TATCCCAGCGAC ATCGCCGTGGAG TGGGAGAGCAAT GGGCAGCCGGAG AACAACTACAAG ACCACGCCTCCC GTGCTGGACTCC GACGGCTCCTTC    480
 L  T  C  L    V  K  G  F     Y  P  S  D    I  A  V  E   W  E  S  N         G  Q  P  E     N  N  Y  K     T  T  P  P    V  L  D  S    D  G  S  F

TTCCTCTACAGC AAGCTCACCGTG GACAAGAGCAGG TGGCAGCAGGGG AACGTCTTCTCA TGCTCCGTGATG CATGAGGCTCTG CACAACCACTAC ACGCAGAAGAGC CTCTCCCTGTCT    600
 F  L  Y  S    K  L  T  V     D  K  S  R    W  Q  Q  G   N  V  F  S         C  S  V  M     H  E  A  L     H  N  H  Y    T  Q  K  S    L  S  L  S

### LINKER

CCGGGTAAAAGA CAGCCGAAACCG CAGCCGAAACCG CAGCCGAAACCG TCTCTGGAGGTG CTGTTCCAGGGG CCCGGATCCCTG GAAACAGCTACT    720
 P  G  K  R    Q  P  K  P     Q  P  K  P    Q  P  K  P   S  L  E  V         L  F  Q  G     P  G  S  L     E  T  V  T

### PRESCISSION

### hBAFF aa 137-285

CAAGACTGTTTG CAACTGATTGCA GACAGTGAAACA CCAACTATACAA AAAGGATCTTAC ACATTTGTTCCA TGGCTTCTCAGC TTTAAAAGGGGA AGTCCCCTAGAA GAAAAGACAAAT    840
 Q  D  C  L    Q  L  I  A     D  S  E  T    P  T  I  Q   K  G  S  Y         T  F  V  P     W  L  L  S     F  K  R  G    S  P  L  E    E  K  E  N

AAAATATTGGTC AAAGAAACTGGT TACTTTTTTATA TATGGTCAGGTT CTTTATACTGAT AAGACATTTGCC ATGGGACATCTA ATTCAGAGGAAG AAGGTCCATGTC TTTGGGGATGAA    960
 K  I  L  V    K  E  T  G     Y  F  F  I    Y  G  Q  V   L  Y  T  D         K  T  F  A     M  G  H  L     I  Q  R  K    K  V  H  V    F  G  D  E

TTGAGCCTGGTG ACTTTGTTTCGT TGTATTCAAAAT ATGCCTGAAACA CTACCCAATAAT TCCTGCTATTCA GCTGGCATTGCA AAACTGGAAGAA GGAGATGAACTC TTTGGGGAAATC    1080
 L  S  L  V    T  L  F  R     C  I  Q  N    M  P  E  T   L  P  N  N         S  C  Y  S     A  G  I  A     K  L  E  E    G  D  E  L    F  G  D  E

CCAAGAGAAAAT GCACAAATATCA CTGGATGGAGAT GTCACATTTTTT GGTGCATTGAAA CTGCTGTGA    1200
 P  R  E  N    A  Q  I  S     L  D  G  D    V  T  F  F   G  A  L  K         L  L  *
```

FIG. 1J

PS1307 Fc-PS:APRIL

HA SIGNAL hIgG1 Fc aa248-473 of gi2765420

LINKER

PRESCISSION hAPRIL aa 98-233

```
ATGGCTATCATC TACCTCATCCTC CTGTTCACCGCT GTGCGGGGCCTC GACAAAACTCAC ACATGCCCACCG TGCCCAGCACCT GAACTCCTGGGG GGACCGTCAGTC TTCCTCTTCCCC 120
 M  A  I  I   Y  L  I  L   L  F  T  A   V  R  G  L   D  K  T  H   T  C  P  P   C  P  A  P   E  L  L  G   G  P  S  V   F  L  F  P>

CCAAAACCCAAG GACACCCTCATG ATCTCCCGGACC CCTGAGGTCACA TGCGTGGTGGTG GACGTGAGCCAC GAAGACCCTGAG GTCAAGTTCAAC TGGTACGTGGAC GGCGTGGAGGTG 240
 P  K  P  K   D  T  L  M   I  S  R  T   P  E  V  T   C  V  V  V   D  V  S  H   E  D  P  E   V  K  F  N   W  Y  V  D   G  V  E  V>

CATAATGCCAAG ACAAAGCCGCGG GAGGAGCAGTAC AACAGCACGTAC CGTGTGGTCAGC GTCCTCACCGTC CTGCACCAGGAC TGGCTGAATGGC AAGGAGTACAAG TGCAAGGTCTCC 360
 H  N  A  K   T  K  P  R   E  E  Q  Y   N  S  T  Y   R  V  V  S   V  L  T  V   L  H  Q  D   W  L  N  G   K  E  Y  K   C  K  V  S>

AACAAAGCCCTC CCAGCCCCCATC GAGAAAACCATC TCCAAAGCCAAA GGGCAGCCCCGA GAACCACAGGTG TACACCCTGCCC CCATCCCGGGAT GAGCTGACCAAG AACCAGGTCAGC 480
 N  K  A  L   P  A  P  I   E  K  T  I   S  K  A  K   G  Q  P  R   E  P  Q  V   Y  T  L  P   P  S  R  D   E  L  T  K   N  Q  V  S>

CTGACCTGCCTG GTCAAAGGCTTC TATCCCAGCGAC ATCGCCGTGGAG TGGGAGAGCAAT GGGCAGCCGGAG AACAACTACAAG ACCACGCCTCCC GTGCTGGACTCC GACGGCTCCTTC 600
 L  T  C  L   V  K  G  F   Y  P  S  D   I  A  V  E   W  E  S  N   G  Q  P  E   N  N  Y  K   T  T  P  P   V  L  D  S   D  G  S  F>

TTCCTCTACAGC AAGCTCACCGTG GACAAGAGCAGG TGGCAGCAGGGG AACGTCTTCTCA TGCTCCGTGATG CATGAGGCTCTG CACAACCACTAC ACGCAGAAGAGC CTCTCCCTGTCT 720
 F  L  Y  S   K  L  T  V   D  K  S  R   W  Q  Q  G   N  V  F  S   C  S  V  M   H  E  A  L   H  N  H  Y   T  Q  K  S   L  S  L  S>

CCGGGTAAAAGA TCTCCGCAGCCG CAGCCGAAACCG CAGCCGAAACCG GAACCGGAAGGA TCTCTGGAGGTG CTGTTCCAGGGG CCCGGATCCCTG CAGCACTCTGTC CTGCACCTGGTT 840
 P  G  K  R   S  P  Q  P   Q  P  K  P   Q  P  K  P   E  P  E  G   S  L  E  V   L  F  Q  G   P  G  S  L   Q  H  S  V   L  H  L  V>

CCCATTAACGCC ACCTCCAAGGAT GACTCCGATGTG ACAGAGGTGATG TGGCAACCAGCT CTTAGGCGTGGG AGAGGCCTACAG GCCCAAGGATAT GGTGTCCGAATC CAGGATGCTGGA 960
 P  I  N  A   T  S  K  D   D  S  D  V   T  E  V  M   W  Q  P  A   L  R  R  G   R  G  L  Q   A  Q  G  Y   G  V  R  I   Q  D  A  G>

GTTTATCTGCTG TATAGCCAGGTC CTGTTTCAAGAC GTGACTTTCACC ATGGGTCAGGTG GTGTCTCGAGAA GGCCAAGGAAGG CAGGAGACTCTA TTCCGATGTATA AGAAGTATGCCC 1080
 V  Y  L  L   Y  S  Q  V   L  F  Q  D   V  T  F  T   M  G  Q  V   V  S  R  E   G  Q  G  R   Q  E  T  L   F  R  C  I   R  S  M  P>

TCCCACCCGGAC CGGGCCTACAAC AGCTGCTATAGC GCAGGTGTCTTC CATTTACACCAA GGGGATATTCTG AGTGTCATAATT CCCCGGGCAAGG GCGAAACTTAAC CTCTCTCCACAT 1200
 S  H  P  D   R  A  Y  N   S  C  Y  S   A  G  V  F   H  L  H  Q   G  D  I  L   S  V  I  I   P  R  A  R   A  K  L  N   L  S  P  H>

GGAACCTTCCTG GGGTTTGTGAAA CTGTGA
 G  T  F  L   G  F  V  K   L  *
```

FIG. 1I

SEQUENCE LISTING

```
<160> NUMBER OF SEQ ID NOS: 22

<210> SEQ ID NO 1
<211> LENGTH: 1251
<212> TYPE: DNA
<213> ORGANISM: Artificial Sequence
<220> FEATURE:
<223> OTHER INFORMATION: Description of Artificial Sequence: Synthetic
      ps1158 Fc-PS:FasL polynucleotide
<220> FEATURE:
<221> NAME/KEY: CDS
<222> LOCATION: (1)..(1248)

<400> SEQUENCE: 1

atg gct atc atc tac ctc atc ctc ctg ttc acc gct gtg cgg ggc ctc       48
Met Ala Ile Ile Tyr Leu Ile Leu Leu Phe Thr Ala Val Arg Gly Leu
1               5                   10                  15

gac aaa act cac aca tgc cca ccg tgc cca gca cct gaa ctc ctg ggg       96
Asp Lys Thr His Thr Cys Pro Pro Cys Pro Ala Pro Glu Leu Leu Gly
            20                  25                  30

gga ccg tca gtc ttc ctc ttc ccc cca aaa ccc aag gac acc ctc atg      144
Gly Pro Ser Val Phe Leu Phe Pro Pro Lys Pro Lys Asp Thr Leu Met
        35                  40                  45

atc tcc cgg acc cct gag gtc aca tgc gtg gtg gtg gac gtg agc cac      192
Ile Ser Arg Thr Pro Glu Val Thr Cys Val Val Val Asp Val Ser His
    50                  55                  60

gaa gac cct gag gtc aag ttc aac tgg tac gtg gac ggc gtg gag gtg      240
Glu Asp Pro Glu Val Lys Phe Asn Trp Tyr Val Asp Gly Val Glu Val
65                  70                  75                  80

cat aat gcc aag aca aag ccg cgg gag gag cag tac aac agc acg tac      288
His Asn Ala Lys Thr Lys Pro Arg Glu Glu Gln Tyr Asn Ser Thr Tyr
                85                  90                  95

cgt gtg gtc agc gtc ctc acc gtc ctg cac cag gac tgg ctg aat ggc      336
Arg Val Val Ser Val Leu Thr Val Leu His Gln Asp Trp Leu Asn Gly
            100                 105                 110

aag gag tac aag tgc aag gtc tcc aac aaa gcc ctc cca gcc ccc atc      384
Lys Glu Tyr Lys Cys Lys Val Ser Asn Lys Ala Leu Pro Ala Pro Ile
        115                 120                 125

gag aaa acc atc tcc aaa gcc aaa ggg cag ccc cga gaa cca cag gtg      432
Glu Lys Thr Ile Ser Lys Ala Lys Gly Gln Pro Arg Glu Pro Gln Val
    130                 135                 140
```

-continued

```
tac acc ctg ccc cca tcc cgg gat gag ctg acc aag aac cag gtc agc      480
Tyr Thr Leu Pro Pro Ser Arg Asp Glu Leu Thr Lys Asn Gln Val Ser
145                 150                 155                 160

ctg acc tgc ctg gtc aaa ggc ttc tat ccc agc gac atc gcc gtg gag      528
Leu Thr Cys Leu Val Lys Gly Phe Tyr Pro Ser Asp Ile Ala Val Glu
                165                 170                 175

tgg gag agc aat ggg cag ccg gag aac aac tac aag acc acg cct ccc      576
Trp Glu Ser Asn Gly Gln Pro Glu Asn Asn Tyr Lys Thr Thr Pro Pro
            180                 185                 190

gtg ttg gac tcc gac ggc tcc ttc ttc ctc tac agc aag ctc acc gtg      624
Val Leu Asp Ser Asp Gly Ser Phe Phe Leu Tyr Ser Lys Leu Thr Val
        195                 200                 205

gac aag agc agg tgg cag cag ggg aac gtc ttc tca tgc tcc gtg atg      672
Asp Lys Ser Arg Trp Gln Gln Gly Asn Val Phe Ser Cys Ser Val Met
    210                 215                 220

cat gag gct ctg cac aac cac tac acg cag aag agc ctc tcc ctg tct      720
His Glu Ala Leu His Asn His Tyr Thr Gln Lys Ser Leu Ser Leu Ser
225                 230                 235                 240

ccg ggt aaa aga tct ccg cag ccg cag ccg aaa ccg cag ccg aaa ccg      768
Pro Gly Lys Arg Ser Pro Gln Pro Gln Pro Lys Pro Gln Pro Lys Pro
                245                 250                 255

gaa ccg gaa gga tct ctg gag gtg ctg ttc cag ggg ccc gga tcc ctg      816
Glu Pro Glu Gly Ser Leu Glu Val Leu Phe Gln Gly Pro Gly Ser Leu
            260                 265                 270

cag gaa aaa aag gag ctg agg aaa gtg gcc cat tta aca ggc aag tcc      864
Gln Glu Lys Lys Glu Leu Arg Lys Val Ala His Leu Thr Gly Lys Ser
        275                 280                 285

aac tca agg tcc atg cct ctg gaa tgg gaa gac acc tat gga att gtc      912
Asn Ser Arg Ser Met Pro Leu Glu Trp Glu Asp Thr Tyr Gly Ile Val
    290                 295                 300

ctg ctt tct gga gtg aag tat aag aag ggt ggc ctt gtg atc aat gaa      960
Leu Leu Ser Gly Val Lys Tyr Lys Lys Gly Gly Leu Val Ile Asn Glu
305                 310                 315                 320

act ggg ctg tac ttt gta tat tcc aaa gta tac ttc cgg ggt caa tct     1008
Thr Gly Leu Tyr Phe Val Tyr Ser Lys Val Tyr Phe Arg Gly Gln Ser
                325                 330                 335

tgc aac aac ctg ccc ctg agc cac aag gtc tac atg agg aac tct aag     1056
Cys Asn Asn Leu Pro Leu Ser His Lys Val Tyr Met Arg Asn Ser Lys
            340                 345                 350

tat ccc cag gat ctg gtg atg atg gag ggg aag atg atg agc tac tgc     1104
Tyr Pro Gln Asp Leu Val Met Met Glu Gly Lys Met Met Ser Tyr Cys
        355                 360                 365

act act ggg cag atg tgg gcc cgc agc agc tac ctg ggg gca gtg ttc     1152
Thr Thr Gly Gln Met Trp Ala Arg Ser Ser Tyr Leu Gly Ala Val Phe
    370                 375                 380

aat ctt acc agt gct gat cat tta tat gtc aac gta tct gag ctc tct     1200
Asn Leu Thr Ser Ala Asp His Leu Tyr Val Asn Val Ser Glu Leu Ser
385                 390                 395                 400

ctg gtc aat ttt gag gaa tct cag acg ttt ttc ggc tta tat aag ctc     1248
Leu Val Asn Phe Glu Glu Ser Gln Thr Phe Phe Gly Leu Tyr Lys Leu
                405                 410                 415

taa                                                                 1251
```

<210> SEQ ID NO 2
<211> LENGTH: 416
<212> TYPE: PRT
<213> ORGANISM: Artificial Sequence
<220> FEATURE:
<223> OTHER INFORMATION: Description of Artificial Sequence: Synthetic construct polypeptide

```
<400> SEQUENCE: 2

Met Ala Ile Ile Tyr Leu Ile Leu Leu Phe Thr Ala Val Arg Gly Leu
1               5                   10                  15

Asp Lys Thr His Thr Cys Pro Pro Cys Pro Ala Pro Glu Leu Leu Gly
            20                  25                  30

Gly Pro Ser Val Phe Leu Phe Pro Pro Lys Pro Lys Asp Thr Leu Met
        35                  40                  45

Ile Ser Arg Thr Pro Glu Val Thr Cys Val Val Val Asp Val Ser His
    50                  55                  60

Glu Asp Pro Glu Val Lys Phe Asn Trp Tyr Val Asp Gly Val Glu Val
65                  70                  75                  80

His Asn Ala Lys Thr Lys Pro Arg Glu Glu Gln Tyr Asn Ser Thr Tyr
                85                  90                  95

Arg Val Val Ser Val Leu Thr Val Leu His Gln Asp Trp Leu Asn Gly
            100                 105                 110

Lys Glu Tyr Lys Cys Lys Val Ser Asn Lys Ala Leu Pro Ala Pro Ile
        115                 120                 125

Glu Lys Thr Ile Ser Lys Ala Lys Gly Gln Pro Arg Glu Pro Gln Val
    130                 135                 140

Tyr Thr Leu Pro Pro Ser Arg Asp Glu Leu Thr Lys Asn Gln Val Ser
145                 150                 155                 160

Leu Thr Cys Leu Val Lys Gly Phe Tyr Pro Ser Asp Ile Ala Val Glu
                165                 170                 175

Trp Glu Ser Asn Gly Gln Pro Glu Asn Asn Tyr Lys Thr Thr Pro Pro
            180                 185                 190

Val Leu Asp Ser Asp Gly Ser Phe Phe Leu Tyr Ser Lys Leu Thr Val
        195                 200                 205

Asp Lys Ser Arg Trp Gln Gln Gly Asn Val Phe Ser Cys Ser Val Met
    210                 215                 220

His Glu Ala Leu His Asn His Tyr Thr Gln Lys Ser Leu Ser Leu Ser
225                 230                 235                 240

Pro Gly Lys Arg Ser Pro Gln Pro Gln Pro Lys Pro Gln Pro Lys Pro
                245                 250                 255

Glu Pro Glu Gly Ser Leu Glu Val Leu Phe Gln Gly Pro Gly Ser Leu
            260                 265                 270

Gln Glu Lys Lys Glu Leu Arg Lys Val Ala His Leu Thr Gly Lys Ser
        275                 280                 285

Asn Ser Arg Ser Met Pro Leu Glu Trp Glu Asp Thr Tyr Gly Ile Val
    290                 295                 300

Leu Leu Ser Gly Val Lys Tyr Lys Lys Gly Gly Leu Val Ile Asn Glu
305                 310                 315                 320

Thr Gly Leu Tyr Phe Val Tyr Ser Lys Val Tyr Phe Arg Gly Gln Ser
                325                 330                 335

Cys Asn Asn Leu Pro Leu Ser His Lys Val Tyr Met Arg Asn Ser Lys
            340                 345                 350

Tyr Pro Gln Asp Leu Val Met Met Glu Gly Lys Met Met Ser Tyr Cys
        355                 360                 365

Thr Thr Gly Gln Met Trp Ala Arg Ser Ser Tyr Leu Gly Ala Val Phe
    370                 375                 380

Asn Leu Thr Ser Ala Asp His Leu Tyr Val Asn Val Ser Glu Leu Ser
385                 390                 395                 400

Leu Val Asn Phe Glu Glu Ser Gln Thr Phe Phe Gly Leu Tyr Lys Leu
                405                 410                 415
```

```
<210> SEQ ID NO 3
<211> LENGTH: 1221
<212> TYPE: DNA
<213> ORGANISM: Artificial Sequence
<220> FEATURE:
<223> OTHER INFORMATION: Description of Artificial Sequence: Synthetic
      ps1117 Fc:FasL polynucleotide
<220> FEATURE:
<221> NAME/KEY: CDS
<222> LOCATION: (1)..(1218)

<400> SEQUENCE: 3

atg gct atc atc tac ctc atc ctc ctg ttc acc gct gtg cgg ggc ctc       48
Met Ala Ile Ile Tyr Leu Ile Leu Leu Phe Thr Ala Val Arg Gly Leu
1               5                   10                  15

gac aaa act cac aca tgc cca ccg tgc cca gca cct gaa ctc ctg ggg       96
Asp Lys Thr His Thr Cys Pro Pro Cys Pro Ala Pro Glu Leu Leu Gly
            20                  25                  30

gga ccg tca gtc ttc ctc ttc ccc cca aaa ccc aag gac acc ctc atg      144
Gly Pro Ser Val Phe Leu Phe Pro Pro Lys Pro Lys Asp Thr Leu Met
        35                  40                  45

atc tcc cgg acc cct gag gtc aca tgc gtg gtg gtg gac gtg agc cac      192
Ile Ser Arg Thr Pro Glu Val Thr Cys Val Val Val Asp Val Ser His
    50                  55                  60

gaa gac cct gag gtc aag ttc aac tgg tac gtg gac ggc gtg gag gtg      240
Glu Asp Pro Glu Val Lys Phe Asn Trp Tyr Val Asp Gly Val Glu Val
65                  70                  75                  80

cat aat gcc aag aca aag ccg cgg gag gag cag tac aac agc acg tac      288
His Asn Ala Lys Thr Lys Pro Arg Glu Glu Gln Tyr Asn Ser Thr Tyr
                85                  90                  95

cgt gtg gtc agc gtc ctc acc gtc ctg cac cag gac tgg ctg aat ggc      336
Arg Val Val Ser Val Leu Thr Val Leu His Gln Asp Trp Leu Asn Gly
            100                 105                 110

aag gag tac aag tgc aag gtc tcc aac aaa gcc ctc cca gcc ccc atc      384
Lys Glu Tyr Lys Cys Lys Val Ser Asn Lys Ala Leu Pro Ala Pro Ile
        115                 120                 125

gag aaa acc atc tcc aaa gcc aaa ggg cag ccc cga gaa cca cag gtg      432
Glu Lys Thr Ile Ser Lys Ala Lys Gly Gln Pro Arg Glu Pro Gln Val
    130                 135                 140

tac acc ctg ccc cca tcc cgg gat gag ctg acc aag aac cag gtc agc      480
Tyr Thr Leu Pro Pro Ser Arg Asp Glu Leu Thr Lys Asn Gln Val Ser
145                 150                 155                 160

ctg acc tgc ctg gtc aaa ggc ttc tat ccc agc gac atc gcc gtg gag      528
Leu Thr Cys Leu Val Lys Gly Phe Tyr Pro Ser Asp Ile Ala Val Glu
                165                 170                 175

tgg gag agc aat ggg cag ccg gag aac aac tac aag acc acg cct ccc      576
Trp Glu Ser Asn Gly Gln Pro Glu Asn Asn Tyr Lys Thr Thr Pro Pro
            180                 185                 190

gtg ttg gac tcc gac ggc tcc ttc ttc ctc tac agc aag ctc acc gtg      624
Val Leu Asp Ser Asp Gly Ser Phe Phe Leu Tyr Ser Lys Leu Thr Val
        195                 200                 205

gac aag agc agg tgg cag cag ggg aac gtc ttc tca tgc tcc gtg atg      672
Asp Lys Ser Arg Trp Gln Gln Gly Asn Val Phe Ser Cys Ser Val Met
    210                 215                 220

cat gag gct ctg cac aac cac tac acg cag aag agc ctc tcc ctg tct      720
His Glu Ala Leu His Asn His Tyr Thr Gln Lys Ser Leu Ser Leu Ser
225                 230                 235                 240

ccg ggt aaa aga tct ccg cag ccg cag ccg aaa ccg cag ccg aaa ccg      768
Pro Gly Lys Arg Ser Pro Gln Pro Gln Pro Lys Pro Gln Pro Lys Pro
                245                 250                 255
```

-continued

```
gaa ccg gaa gga tcc ctg cag gaa aaa aag gag ctg agg aaa gtg gcc      816
Glu Pro Glu Gly Ser Leu Gln Glu Lys Lys Glu Leu Arg Lys Val Ala
            260                 265                 270

cat tta aca ggc aag tcc aac tca agg tcc atg cct ctg gaa tgg gaa      864
His Leu Thr Gly Lys Ser Asn Ser Arg Ser Met Pro Leu Glu Trp Glu
        275                 280                 285

gac acc tat gga att gtc ctg ctt tct gga gtg aag tat aag aag ggt      912
Asp Thr Tyr Gly Ile Val Leu Leu Ser Gly Val Lys Tyr Lys Lys Gly
    290                 295                 300

ggc ctt gtg atc aat gaa act ggg ctg tac ttt gta tat tcc aaa gta      960
Gly Leu Val Ile Asn Glu Thr Gly Leu Tyr Phe Val Tyr Ser Lys Val
305                 310                 315                 320

tac ttc cgg ggt caa tct tgc aac aac ctg ccc ctg agc cac aag gtc     1008
Tyr Phe Arg Gly Gln Ser Cys Asn Asn Leu Pro Leu Ser His Lys Val
            325                 330                 335

tac atg agg aac tct aag tat ccc cag gat ctg gtg atg atg gag ggg     1056
Tyr Met Arg Asn Ser Lys Tyr Pro Gln Asp Leu Val Met Met Glu Gly
            340                 345                 350

aag atg atg agc tac tgc act act ggg cag atg tgg gcc cgc agc agc     1104
Lys Met Met Ser Tyr Cys Thr Thr Gly Gln Met Trp Ala Arg Ser Ser
        355                 360                 365

tac ctg ggg gca gtg ttc aat ctt acc agt gct gat cat tta tat gtc     1152
Tyr Leu Gly Ala Val Phe Asn Leu Thr Ser Ala Asp His Leu Tyr Val
    370                 375                 380

aac gta tct gag ctc tct ctg gtc aat ttt gag gaa tct cag acg ttt     1200
Asn Val Ser Glu Leu Ser Leu Val Asn Phe Glu Glu Ser Gln Thr Phe
385                 390                 395                 400

ttc ggc tta tat aag ctc taa                                          1221
Phe Gly Leu Tyr Lys Leu
                405
```

<210> SEQ ID NO 4
<211> LENGTH: 406
<212> TYPE: PRT
<213> ORGANISM: Artificial Sequence
<220> FEATURE:
<223> OTHER INFORMATION: Description of Artificial Sequence: Synthetic construct polypeptide

<400> SEQUENCE: 4

```
Met Ala Ile Ile Tyr Leu Ile Leu Leu Phe Thr Ala Val Arg Gly Leu
1               5                   10                  15

Asp Lys Thr His Thr Cys Pro Pro Cys Pro Ala Pro Glu Leu Leu Gly
            20                  25                  30

Gly Pro Ser Val Phe Leu Phe Pro Pro Lys Pro Lys Asp Thr Leu Met
        35                  40                  45

Ile Ser Arg Thr Pro Glu Val Thr Cys Val Val Val Asp Val Ser His
    50                  55                  60

Glu Asp Pro Glu Val Lys Phe Asn Trp Tyr Val Asp Gly Val Glu Val
65                  70                  75                  80

His Asn Ala Lys Thr Lys Pro Arg Glu Glu Gln Tyr Asn Ser Thr Tyr
                85                  90                  95

Arg Val Val Ser Val Leu Thr Val Leu His Gln Asp Trp Leu Asn Gly
            100                 105                 110

Lys Glu Tyr Lys Cys Lys Val Ser Asn Lys Ala Leu Pro Ala Pro Ile
        115                 120                 125

Glu Lys Thr Ile Ser Lys Ala Lys Gly Gln Pro Arg Glu Pro Gln Val
    130                 135                 140

Tyr Thr Leu Pro Pro Ser Arg Asp Glu Leu Thr Lys Asn Gln Val Ser
```

```
145                 150                 155                 160

Leu Thr Cys Leu Val Lys Gly Phe Tyr Pro Ser Asp Ile Ala Val Glu
                165                 170                 175

Trp Glu Ser Asn Gly Gln Pro Glu Asn Asn Tyr Lys Thr Thr Pro Pro
            180                 185                 190

Val Leu Asp Ser Asp Gly Ser Phe Phe Leu Tyr Ser Lys Leu Thr Val
        195                 200                 205

Asp Lys Ser Arg Trp Gln Gln Gly Asn Val Phe Ser Cys Ser Val Met
    210                 215                 220

His Glu Ala Leu His Asn His Tyr Thr Gln Lys Ser Leu Ser Leu Ser
225                 230                 235                 240

Pro Gly Lys Arg Ser Pro Gln Pro Gln Pro Lys Pro Gln Pro Lys Pro
                245                 250                 255

Glu Pro Glu Gly Ser Leu Gln Glu Lys Lys Glu Leu Arg Lys Val Ala
            260                 265                 270

His Leu Thr Gly Lys Ser Asn Ser Arg Ser Met Pro Leu Glu Trp Glu
        275                 280                 285

Asp Thr Tyr Gly Ile Val Leu Leu Ser Gly Val Lys Tyr Lys Lys Gly
    290                 295                 300

Gly Leu Val Ile Asn Glu Thr Gly Leu Tyr Phe Val Tyr Ser Lys Val
305                 310                 315                 320

Tyr Phe Arg Gly Gln Ser Cys Asn Asn Leu Pro Leu Ser His Lys Val
                325                 330                 335

Tyr Met Arg Asn Ser Lys Tyr Pro Gln Asp Leu Val Met Met Glu Gly
            340                 345                 350

Lys Met Met Ser Tyr Cys Thr Thr Gly Gln Met Trp Ala Arg Ser Ser
        355                 360                 365

Tyr Leu Gly Ala Val Phe Asn Leu Thr Ser Ala Asp His Leu Tyr Val
    370                 375                 380

Asn Val Ser Glu Leu Ser Leu Val Asn Phe Glu Glu Ser Gln Thr Phe
385                 390                 395                 400

Phe Gly Leu Tyr Lys Leu
                405


<210> SEQ ID NO 5
<211> LENGTH: 1239
<212> TYPE: DNA
<213> ORGANISM: Artificial Sequence
<220> FEATURE:
<223> OTHER INFORMATION: Description of Artificial Sequence: Synthetic
      ps1236 Fc:EDA1 polynucleotide
<220> FEATURE:
<221> NAME/KEY: CDS
<222> LOCATION: (1)..(1236)

<400> SEQUENCE: 5

atg gct atc atc tac ctc atc ctc ctg ttc acc gct gtg cgg ggc ctc       48
Met Ala Ile Ile Tyr Leu Ile Leu Leu Phe Thr Ala Val Arg Gly Leu
1               5                   10                  15

gac aaa act cac aca tgc cca ccg tgc cca gca cct gaa ctc ctg ggg       96
Asp Lys Thr His Thr Cys Pro Pro Cys Pro Ala Pro Glu Leu Leu Gly
            20                  25                  30

gga ccg tca gtc ttc ctc ttc ccc cca aaa ccc aag gac acc ctc atg      144
Gly Pro Ser Val Phe Leu Phe Pro Pro Lys Pro Lys Asp Thr Leu Met
        35                  40                  45

atc tcc cgg acc cct gag gtc aca tgc gtg gtg gtg gac gtg agc cac      192
Ile Ser Arg Thr Pro Glu Val Thr Cys Val Val Val Asp Val Ser His
    50                  55                  60
```

-continued

```
gaa gac cct gag gtc aag ttc aac tgg tac gtg gac ggc gtg gag gtg      240
Glu Asp Pro Glu Val Lys Phe Asn Trp Tyr Val Asp Gly Val Glu Val
65                  70                  75                  80

cat aat gcc aag aca aag ccg cgg gag gag cag tac aac agc acg tac      288
His Asn Ala Lys Thr Lys Pro Arg Glu Glu Gln Tyr Asn Ser Thr Tyr
                85                  90                  95

cgt gtg gtc agc gtc ctc acc gtc ctg cac cag gac tgg ctg aat ggc      336
Arg Val Val Ser Val Leu Thr Val Leu His Gln Asp Trp Leu Asn Gly
            100                 105                 110

aag gag tac aag tgc aag gtc tcc aac aaa gcc ctc cca gcc ccc atc      384
Lys Glu Tyr Lys Cys Lys Val Ser Asn Lys Ala Leu Pro Ala Pro Ile
        115                 120                 125

gag aaa acc atc tcc aaa gcc aaa ggg cag ccc cga gaa cca cag gtg      432
Glu Lys Thr Ile Ser Lys Ala Lys Gly Gln Pro Arg Glu Pro Gln Val
    130                 135                 140

tac acc ctg ccc cca tcc cgg gat gag ctg acc aag aac cag gtc agc      480
Tyr Thr Leu Pro Pro Ser Arg Asp Glu Leu Thr Lys Asn Gln Val Ser
145                 150                 155                 160

ctg acc tgc ctg gtc aaa ggc ttc tat ccc agc gac atc gcc gtg gag      528
Leu Thr Cys Leu Val Lys Gly Phe Tyr Pro Ser Asp Ile Ala Val Glu
                165                 170                 175

tgg gag agc aat ggg cag ccg gag aac aac tac aag acc acg cct ccc      576
Trp Glu Ser Asn Gly Gln Pro Glu Asn Asn Tyr Lys Thr Thr Pro Pro
            180                 185                 190

gtg ttg gac tcc gac ggc tcc ttc ttc ctc tac agc aag ctc acc gtg      624
Val Leu Asp Ser Asp Gly Ser Phe Phe Leu Tyr Ser Lys Leu Thr Val
        195                 200                 205

gac aag agc agg tgg cag cag ggg aac gtc ttc tca tgc tcc gtg atg      672
Asp Lys Ser Arg Trp Gln Gln Gly Asn Val Phe Ser Cys Ser Val Met
    210                 215                 220

cat gag gct ctg cac aac cac tac acg cag aag agc ctc tcc ctg tct      720
His Glu Ala Leu His Asn His Tyr Thr Gln Lys Ser Leu Ser Leu Ser
225                 230                 235                 240

ccg ggt aaa aga tct ccg cag ccg cag ccg aaa ccg cag ccg aaa ccg      768
Pro Gly Lys Arg Ser Pro Gln Pro Gln Pro Lys Pro Gln Pro Lys Pro
                245                 250                 255

gaa ccg gaa gga tcc ctg cag gtc gac gaa aat cag cca gct gtg gtg      816
Glu Pro Glu Gly Ser Leu Gln Val Asp Glu Asn Gln Pro Ala Val Val
            260                 265                 270

cat ctg cag ggc caa ggg tca gca att caa gtc aaa aat gat ctt tca      864
His Leu Gln Gly Gln Gly Ser Ala Ile Gln Val Lys Asn Asp Leu Ser
        275                 280                 285

ggt gga gtg ctc aat gac tgg tct cgc atc act atg aac cct aag gtg      912
Gly Gly Val Leu Asn Asp Trp Ser Arg Ile Thr Met Asn Pro Lys Val
    290                 295                 300

ttt aaa cta cat ccc cgc agc ggg gag ctg gag gta ctg gtg gac ggc      960
Phe Lys Leu His Pro Arg Ser Gly Glu Leu Glu Val Leu Val Asp Gly
305                 310                 315                 320

acc tac ttc atc tat agt cag gta gaa gtc tac tac atc aac ttc act     1008
Thr Tyr Phe Ile Tyr Ser Gln Val Glu Val Tyr Tyr Ile Asn Phe Thr
                325                 330                 335

gac ttt gcc agc tac gag gtg gtg gtg gat gag aag ccc ttc ctg cag     1056
Asp Phe Ala Ser Tyr Glu Val Val Val Asp Glu Lys Pro Phe Leu Gln
            340                 345                 350

tgc acc cgc agc att gag aca ggg aag acc aac tac aac act tgc tat     1104
Cys Thr Arg Ser Ile Glu Thr Gly Lys Thr Asn Tyr Asn Thr Cys Tyr
        355                 360                 365

act gca ggc gtg tgc ctc ctc aag gcc agg cag aaa atc gcc gtg aag     1152
Thr Ala Gly Val Cys Leu Leu Lys Ala Arg Gln Lys Ile Ala Val Lys
```

```
    370                 375                 380

atg gtg cac gct gac atc tct atc aat atg agc aag cac acc acc ttc      1200
Met Val His Ala Asp Ile Ser Ile Asn Met Ser Lys His Thr Thr Phe
385                 390                 395                 400

ttc ggg gcc atc agg ctg ggc gaa gcc cct gca tcc tag                  1239
Phe Gly Ala Ile Arg Leu Gly Glu Ala Pro Ala Ser
                405                 410


<210> SEQ ID NO 6
<211> LENGTH: 412
<212> TYPE: PRT
<213> ORGANISM: Artificial Sequence
<220> FEATURE:
<223> OTHER INFORMATION: Description of Artificial Sequence: Synthetic
      construct polypeptide

<400> SEQUENCE: 6

Met Ala Ile Ile Tyr Leu Ile Leu Leu Phe Thr Ala Val Arg Gly Leu
1               5                   10                  15

Asp Lys Thr His Thr Cys Pro Pro Cys Pro Ala Pro Glu Leu Leu Gly
            20                  25                  30

Gly Pro Ser Val Phe Leu Phe Pro Pro Lys Pro Lys Asp Thr Leu Met
        35                  40                  45

Ile Ser Arg Thr Pro Glu Val Thr Cys Val Val Val Asp Val Ser His
    50                  55                  60

Glu Asp Pro Glu Val Lys Phe Asn Trp Tyr Val Asp Gly Val Glu Val
65                  70                  75                  80

His Asn Ala Lys Thr Lys Pro Arg Glu Glu Gln Tyr Asn Ser Thr Tyr
                85                  90                  95

Arg Val Val Ser Val Leu Thr Val Leu His Gln Asp Trp Leu Asn Gly
            100                 105                 110

Lys Glu Tyr Lys Cys Lys Val Ser Asn Lys Ala Leu Pro Ala Pro Ile
        115                 120                 125

Glu Lys Thr Ile Ser Lys Ala Lys Gly Gln Pro Arg Glu Pro Gln Val
    130                 135                 140

Tyr Thr Leu Pro Pro Ser Arg Asp Glu Leu Thr Lys Asn Gln Val Ser
145                 150                 155                 160

Leu Thr Cys Leu Val Lys Gly Phe Tyr Pro Ser Asp Ile Ala Val Glu
                165                 170                 175

Trp Glu Ser Asn Gly Gln Pro Glu Asn Asn Tyr Lys Thr Thr Pro Pro
            180                 185                 190

Val Leu Asp Ser Asp Gly Ser Phe Phe Leu Tyr Ser Lys Leu Thr Val
        195                 200                 205

Asp Lys Ser Arg Trp Gln Gln Gly Asn Val Phe Ser Cys Ser Val Met
    210                 215                 220

His Glu Ala Leu His Asn His Tyr Thr Gln Lys Ser Leu Ser Leu Ser
225                 230                 235                 240

Pro Gly Lys Arg Ser Pro Gln Pro Gln Pro Lys Pro Gln Pro Lys Pro
                245                 250                 255

Glu Pro Glu Gly Ser Leu Gln Val Asp Glu Asn Gln Pro Ala Val Val
            260                 265                 270

His Leu Gln Gly Gln Gly Ser Ala Ile Gln Val Lys Asn Asp Leu Ser
        275                 280                 285

Gly Gly Val Leu Asn Asp Trp Ser Arg Ile Thr Met Asn Pro Lys Val
    290                 295                 300

Phe Lys Leu His Pro Arg Ser Gly Glu Leu Glu Val Leu Val Asp Gly
```

```
305                 310                 315                 320

Thr Tyr Phe Ile Tyr Ser Gln Val Glu Val Tyr Tyr Ile Asn Phe Thr
                325                 330                 335

Asp Phe Ala Ser Tyr Glu Val Val Val Asp Glu Lys Pro Phe Leu Gln
            340                 345                 350

Cys Thr Arg Ser Ile Glu Thr Gly Lys Thr Asn Tyr Asn Thr Cys Tyr
        355                 360                 365

Thr Ala Gly Val Cys Leu Leu Lys Ala Arg Gln Lys Ile Ala Val Lys
    370                 375                 380

Met Val His Ala Asp Ile Ser Ile Asn Met Ser Lys His Thr Thr Phe
385                 390                 395                 400

Phe Gly Ala Ile Arg Leu Gly Glu Ala Pro Ala Ser
                405                 410


<210> SEQ ID NO 7
<211> LENGTH: 1233
<212> TYPE: DNA
<213> ORGANISM: Artificial Sequence
<220> FEATURE:
<223> OTHER INFORMATION: Description of Artificial Sequence: Synthetic
      ps1235 Fc:EDA2 polynucleotide
<220> FEATURE:
<221> NAME/KEY: CDS
<222> LOCATION: (1)..(1230)

<400> SEQUENCE: 7

atg gct atc atc tac ctc atc ctc ctg ttc acc gct gtg cgg ggc ctc       48
Met Ala Ile Ile Tyr Leu Ile Leu Leu Phe Thr Ala Val Arg Gly Leu
1               5                   10                  15

gac aaa act cac aca tgc cca ccg tgc cca gca cct gaa ctc ctg ggg       96
Asp Lys Thr His Thr Cys Pro Pro Cys Pro Ala Pro Glu Leu Leu Gly
            20                  25                  30

gga ccg tca gtc ttc ctc ttc ccc cca aaa ccc aag gac acc ctc atg      144
Gly Pro Ser Val Phe Leu Phe Pro Pro Lys Pro Lys Asp Thr Leu Met
        35                  40                  45

atc tcc cgg acc cct gag gtc aca tgc gtg gtg gtg gac gtg agc cac      192
Ile Ser Arg Thr Pro Glu Val Thr Cys Val Val Val Asp Val Ser His
    50                  55                  60

gaa gac cct gag gtc aag ttc aac tgg tac gtg gac ggc gtg gag gtg      240
Glu Asp Pro Glu Val Lys Phe Asn Trp Tyr Val Asp Gly Val Glu Val
65                  70                  75                  80

cat aat gcc aag aca aag ccg cgg gag gag cag tac aac agc acg tac      288
His Asn Ala Lys Thr Lys Pro Arg Glu Glu Gln Tyr Asn Ser Thr Tyr
                85                  90                  95

cgt gtg gtc agc gtc ctc acc gtc ctg cac cag gac tgg ctg aat ggc      336
Arg Val Val Ser Val Leu Thr Val Leu His Gln Asp Trp Leu Asn Gly
            100                 105                 110

aag gag tac aag tgc aag gtc tcc aac aaa gcc ctc cca gcc ccc atc      384
Lys Glu Tyr Lys Cys Lys Val Ser Asn Lys Ala Leu Pro Ala Pro Ile
        115                 120                 125

gag aaa acc atc tcc aaa gcc aaa ggg cag ccc cga gaa cca cag gtg      432
Glu Lys Thr Ile Ser Lys Ala Lys Gly Gln Pro Arg Glu Pro Gln Val
    130                 135                 140

tac acc ctg ccc cca tcc cgg gat gag ctg acc aag aac cag gtc agc      480
Tyr Thr Leu Pro Pro Ser Arg Asp Glu Leu Thr Lys Asn Gln Val Ser
145                 150                 155                 160

ctg acc tgc ctg gtc aaa ggc ttc tat ccc agc gac atc gcc gtg gag      528
Leu Thr Cys Leu Val Lys Gly Phe Tyr Pro Ser Asp Ile Ala Val Glu
                165                 170                 175

tgg gag agc aat ggg cag ccg gag aac aac tac aag acc acg cct ccc      576
```

-continued

```
Trp Glu Ser Asn Gly Gln Pro Glu Asn Asn Tyr Lys Thr Thr Pro Pro
            180                 185                 190

gtg ttg gac tcc gac ggc tcc ttc ttc ctc tac agc aag ctc acc gtg      624
Val Leu Asp Ser Asp Gly Ser Phe Phe Leu Tyr Ser Lys Leu Thr Val
        195                 200                 205

gac aag agc agg tgg cag cag ggg aac gtc ttc tca tgc tcc gtg atg      672
Asp Lys Ser Arg Trp Gln Gln Gly Asn Val Phe Ser Cys Ser Val Met
    210                 215                 220

cat gag gct ctg cac aac cac tac acg cag aag agc ctc tcc ctg tct      720
His Glu Ala Leu His Asn His Tyr Thr Gln Lys Ser Leu Ser Leu Ser
225                 230                 235                 240

ccg ggt aaa aga tct ccg cag ccg cag ccg aaa ccg cag ccg aaa ccg      768
Pro Gly Lys Arg Ser Pro Gln Pro Gln Pro Lys Pro Gln Pro Lys Pro
                245                 250                 255

gaa ccg gaa gga tcc ctg cag gtc gac gaa aat cag cca gct gtg gtg      816
Glu Pro Glu Gly Ser Leu Gln Val Asp Glu Asn Gln Pro Ala Val Val
            260                 265                 270

cat ctg cag ggc caa ggg tca gca att caa gtc aaa aat gat ctt tca      864
His Leu Gln Gly Gln Gly Ser Ala Ile Gln Val Lys Asn Asp Leu Ser
        275                 280                 285

ggt gga gtg ctc aat gac tgg tct cgc atc act atg aac cct aag gtg      912
Gly Gly Val Leu Asn Asp Trp Ser Arg Ile Thr Met Asn Pro Lys Val
    290                 295                 300

ttt aaa cta cat ccc cgc agc ggg gag ctg gag gta ctg gtg gac ggc      960
Phe Lys Leu His Pro Arg Ser Gly Glu Leu Glu Val Leu Val Asp Gly
305                 310                 315                 320

acc tac ttc atc tat agt cag gta tac tac atc aac ttc act gac ttt     1008
Thr Tyr Phe Ile Tyr Ser Gln Val Tyr Tyr Ile Asn Phe Thr Asp Phe
                325                 330                 335

gcc agc tac gag gtg gtg gtg gat gag aag ccc ttc ctg cag tgc acc     1056
Ala Ser Tyr Glu Val Val Val Asp Glu Lys Pro Phe Leu Gln Cys Thr
            340                 345                 350

cgc agc att gag aca ggg aag acc aac tac aac act tgc tat act gca     1104
Arg Ser Ile Glu Thr Gly Lys Thr Asn Tyr Asn Thr Cys Tyr Thr Ala
        355                 360                 365

ggc gtg tgc ctc ctc aag gcc agg cag aaa atc gcc gtg aag atg gtg     1152
Gly Val Cys Leu Leu Lys Ala Arg Gln Lys Ile Ala Val Lys Met Val
    370                 375                 380

cac gct gac atc tct atc aat atg agc aag cac acc acc ttc ttc ggg     1200
His Ala Asp Ile Ser Ile Asn Met Ser Lys His Thr Thr Phe Phe Gly
385                 390                 395                 400

gcc atc agg ctg ggc gaa gcc cct gca tcc tag                         1233
Ala Ile Arg Leu Gly Glu Ala Pro Ala Ser
                405                 410


<210> SEQ ID NO 8
<211> LENGTH: 410
<212> TYPE: PRT
<213> ORGANISM: Artificial Sequence
<220> FEATURE:
<223> OTHER INFORMATION: Description of Artificial Sequence: Synthetic
      construct polypeptide

<400> SEQUENCE: 8

Met Ala Ile Ile Tyr Leu Ile Leu Leu Phe Thr Ala Val Arg Gly Leu
1               5                   10                  15

Asp Lys Thr His Thr Cys Pro Pro Cys Pro Ala Pro Glu Leu Leu Gly
            20                  25                  30

Gly Pro Ser Val Phe Leu Phe Pro Pro Lys Pro Lys Asp Thr Leu Met
        35                  40                  45
```

-continued

```
Ile Ser Arg Thr Pro Glu Val Thr Cys Val Val Val Asp Val Ser His
    50                  55                  60

Glu Asp Pro Glu Val Lys Phe Asn Trp Tyr Val Asp Gly Val Glu Val
65                  70                  75                  80

His Asn Ala Lys Thr Lys Pro Arg Glu Glu Gln Tyr Asn Ser Thr Tyr
                85                  90                  95

Arg Val Val Ser Val Leu Thr Val Leu His Gln Asp Trp Leu Asn Gly
            100                 105                 110

Lys Glu Tyr Lys Cys Lys Val Ser Asn Lys Ala Leu Pro Ala Pro Ile
        115                 120                 125

Glu Lys Thr Ile Ser Lys Ala Lys Gly Gln Pro Arg Glu Pro Gln Val
    130                 135                 140

Tyr Thr Leu Pro Pro Ser Arg Asp Glu Leu Thr Lys Asn Gln Val Ser
145                 150                 155                 160

Leu Thr Cys Leu Val Lys Gly Phe Tyr Pro Ser Asp Ile Ala Val Glu
                165                 170                 175

Trp Glu Ser Asn Gly Gln Pro Glu Asn Asn Tyr Lys Thr Thr Pro Pro
            180                 185                 190

Val Leu Asp Ser Asp Gly Ser Phe Phe Leu Tyr Ser Lys Leu Thr Val
        195                 200                 205

Asp Lys Ser Arg Trp Gln Gln Gly Asn Val Phe Ser Cys Ser Val Met
    210                 215                 220

His Glu Ala Leu His Asn His Tyr Thr Gln Lys Ser Leu Ser Leu Ser
225                 230                 235                 240

Pro Gly Lys Arg Ser Pro Gln Pro Gln Pro Lys Pro Gln Pro Lys Pro
                245                 250                 255

Glu Pro Glu Gly Ser Leu Gln Val Asp Glu Asn Gln Pro Ala Val Val
            260                 265                 270

His Leu Gln Gly Gln Gly Ser Ala Ile Gln Val Lys Asn Asp Leu Ser
        275                 280                 285

Gly Gly Val Leu Asn Asp Trp Ser Arg Ile Thr Met Asn Pro Lys Val
    290                 295                 300

Phe Lys Leu His Pro Arg Ser Gly Glu Leu Glu Val Leu Val Asp Gly
305                 310                 315                 320

Thr Tyr Phe Ile Tyr Ser Gln Val Tyr Tyr Ile Asn Phe Thr Asp Phe
                325                 330                 335

Ala Ser Tyr Glu Val Val Val Asp Glu Lys Pro Phe Leu Gln Cys Thr
            340                 345                 350

Arg Ser Ile Glu Thr Gly Lys Thr Asn Tyr Asn Thr Cys Tyr Thr Ala
        355                 360                 365

Gly Val Cys Leu Leu Lys Ala Arg Gln Lys Ile Ala Val Lys Met Val
    370                 375                 380

His Ala Asp Ile Ser Ile Asn Met Ser Lys His Thr Thr Phe Phe Gly
385                 390                 395                 400

Ala Ile Arg Leu Gly Glu Ala Pro Ala Ser
                405                 410
```

<210> SEQ ID NO 9
<211> LENGTH: 1239
<212> TYPE: DNA
<213> ORGANISM: Artificial Sequence
<220> FEATURE:
<223> OTHER INFORMATION: Description of Artificial Sequence: Synthetic
      ps1181 Fc:TNFalpha polynucleotide
<220> FEATURE:
<221> NAME/KEY: CDS

<222> LOCATION: (1)..(1236)

<400> SEQUENCE: 9

```
atg gct atc atc tac ctc atc ctc ctg ttc acc gct gtg cgg ggc ctc       48
Met Ala Ile Ile Tyr Leu Ile Leu Leu Phe Thr Ala Val Arg Gly Leu
1               5                   10                  15

gac aaa act cac aca tgc cca ccg tgc cca gca cct gaa ctc ctg ggg       96
Asp Lys Thr His Thr Cys Pro Pro Cys Pro Ala Pro Glu Leu Leu Gly
            20                  25                  30

gga ccg tca gtc ttc ctc ttc ccc cca aaa ccc aag gac acc ctc atg      144
Gly Pro Ser Val Phe Leu Phe Pro Pro Lys Pro Lys Asp Thr Leu Met
        35                  40                  45

atc tcc cgg acc cct gag gtc aca tgc gtg gtg gtg gac gtg agc cac      192
Ile Ser Arg Thr Pro Glu Val Thr Cys Val Val Val Asp Val Ser His
    50                  55                  60

gaa gac cct gag gtc aag ttc aac tgg tac gtg gac ggc gtg gag gtg      240
Glu Asp Pro Glu Val Lys Phe Asn Trp Tyr Val Asp Gly Val Glu Val
65                  70                  75                  80

cat aat gcc aag aca aag ccg cgg gag gag cag tac aac agc acg tac      288
His Asn Ala Lys Thr Lys Pro Arg Glu Glu Gln Tyr Asn Ser Thr Tyr
                85                  90                  95

cgt gtg gtc agc gtc ctc acc gtc ctg cac cag gac tgg ctg aat ggc      336
Arg Val Val Ser Val Leu Thr Val Leu His Gln Asp Trp Leu Asn Gly
            100                 105                 110

aag gag tac aag tgc aag gtc tcc aac aaa gcc ctc cca gcc ccc atc      384
Lys Glu Tyr Lys Cys Lys Val Ser Asn Lys Ala Leu Pro Ala Pro Ile
        115                 120                 125

gag aaa acc atc tcc aaa gcc aaa ggg cag ccc cga gaa cca cag gtg      432
Glu Lys Thr Ile Ser Lys Ala Lys Gly Gln Pro Arg Glu Pro Gln Val
    130                 135                 140

tac acc ctg ccc cca tcc cgg gat gag ctg acc aag aac cag gtc agc      480
Tyr Thr Leu Pro Pro Ser Arg Asp Glu Leu Thr Lys Asn Gln Val Ser
145                 150                 155                 160

ctg acc tgc ctg gtc aaa ggc ttc tat ccc agc gac atc gcc gtg gag      528
Leu Thr Cys Leu Val Lys Gly Phe Tyr Pro Ser Asp Ile Ala Val Glu
                165                 170                 175

tgg gag agc aat ggg cag ccg gag aac aac tac aag acc acg cct ccc      576
Trp Glu Ser Asn Gly Gln Pro Glu Asn Asn Tyr Lys Thr Thr Pro Pro
            180                 185                 190

gtg ttg gac tcc gac ggc tcc ttc ttc ctc tac agc aag ctc acc gtg      624
Val Leu Asp Ser Asp Gly Ser Phe Phe Leu Tyr Ser Lys Leu Thr Val
        195                 200                 205

gac aag agc agg tgg cag cag ggg aac gtc ttc tca tgc tcc gtg atg      672
Asp Lys Ser Arg Trp Gln Gln Gly Asn Val Phe Ser Cys Ser Val Met
    210                 215                 220

cat gag gct ctg cac aac cac tac acg cag aag agc ctc tcc ctg tct      720
His Glu Ala Leu His Asn His Tyr Thr Gln Lys Ser Leu Ser Leu Ser
225                 230                 235                 240

ccg ggt aaa aga tct ccg cag ccg cag ccg aaa ccg cag ccg aaa ccg      768
Pro Gly Lys Arg Ser Pro Gln Pro Gln Pro Lys Pro Gln Pro Lys Pro
                245                 250                 255

gaa ccg gaa gga tcc ctg cag agt gac aag cct gta gcc cat gtt gta      816
Glu Pro Glu Gly Ser Leu Gln Ser Asp Lys Pro Val Ala His Val Val
            260                 265                 270

gca aac cct caa gct gag ggg cag ctc cag tgg ctg aac cgc cgg gcc      864
Ala Asn Pro Gln Ala Glu Gly Gln Leu Gln Trp Leu Asn Arg Arg Ala
        275                 280                 285

aat gcc ctc ctg gcc aat ggc gtg gag ctg aga gat aac cag ctg gtg      912
Asn Ala Leu Leu Ala Asn Gly Val Glu Leu Arg Asp Asn Gln Leu Val
    290                 295                 300
```

```
gtg cca tca gag ggc ctg tac ctc atc tac tcc cag gtc ctc ttc aag      960
Val Pro Ser Glu Gly Leu Tyr Leu Ile Tyr Ser Gln Val Leu Phe Lys
305                 310                 315                 320

ggc caa ggc tgc ccc tcc acc cat gtg ctc ctc acc cac acc atc agc     1008
Gly Gln Gly Cys Pro Ser Thr His Val Leu Leu Thr His Thr Ile Ser
                325                 330                 335

cgc atc gcc gtc tcc tac cag acc aag gtc aac ctc ctc tct gcc atc     1056
Arg Ile Ala Val Ser Tyr Gln Thr Lys Val Asn Leu Leu Ser Ala Ile
            340                 345                 350

aag agc ccc tgc cag agg gag acc cca gag ggg gct gag gcc aag ccc     1104
Lys Ser Pro Cys Gln Arg Glu Thr Pro Glu Gly Ala Glu Ala Lys Pro
        355                 360                 365

tgg tat gag ccc atc tat ctg gga ggg gtc ttc cag ctg gag aag ggt     1152
Trp Tyr Glu Pro Ile Tyr Leu Gly Gly Val Phe Gln Leu Glu Lys Gly
    370                 375                 380

gac cga ctc agc gct gag atc aat cgg ccc gac tat ctc gac ttt gcc     1200
Asp Arg Leu Ser Ala Glu Ile Asn Arg Pro Asp Tyr Leu Asp Phe Ala
385                 390                 395                 400

gag tct ggg cag gtc tac ttt ggg atc att gcc ctg tga                 1239
Glu Ser Gly Gln Val Tyr Phe Gly Ile Ile Ala Leu
                405                 410


<210> SEQ ID NO 10
<211> LENGTH: 412
<212> TYPE: PRT
<213> ORGANISM: Artificial Sequence
<220> FEATURE:
<223> OTHER INFORMATION: Description of Artificial Sequence: Synthetic
      construct polypeptide

<400> SEQUENCE: 10

Met Ala Ile Ile Tyr Leu Ile Leu Leu Phe Thr Ala Val Arg Gly Leu
1               5                   10                  15

Asp Lys Thr His Thr Cys Pro Pro Cys Pro Ala Pro Glu Leu Leu Gly
            20                  25                  30

Gly Pro Ser Val Phe Leu Phe Pro Pro Lys Pro Lys Asp Thr Leu Met
        35                  40                  45

Ile Ser Arg Thr Pro Glu Val Thr Cys Val Val Val Asp Val Ser His
    50                  55                  60

Glu Asp Pro Glu Val Lys Phe Asn Trp Tyr Val Asp Gly Val Glu Val
65                  70                  75                  80

His Asn Ala Lys Thr Lys Pro Arg Glu Glu Gln Tyr Asn Ser Thr Tyr
                85                  90                  95

Arg Val Val Ser Val Leu Thr Val Leu His Gln Asp Trp Leu Asn Gly
            100                 105                 110

Lys Glu Tyr Lys Cys Lys Val Ser Asn Lys Ala Leu Pro Ala Pro Ile
        115                 120                 125

Glu Lys Thr Ile Ser Lys Ala Lys Gly Gln Pro Arg Glu Pro Gln Val
    130                 135                 140

Tyr Thr Leu Pro Pro Ser Arg Asp Glu Leu Thr Lys Asn Gln Val Ser
145                 150                 155                 160

Leu Thr Cys Leu Val Lys Gly Phe Tyr Pro Ser Asp Ile Ala Val Glu
                165                 170                 175

Trp Glu Ser Asn Gly Gln Pro Glu Asn Asn Tyr Lys Thr Thr Pro Pro
            180                 185                 190

Val Leu Asp Ser Asp Gly Ser Phe Phe Leu Tyr Ser Lys Leu Thr Val
        195                 200                 205
```

```
Asp Lys Ser Arg Trp Gln Gln Gly Asn Val Phe Ser Cys Ser Val Met
    210                 215                 220

His Glu Ala Leu His Asn His Tyr Thr Gln Lys Ser Leu Ser Leu Ser
225                 230                 235                 240

Pro Gly Lys Arg Ser Pro Gln Pro Gln Pro Lys Pro Gln Pro Lys Pro
                245                 250                 255

Glu Pro Glu Gly Ser Leu Gln Ser Asp Lys Pro Val Ala His Val Val
            260                 265                 270

Ala Asn Pro Gln Ala Glu Gly Gln Leu Gln Trp Leu Asn Arg Arg Ala
        275                 280                 285

Asn Ala Leu Leu Ala Asn Gly Val Glu Leu Arg Asp Asn Gln Leu Val
    290                 295                 300

Val Pro Ser Glu Gly Leu Tyr Leu Ile Tyr Ser Gln Val Leu Phe Lys
305                 310                 315                 320

Gly Gln Gly Cys Pro Ser Thr His Val Leu Leu Thr His Thr Ile Ser
                325                 330                 335

Arg Ile Ala Val Ser Tyr Gln Thr Lys Val Asn Leu Leu Ser Ala Ile
            340                 345                 350

Lys Ser Pro Cys Gln Arg Glu Thr Pro Glu Gly Ala Glu Ala Lys Pro
        355                 360                 365

Trp Tyr Glu Pro Ile Tyr Leu Gly Gly Val Phe Gln Leu Glu Lys Gly
    370                 375                 380

Asp Arg Leu Ser Ala Glu Ile Asn Arg Pro Asp Tyr Leu Asp Phe Ala
385                 390                 395                 400

Glu Ser Gly Gln Val Tyr Phe Gly Ile Ile Ala Leu
                405                 410


<210> SEQ ID NO 11
<211> LENGTH: 1230
<212> TYPE: DNA
<213> ORGANISM: Artificial Sequence
<220> FEATURE:
<223> OTHER INFORMATION: Description of Artificial Sequence: Synthetic
      ps1261 Fc:CD40L polynucleotide
<220> FEATURE:
<221> NAME/KEY: CDS
<222> LOCATION: (1)..(1227)

<400> SEQUENCE: 11

atg gct atc atc tac ctc atc ctc ctg ttc acc gct gtg cgg ggc ctc       48
Met Ala Ile Ile Tyr Leu Ile Leu Leu Phe Thr Ala Val Arg Gly Leu
1               5                   10                  15

gac aaa act cac aca tgc cca ccg tgc cca gca cct gaa ctc ctg ggg       96
Asp Lys Thr His Thr Cys Pro Pro Cys Pro Ala Pro Glu Leu Leu Gly
            20                  25                  30

gga ccg tca gtc ttc ctc ttc ccc cca aaa ccc aag gac acc ctc atg      144
Gly Pro Ser Val Phe Leu Phe Pro Pro Lys Pro Lys Asp Thr Leu Met
        35                  40                  45

atc tcc cgg acc cct gag gtc aca tgc gtg gtg gtg gac gtg agc cac      192
Ile Ser Arg Thr Pro Glu Val Thr Cys Val Val Val Asp Val Ser His
    50                  55                  60

gaa gac cct gag gtc aag ttc aac tgg tac gtg gac ggc gtg gag gtg      240
Glu Asp Pro Glu Val Lys Phe Asn Trp Tyr Val Asp Gly Val Glu Val
65                  70                  75                  80

cat aat gcc aag aca aag ccg cgg gag gag cag tac aac agc acg tac      288
His Asn Ala Lys Thr Lys Pro Arg Glu Glu Gln Tyr Asn Ser Thr Tyr
                85                  90                  95

cgt gtg gtc agc gtc ctc acc gtc ctg cac cag gac tgg ctg aat ggc      336
Arg Val Val Ser Val Leu Thr Val Leu His Gln Asp Trp Leu Asn Gly
```

-continued

```
            100                 105                 110

aag gag tac aag tgc aag gtc tcc aac aaa gcc ctc cca gcc ccc atc      384
Lys Glu Tyr Lys Cys Lys Val Ser Asn Lys Ala Leu Pro Ala Pro Ile
        115                 120                 125

gag aaa acc atc tcc aaa gcc aaa ggg cag ccc cga gaa cca cag gtg      432
Glu Lys Thr Ile Ser Lys Ala Lys Gly Gln Pro Arg Glu Pro Gln Val
    130                 135                 140

tac acc ctg ccc cca tcc cgg gat gag ctg acc aag aac cag gtc agc      480
Tyr Thr Leu Pro Pro Ser Arg Asp Glu Leu Thr Lys Asn Gln Val Ser
145                 150                 155                 160

ctg acc tgc ctg gtc aaa ggc ttc tat ccc agc gac atc gcc gtg gag      528
Leu Thr Cys Leu Val Lys Gly Phe Tyr Pro Ser Asp Ile Ala Val Glu
                165                 170                 175

tgg gag agc aat ggg cag ccg gag aac aac tac aag acc acg cct ccc      576
Trp Glu Ser Asn Gly Gln Pro Glu Asn Asn Tyr Lys Thr Thr Pro Pro
            180                 185                 190

gtg ttg gac tcc gac ggc tcc ttc ttc ctc tac agc aag ctc acc gtg      624
Val Leu Asp Ser Asp Gly Ser Phe Phe Leu Tyr Ser Lys Leu Thr Val
        195                 200                 205

gac aag agc agg tgg cag cag ggg aac gtc ttc tca tgc tcc gtg atg      672
Asp Lys Ser Arg Trp Gln Gln Gly Asn Val Phe Ser Cys Ser Val Met
    210                 215                 220

cat gag gct ctg cac aac cac tac acg cag aag agc ctc tcc ctg tct      720
His Glu Ala Leu His Asn His Tyr Thr Gln Lys Ser Leu Ser Leu Ser
225                 230                 235                 240

ccg ggt aaa aga tct ccg cag ccg cag ccg aaa ccg cag ccg aaa ccg      768
Pro Gly Lys Arg Ser Pro Gln Pro Gln Pro Lys Pro Gln Pro Lys Pro
                245                 250                 255

gaa ccg gaa gga tcc ctg cag ggt gat cag aat cct caa att gcg gca      816
Glu Pro Glu Gly Ser Leu Gln Gly Asp Gln Asn Pro Gln Ile Ala Ala
            260                 265                 270

cat gtc ata agt gag gcc agc agt aaa aca aca tct gtg tta cag tgg      864
His Val Ile Ser Glu Ala Ser Ser Lys Thr Thr Ser Val Leu Gln Trp
        275                 280                 285

gct gaa aaa gga tac tac acc atg agc aac aac ttg gta acc ctg gaa      912
Ala Glu Lys Gly Tyr Tyr Thr Met Ser Asn Asn Leu Val Thr Leu Glu
    290                 295                 300

aat ggg aaa cag ctg acc gtt aaa aga caa gga ctc tat tat atc tat      960
Asn Gly Lys Gln Leu Thr Val Lys Arg Gln Gly Leu Tyr Tyr Ile Tyr
305                 310                 315                 320

gcc caa gtc acc ttc tgt tcc aat cgg gaa gct tcg agt caa gct cca     1008
Ala Gln Val Thr Phe Cys Ser Asn Arg Glu Ala Ser Ser Gln Ala Pro
                325                 330                 335

ttt ata gcc agc ctc tgc cta aag tcc ccc ggt aga ttc gag aga atc     1056
Phe Ile Ala Ser Leu Cys Leu Lys Ser Pro Gly Arg Phe Glu Arg Ile
            340                 345                 350

tta ctc aga gct gca aat acc cac agt tcc gcc aaa cct tgc ggg caa     1104
Leu Leu Arg Ala Ala Asn Thr His Ser Ser Ala Lys Pro Cys Gly Gln
        355                 360                 365

caa tcc att cac ttg gga gga gta ttt gaa ttg caa cca ggt gct tcg     1152
Gln Ser Ile His Leu Gly Gly Val Phe Glu Leu Gln Pro Gly Ala Ser
    370                 375                 380

gtg ttt gtc aat gtg act gat cca agc caa gtg agc cat ggc act ggc     1200
Val Phe Val Asn Val Thr Asp Pro Ser Gln Val Ser His Gly Thr Gly
385                 390                 395                 400

ttc acg tcc ttt ggc tta ctc aaa ctc tga                             1230
Phe Thr Ser Phe Gly Leu Leu Lys Leu
                405
```

<210> SEQ ID NO 12
<211> LENGTH: 409
<212> TYPE: PRT
<213> ORGANISM: Artificial Sequence
<220> FEATURE:
<223> OTHER INFORMATION: Description of Artificial Sequence: Synthetic construct polypeptide

<400> SEQUENCE: 12

```
Met Ala Ile Ile Tyr Leu Ile Leu Leu Phe Thr Ala Val Arg Gly Leu
1               5                   10                  15

Asp Lys Thr His Thr Cys Pro Pro Cys Pro Ala Pro Glu Leu Leu Gly
            20                  25                  30

Gly Pro Ser Val Phe Leu Phe Pro Pro Lys Pro Lys Asp Thr Leu Met
        35                  40                  45

Ile Ser Arg Thr Pro Glu Val Thr Cys Val Val Val Asp Val Ser His
    50                  55                  60

Glu Asp Pro Glu Val Lys Phe Asn Trp Tyr Val Asp Gly Val Glu Val
65                  70                  75                  80

His Asn Ala Lys Thr Lys Pro Arg Glu Glu Gln Tyr Asn Ser Thr Tyr
                85                  90                  95

Arg Val Val Ser Val Leu Thr Val Leu His Gln Asp Trp Leu Asn Gly
            100                 105                 110

Lys Glu Tyr Lys Cys Lys Val Ser Asn Lys Ala Leu Pro Ala Pro Ile
        115                 120                 125

Glu Lys Thr Ile Ser Lys Ala Lys Gly Gln Pro Arg Glu Pro Gln Val
    130                 135                 140

Tyr Thr Leu Pro Pro Ser Arg Asp Glu Leu Thr Lys Asn Gln Val Ser
145                 150                 155                 160

Leu Thr Cys Leu Val Lys Gly Phe Tyr Pro Ser Asp Ile Ala Val Glu
                165                 170                 175

Trp Glu Ser Asn Gly Gln Pro Glu Asn Asn Tyr Lys Thr Thr Pro Pro
            180                 185                 190

Val Leu Asp Ser Asp Gly Ser Phe Phe Leu Tyr Ser Lys Leu Thr Val
        195                 200                 205

Asp Lys Ser Arg Trp Gln Gln Gly Asn Val Phe Ser Cys Ser Val Met
    210                 215                 220

His Glu Ala Leu His Asn His Tyr Thr Gln Lys Ser Leu Ser Leu Ser
225                 230                 235                 240

Pro Gly Lys Arg Ser Pro Gln Pro Gln Pro Lys Pro Gln Pro Lys Pro
                245                 250                 255

Glu Pro Glu Gly Ser Leu Gln Gly Asp Gln Asn Pro Gln Ile Ala Ala
            260                 265                 270

His Val Ile Ser Glu Ala Ser Ser Lys Thr Thr Ser Val Leu Gln Trp
        275                 280                 285

Ala Glu Lys Gly Tyr Tyr Thr Met Ser Asn Asn Leu Val Thr Leu Glu
    290                 295                 300

Asn Gly Lys Gln Leu Thr Val Lys Arg Gln Gly Leu Tyr Tyr Ile Tyr
305                 310                 315                 320

Ala Gln Val Thr Phe Cys Ser Asn Arg Glu Ala Ser Ser Gln Ala Pro
                325                 330                 335

Phe Ile Ala Ser Leu Cys Leu Lys Ser Pro Gly Arg Phe Glu Arg Ile
            340                 345                 350

Leu Leu Arg Ala Ala Asn Thr His Ser Ser Ala Lys Pro Cys Gly Gln
        355                 360                 365
```

-continued

```
Gln Ser Ile His Leu Gly Gly Val Phe Glu Leu Gln Pro Gly Ala Ser
    370                 375                 380

Val Phe Val Asn Val Thr Asp Pro Ser Gln Val Ser His Gly Thr Gly
385                 390                 395                 400

Phe Thr Ser Phe Gly Leu Leu Lys Leu
                405


<210> SEQ ID NO 13
<211> LENGTH: 1353
<212> TYPE: DNA
<213> ORGANISM: Artificial Sequence
<220> FEATURE:
<223> OTHER INFORMATION: Description of Artificial Sequence: Synthetic
      ps1220 Fc:TRAIL polynucleotide
<220> FEATURE:
<221> NAME/KEY: CDS
<222> LOCATION: (1)..(1350)

<400> SEQUENCE: 13

atg gct atc atc tac ctc atc ctc ctg ttc acc gct gtg cgg ggc ctc       48
Met Ala Ile Ile Tyr Leu Ile Leu Leu Phe Thr Ala Val Arg Gly Leu
1               5                   10                  15

gac aaa act cac aca tgc cca ccg tgc cca gca cct gaa ctc ctg ggg       96
Asp Lys Thr His Thr Cys Pro Pro Cys Pro Ala Pro Glu Leu Leu Gly
            20                  25                  30

gga ccg tca gtc ttc ctc ttc ccc cca aaa ccc aag gac acc ctc atg      144
Gly Pro Ser Val Phe Leu Phe Pro Pro Lys Pro Lys Asp Thr Leu Met
        35                  40                  45

atc tcc cgg acc cct gag gtc aca tgc gtg gtg gtg gac gtg agc cac      192
Ile Ser Arg Thr Pro Glu Val Thr Cys Val Val Val Asp Val Ser His
    50                  55                  60

gaa gac cct gag gtc aag ttc aac tgg tac gtg gac ggc gtg gag gtg      240
Glu Asp Pro Glu Val Lys Phe Asn Trp Tyr Val Asp Gly Val Glu Val
65                  70                  75                  80

cat aat gcc aag aca aag ccg cgg gag gag cag tac aac agc acg tac      288
His Asn Ala Lys Thr Lys Pro Arg Glu Glu Gln Tyr Asn Ser Thr Tyr
                85                  90                  95

cgt gtg gtc agc gtc ctc acc gtc ctg cac cag gac tgg ctg aat ggc      336
Arg Val Val Ser Val Leu Thr Val Leu His Gln Asp Trp Leu Asn Gly
            100                 105                 110

aag gag tac aag tgc aag gtc tcc aac aaa gcc ctc cca gcc ccc atc      384
Lys Glu Tyr Lys Cys Lys Val Ser Asn Lys Ala Leu Pro Ala Pro Ile
        115                 120                 125

gag aaa acc atc tcc aaa gcc aaa ggg cag ccc cga gaa cca cag gtg      432
Glu Lys Thr Ile Ser Lys Ala Lys Gly Gln Pro Arg Glu Pro Gln Val
    130                 135                 140

tac acc ctg ccc cca tcc cgg gat gag ctg acc aag aac cag gtc agc      480
Tyr Thr Leu Pro Pro Ser Arg Asp Glu Leu Thr Lys Asn Gln Val Ser
145                 150                 155                 160

ctg acc tgc ctg gtc aaa ggc ttc tat ccc agc gac atc gcc gtg gag      528
Leu Thr Cys Leu Val Lys Gly Phe Tyr Pro Ser Asp Ile Ala Val Glu
                165                 170                 175

tgg gag agc aat ggg cag ccg gag aac aac tac aag acc acg cct ccc      576
Trp Glu Ser Asn Gly Gln Pro Glu Asn Asn Tyr Lys Thr Thr Pro Pro
            180                 185                 190

gtg ttg gac tcc gac ggc tcc ttc ttc ctc tac agc aag ctc acc gtg      624
Val Leu Asp Ser Asp Gly Ser Phe Phe Leu Tyr Ser Lys Leu Thr Val
        195                 200                 205

gac aag agc agg tgg cag cag ggg aac gtc ttc tca tgc tcc gtg atg      672
Asp Lys Ser Arg Trp Gln Gln Gly Asn Val Phe Ser Cys Ser Val Met
    210                 215                 220
```

-continued

```
cat gag gct ctg cac aac cac tac acg cag aag agc ctc tcc ctg tct      720
His Glu Ala Leu His Asn His Tyr Thr Gln Lys Ser Leu Ser Leu Ser
225                 230                 235                 240

ccg ggt aaa aga tct ccg cag ccg cag ccg aaa ccg cag ccg aaa ccg      768
Pro Gly Lys Arg Ser Pro Gln Pro Gln Pro Lys Pro Gln Pro Lys Pro
                245                 250                 255

gaa ccg gaa gga tcc ctg cag acc tct gag gaa acc att tct aca gtt      816
Glu Pro Glu Gly Ser Leu Gln Thr Ser Glu Glu Thr Ile Ser Thr Val
            260                 265                 270

caa gaa aag caa caa aat att tct ccc cta gtg aga gaa aga ggt cct      864
Gln Glu Lys Gln Gln Asn Ile Ser Pro Leu Val Arg Glu Arg Gly Pro
        275                 280                 285

cag aga gta gca gct cac ata act ggg acc aga gga aga agc aac aca      912
Gln Arg Val Ala Ala His Ile Thr Gly Thr Arg Gly Arg Ser Asn Thr
    290                 295                 300

ttg tct tct cca aac tcc aag aat gaa aag gct ctg ggc cgc aaa ata      960
Leu Ser Ser Pro Asn Ser Lys Asn Glu Lys Ala Leu Gly Arg Lys Ile
305                 310                 315                 320

aac tcc tgg gaa tca tca agg agt ggg cat tca ttc ctg agc aac ttg     1008
Asn Ser Trp Glu Ser Ser Arg Ser Gly His Ser Phe Leu Ser Asn Leu
                325                 330                 335

cac ttg agg aat ggt gaa ctg gtc atc cat gaa aaa ggg ttt tac tac     1056
His Leu Arg Asn Gly Glu Leu Val Ile His Glu Lys Gly Phe Tyr Tyr
            340                 345                 350

atc tat tcc caa aca tac ttt cga ttt cag gag gaa ata aaa gaa aac     1104
Ile Tyr Ser Gln Thr Tyr Phe Arg Phe Gln Glu Glu Ile Lys Glu Asn
        355                 360                 365

aca aag aac gac aaa caa atg gtc caa tat att tac aaa tac aca agt     1152
Thr Lys Asn Asp Lys Gln Met Val Gln Tyr Ile Tyr Lys Tyr Thr Ser
    370                 375                 380

tat cct gac cct ata ttg ttg atg aaa agt gct aga aat agt tgt tgg     1200
Tyr Pro Asp Pro Ile Leu Leu Met Lys Ser Ala Arg Asn Ser Cys Trp
385                 390                 395                 400

tct aaa gat gca gaa tat gga ctc tat tcc atc tat caa ggg gga ata     1248
Ser Lys Asp Ala Glu Tyr Gly Leu Tyr Ser Ile Tyr Gln Gly Gly Ile
                405                 410                 415

ttt gag ctt aag gaa aat gac aga att ttt gtt tct gta aca aat gag     1296
Phe Glu Leu Lys Glu Asn Asp Arg Ile Phe Val Ser Val Thr Asn Glu
            420                 425                 430

cac ttg ata gac atg gac cat gaa gcc agt ttt ttc ggg gcc ttt tta     1344
His Leu Ile Asp Met Asp His Glu Ala Ser Phe Phe Gly Ala Phe Leu
        435                 440                 445

gtt ggc taa                                                         1353
Val Gly
    450
```

<210> SEQ ID NO 14
<211> LENGTH: 450
<212> TYPE: PRT
<213> ORGANISM: Artificial Sequence
<220> FEATURE:
<223> OTHER INFORMATION: Description of Artificial Sequence: Synthetic construct polypeptide

<400> SEQUENCE: 14

```
Met Ala Ile Ile Tyr Leu Ile Leu Leu Phe Thr Ala Val Arg Gly Leu
1               5                   10                  15

Asp Lys Thr His Thr Cys Pro Pro Cys Pro Ala Pro Glu Leu Leu Gly
            20                  25                  30

Gly Pro Ser Val Phe Leu Phe Pro Pro Lys Pro Lys Asp Thr Leu Met
        35                  40                  45
```

```
Ile Ser Arg Thr Pro Glu Val Thr Cys Val Val Val Asp Val Ser His
    50                  55                  60

Glu Asp Pro Glu Val Lys Phe Asn Trp Tyr Val Asp Gly Val Glu Val
65                  70                  75                  80

His Asn Ala Lys Thr Lys Pro Arg Glu Glu Gln Tyr Asn Ser Thr Tyr
                85                  90                  95

Arg Val Val Ser Val Leu Thr Val Leu His Gln Asp Trp Leu Asn Gly
            100                 105                 110

Lys Glu Tyr Lys Cys Lys Val Ser Asn Lys Ala Leu Pro Ala Pro Ile
        115                 120                 125

Glu Lys Thr Ile Ser Lys Ala Lys Gly Gln Pro Arg Glu Pro Gln Val
    130                 135                 140

Tyr Thr Leu Pro Pro Ser Arg Asp Glu Leu Thr Lys Asn Gln Val Ser
145                 150                 155                 160

Leu Thr Cys Leu Val Lys Gly Phe Tyr Pro Ser Asp Ile Ala Val Glu
                165                 170                 175

Trp Glu Ser Asn Gly Gln Pro Glu Asn Asn Tyr Lys Thr Thr Pro Pro
            180                 185                 190

Val Leu Asp Ser Asp Gly Ser Phe Phe Leu Tyr Ser Lys Leu Thr Val
        195                 200                 205

Asp Lys Ser Arg Trp Gln Gln Gly Asn Val Phe Ser Cys Ser Val Met
    210                 215                 220

His Glu Ala Leu His Asn His Tyr Thr Gln Lys Ser Leu Ser Leu Ser
225                 230                 235                 240

Pro Gly Lys Arg Ser Pro Gln Pro Gln Pro Lys Pro Gln Pro Lys Pro
                245                 250                 255

Glu Pro Glu Gly Ser Leu Gln Thr Ser Glu Glu Thr Ile Ser Thr Val
            260                 265                 270

Gln Glu Lys Gln Gln Asn Ile Ser Pro Leu Val Arg Glu Arg Gly Pro
        275                 280                 285

Gln Arg Val Ala Ala His Ile Thr Gly Thr Arg Gly Arg Ser Asn Thr
    290                 295                 300

Leu Ser Ser Pro Asn Ser Lys Asn Glu Lys Ala Leu Gly Arg Lys Ile
305                 310                 315                 320

Asn Ser Trp Glu Ser Ser Arg Ser Gly His Ser Phe Leu Ser Asn Leu
                325                 330                 335

His Leu Arg Asn Gly Glu Leu Val Ile His Glu Lys Gly Phe Tyr Tyr
            340                 345                 350

Ile Tyr Ser Gln Thr Tyr Phe Arg Phe Gln Glu Glu Ile Lys Glu Asn
        355                 360                 365

Thr Lys Asn Asp Lys Gln Met Val Gln Tyr Ile Tyr Lys Tyr Thr Ser
    370                 375                 380

Tyr Pro Asp Pro Ile Leu Leu Met Lys Ser Ala Arg Asn Ser Cys Trp
385                 390                 395                 400

Ser Lys Asp Ala Glu Tyr Gly Leu Tyr Ser Ile Tyr Gln Gly Gly Ile
                405                 410                 415

Phe Glu Leu Lys Glu Asn Asp Arg Ile Phe Val Ser Val Thr Asn Glu
            420                 425                 430

His Leu Ile Asp Met Asp His Glu Ala Ser Phe Phe Gly Ala Phe Leu
        435                 440                 445

Val Gly
    450
```

<210> SEQ ID NO 15
<211> LENGTH: 1269
<212> TYPE: DNA
<213> ORGANISM: Artificial Sequence
<220> FEATURE:
<223> OTHER INFORMATION: Description of Artificial Sequence: Synthetic
ps1196 Fc-PS:BAFF polynucleotide
<220> FEATURE:
<221> NAME/KEY: CDS
<222> LOCATION: (1)..(1266)

<400> SEQUENCE: 15

```
atg gct atc atc tac ctc atc ctc ctg ttc acc gct gtg cgg ggc ctc       48
Met Ala Ile Ile Tyr Leu Ile Leu Leu Phe Thr Ala Val Arg Gly Leu
1               5                   10                  15

gac aaa act cac aca tgc cca ccg tgc cca gca cct gaa ctc ctg ggg       96
Asp Lys Thr His Thr Cys Pro Pro Cys Pro Ala Pro Glu Leu Leu Gly
            20                  25                  30

gga ccg tca gtc ttc ctc ttc ccc cca aaa ccc aag gac acc ctc atg      144
Gly Pro Ser Val Phe Leu Phe Pro Pro Lys Pro Lys Asp Thr Leu Met
        35                  40                  45

atc tcc cgg acc cct gag gtc aca tgc gtg gtg gtg gac gtg agc cac      192
Ile Ser Arg Thr Pro Glu Val Thr Cys Val Val Val Asp Val Ser His
    50                  55                  60

gaa gac cct gag gtc aag ttc aac tgg tac gtg gac ggc gtg gag gtg      240
Glu Asp Pro Glu Val Lys Phe Asn Trp Tyr Val Asp Gly Val Glu Val
65                  70                  75                  80

cat aat gcc aag aca aag ccg cgg gag gag cag tac aac agc acg tac      288
His Asn Ala Lys Thr Lys Pro Arg Glu Glu Gln Tyr Asn Ser Thr Tyr
                85                  90                  95

cgt gtg gtc agc gtc ctc acc gtc ctg cac cag gac tgg ctg aat ggc      336
Arg Val Val Ser Val Leu Thr Val Leu His Gln Asp Trp Leu Asn Gly
            100                 105                 110

aag gag tac aag tgc aag gtc tcc aac aaa gcc ctc cca gcc ccc atc      384
Lys Glu Tyr Lys Cys Lys Val Ser Asn Lys Ala Leu Pro Ala Pro Ile
        115                 120                 125

gag aaa acc atc tcc aaa gcc aaa ggg cag ccc cga gaa cca cag gtg      432
Glu Lys Thr Ile Ser Lys Ala Lys Gly Gln Pro Arg Glu Pro Gln Val
    130                 135                 140

tac acc ctg ccc cca tcc cgg gat gag ctg acc aag aac cag gtc agc      480
Tyr Thr Leu Pro Pro Ser Arg Asp Glu Leu Thr Lys Asn Gln Val Ser
145                 150                 155                 160

ctg acc tgc ctg gtc aaa ggc ttc tat ccc agc gac atc gcc gtg gag      528
Leu Thr Cys Leu Val Lys Gly Phe Tyr Pro Ser Asp Ile Ala Val Glu
                165                 170                 175

tgg gag agc aat ggg cag ccg gag aac aac tac aag acc acg cct ccc      576
Trp Glu Ser Asn Gly Gln Pro Glu Asn Asn Tyr Lys Thr Thr Pro Pro
            180                 185                 190

gtg ttg gac tcc gac ggc tcc ttc ttc ctc tac agc aag ctc acc gtg      624
Val Leu Asp Ser Asp Gly Ser Phe Phe Leu Tyr Ser Lys Leu Thr Val
        195                 200                 205

gac aag agc agg tgg cag cag ggg aac gtc ttc tca tgc tcc gtg atg      672
Asp Lys Ser Arg Trp Gln Gln Gly Asn Val Phe Ser Cys Ser Val Met
    210                 215                 220

cat gag gct ctg cac aac cac tac acg cag aag agc ctc tcc ctg tct      720
His Glu Ala Leu His Asn His Tyr Thr Gln Lys Ser Leu Ser Leu Ser
225                 230                 235                 240

ccg ggt aaa aga tct ccg cag ccg cag ccg aaa ccg cag ccg aaa ccg      768
Pro Gly Lys Arg Ser Pro Gln Pro Gln Pro Lys Pro Gln Pro Lys Pro
                245                 250                 255

gaa ccg gaa gga tct ctg gag gtg ctg ttc cag ggg ccc gga tcc ctg      816
```

```
Glu Pro Glu Gly Ser Leu Glu Val Leu Phe Gln Gly Pro Gly Ser Leu
            260                 265                 270

cag ggt cca gaa gaa aca gtc act caa gac tgc ttg caa ctg att gca      864
Gln Gly Pro Glu Glu Thr Val Thr Gln Asp Cys Leu Gln Leu Ile Ala
        275                 280                 285

gac agt gaa aca cca act ata caa aaa gga tct tac aca ttt gtt cca      912
Asp Ser Glu Thr Pro Thr Ile Gln Lys Gly Ser Tyr Thr Phe Val Pro
    290                 295                 300

tgg ctt ctc agc ttt aaa agg gga agt gcc cta gaa gaa aaa gag aat      960
Trp Leu Leu Ser Phe Lys Arg Gly Ser Ala Leu Glu Glu Lys Glu Asn
305                 310                 315                 320

aaa ata ttg gtc aaa gaa act ggt tac ttt ttt ata tat ggt cag gtt     1008
Lys Ile Leu Val Lys Glu Thr Gly Tyr Phe Phe Ile Tyr Gly Gln Val
                325                 330                 335

tta tat act gat aag acc tac gcc atg gga cat cta att cag agg aag     1056
Leu Tyr Thr Asp Lys Thr Tyr Ala Met Gly His Leu Ile Gln Arg Lys
            340                 345                 350

aag gtc cat gtc ttt ggg gat gaa ttg agt ctg gtg act ttg ttt cga     1104
Lys Val His Val Phe Gly Asp Glu Leu Ser Leu Val Thr Leu Phe Arg
        355                 360                 365

tgt att caa aat atg cct gaa aca cta ccc aat aat tcc tgc tat tca     1152
Cys Ile Gln Asn Met Pro Glu Thr Leu Pro Asn Asn Ser Cys Tyr Ser
    370                 375                 380

gct ggc att gca aaa ctg gaa gaa gga gat gaa ctc caa ctt gca ata     1200
Ala Gly Ile Ala Lys Leu Glu Glu Gly Asp Glu Leu Gln Leu Ala Ile
385                 390                 395                 400

cca aga gaa aat gca caa ata tca ctg gat gga gat gtc aca ttt ttt     1248
Pro Arg Glu Asn Ala Gln Ile Ser Leu Asp Gly Asp Val Thr Phe Phe
                405                 410                 415

ggt gca ttg aaa ctg ctg tga                                         1269
Gly Ala Leu Lys Leu Leu
            420


<210> SEQ ID NO 16
<211> LENGTH: 422
<212> TYPE: PRT
<213> ORGANISM: Artificial Sequence
<220> FEATURE:
<223> OTHER INFORMATION: Description of Artificial Sequence: Synthetic
      construct polypeptide

<400> SEQUENCE: 16

Met Ala Ile Ile Tyr Leu Ile Leu Leu Phe Thr Ala Val Arg Gly Leu
1               5                   10                  15

Asp Lys Thr His Thr Cys Pro Pro Cys Pro Ala Pro Glu Leu Leu Gly
            20                  25                  30

Gly Pro Ser Val Phe Leu Phe Pro Pro Lys Pro Lys Asp Thr Leu Met
        35                  40                  45

Ile Ser Arg Thr Pro Glu Val Thr Cys Val Val Val Asp Val Ser His
    50                  55                  60

Glu Asp Pro Glu Val Lys Phe Asn Trp Tyr Val Asp Gly Val Glu Val
65                  70                  75                  80

His Asn Ala Lys Thr Lys Pro Arg Glu Glu Gln Tyr Asn Ser Thr Tyr
                85                  90                  95

Arg Val Val Ser Val Leu Thr Val Leu His Gln Asp Trp Leu Asn Gly
            100                 105                 110

Lys Glu Tyr Lys Cys Lys Val Ser Asn Lys Ala Leu Pro Ala Pro Ile
        115                 120                 125

Glu Lys Thr Ile Ser Lys Ala Lys Gly Gln Pro Arg Glu Pro Gln Val
```

```
    130                 135                 140

Tyr Thr Leu Pro Pro Ser Arg Asp Glu Leu Thr Lys Asn Gln Val Ser
145                 150                 155                 160

Leu Thr Cys Leu Val Lys Gly Phe Tyr Pro Ser Asp Ile Ala Val Glu
                165                 170                 175

Trp Glu Ser Asn Gly Gln Pro Glu Asn Asn Tyr Lys Thr Thr Pro Pro
            180                 185                 190

Val Leu Asp Ser Asp Gly Ser Phe Phe Leu Tyr Ser Lys Leu Thr Val
        195                 200                 205

Asp Lys Ser Arg Trp Gln Gln Gly Asn Val Phe Ser Cys Ser Val Met
    210                 215                 220

His Glu Ala Leu His Asn His Tyr Thr Gln Lys Ser Leu Ser Leu Ser
225                 230                 235                 240

Pro Gly Lys Arg Ser Pro Gln Pro Gln Pro Lys Pro Gln Pro Lys Pro
                245                 250                 255

Glu Pro Glu Gly Ser Leu Glu Val Leu Phe Gln Gly Pro Gly Ser Leu
            260                 265                 270

Gln Gly Pro Glu Glu Thr Val Thr Gln Asp Cys Leu Gln Leu Ile Ala
        275                 280                 285

Asp Ser Glu Thr Pro Thr Ile Gln Lys Gly Ser Tyr Thr Phe Val Pro
    290                 295                 300

Trp Leu Leu Ser Phe Lys Arg Gly Ser Ala Leu Glu Glu Lys Glu Asn
305                 310                 315                 320

Lys Ile Leu Val Lys Glu Thr Gly Tyr Phe Phe Ile Tyr Gly Gln Val
                325                 330                 335

Leu Tyr Thr Asp Lys Thr Tyr Ala Met Gly His Leu Ile Gln Arg Lys
            340                 345                 350

Lys Val His Val Phe Gly Asp Glu Leu Ser Leu Val Thr Leu Phe Arg
        355                 360                 365

Cys Ile Gln Asn Met Pro Glu Thr Leu Pro Asn Asn Ser Cys Tyr Ser
    370                 375                 380

Ala Gly Ile Ala Lys Leu Glu Glu Gly Asp Glu Leu Gln Leu Ala Ile
385                 390                 395                 400

Pro Arg Glu Asn Ala Gln Ile Ser Leu Asp Gly Asp Val Thr Phe Phe
                405                 410                 415

Gly Ala Leu Lys Leu Leu
            420


<210> SEQ ID NO 17
<211> LENGTH: 1230
<212> TYPE: DNA
<213> ORGANISM: Artificial Sequence
<220> FEATURE:
<223> OTHER INFORMATION: Description of Artificial Sequence: Synthetic
      ps1307 Fc-PS:APRIL polynucleotide
<220> FEATURE:
<221> NAME/KEY: CDS
<222> LOCATION: (1)..(1227)

<400> SEQUENCE: 17

atg gct atc atc tac ctc atc ctc ctg ttc acc gct gtg cgg ggc ctc       48
Met Ala Ile Ile Tyr Leu Ile Leu Leu Phe Thr Ala Val Arg Gly Leu
1               5                   10                  15

gac aaa act cac aca tgc cca ccg tgc cca gca cct gaa ctc ctg ggg       96
Asp Lys Thr His Thr Cys Pro Pro Cys Pro Ala Pro Glu Leu Leu Gly
            20                  25                  30

gga ccg tca gtc ttc ctc ttc ccc cca aaa ccc aag gac acc ctc atg      144
```

-continued

```
Gly Pro Ser Val Phe Leu Phe Pro Pro Lys Pro Lys Asp Thr Leu Met
        35                  40                  45

atc tcc cgg acc cct gag gtc aca tgc gtg gtg gtg gac gtg agc cac       192
Ile Ser Arg Thr Pro Glu Val Thr Cys Val Val Val Asp Val Ser His
    50                  55                  60

gaa gac cct gag gtc aag ttc aac tgg tac gtg gac ggc gtg gag gtg       240
Glu Asp Pro Glu Val Lys Phe Asn Trp Tyr Val Asp Gly Val Glu Val
65                  70                  75                  80

cat aat gcc aag aca aag ccg cgg gag gag cag tac aac agc acg tac       288
His Asn Ala Lys Thr Lys Pro Arg Glu Glu Gln Tyr Asn Ser Thr Tyr
                85                  90                  95

cgt gtg gtc agc gtc ctc acc gtc ctg cac cag gac tgg ctg aat ggc       336
Arg Val Val Ser Val Leu Thr Val Leu His Gln Asp Trp Leu Asn Gly
            100                 105                 110

aag gag tac aag tgc aag gtc tcc aac aaa gcc ctc cca gcc ccc atc       384
Lys Glu Tyr Lys Cys Lys Val Ser Asn Lys Ala Leu Pro Ala Pro Ile
        115                 120                 125

gag aaa acc atc tcc aaa gcc aaa ggg cag ccc cga gaa cca cag gtg       432
Glu Lys Thr Ile Ser Lys Ala Lys Gly Gln Pro Arg Glu Pro Gln Val
    130                 135                 140

tac acc ctg ccc cca tcc cgg gat gag ctg acc aag aac cag gtc agc       480
Tyr Thr Leu Pro Pro Ser Arg Asp Glu Leu Thr Lys Asn Gln Val Ser
145                 150                 155                 160

ctg acc tgc ctg gtc aaa ggc ttc tat ccc agc gac atc gcc gtg gag       528
Leu Thr Cys Leu Val Lys Gly Phe Tyr Pro Ser Asp Ile Ala Val Glu
                165                 170                 175

tgg gag agc aat ggg cag ccg gag aac aac tac aag acc acg cct ccc       576
Trp Glu Ser Asn Gly Gln Pro Glu Asn Asn Tyr Lys Thr Thr Pro Pro
            180                 185                 190

gtg ttg gac tcc gac ggc tcc ttc ttc ctc tac agc aag ctc acc gtg       624
Val Leu Asp Ser Asp Gly Ser Phe Phe Leu Tyr Ser Lys Leu Thr Val
        195                 200                 205

gac aag agc agg tgg cag cag ggg aac gtc ttc tca tgc tcc gtg atg       672
Asp Lys Ser Arg Trp Gln Gln Gly Asn Val Phe Ser Cys Ser Val Met
    210                 215                 220

cat gag gct ctg cac aac cac tac acg cag aag agc ctc tcc ctg tct       720
His Glu Ala Leu His Asn His Tyr Thr Gln Lys Ser Leu Ser Leu Ser
225                 230                 235                 240

ccg ggt aaa aga tct ccg cag ccg cag ccg aaa ccg cag ccg aaa ccg       768
Pro Gly Lys Arg Ser Pro Gln Pro Gln Pro Lys Pro Gln Pro Lys Pro
                245                 250                 255

gaa ccg gaa gga tct ctg gag gtg ctg ttc cag ggg ccc gga tcc ctg       816
Glu Pro Glu Gly Ser Leu Glu Val Leu Phe Gln Gly Pro Gly Ser Leu
            260                 265                 270

cag cac tct gtc ctg cac ctg gtt ccc att aac gcc acc tcc aag gat       864
Gln His Ser Val Leu His Leu Val Pro Ile Asn Ala Thr Ser Lys Asp
        275                 280                 285

gac tcc gat gtg aca gag gtg atg tgg caa cca gct ctt agg cgt ggg       912
Asp Ser Asp Val Thr Glu Val Met Trp Gln Pro Ala Leu Arg Arg Gly
    290                 295                 300

aga ggc cta cag gcc caa gga tat ggt gtc cga atc cag gat gct gga       960
Arg Gly Leu Gln Ala Gln Gly Tyr Gly Val Arg Ile Gln Asp Ala Gly
305                 310                 315                 320

gtt tat ctg ctg tat agc cag gtc ctg ttt caa gac gtg act ttc acc      1008
Val Tyr Leu Leu Tyr Ser Gln Val Leu Phe Gln Asp Val Thr Phe Thr
                325                 330                 335

atg ggt cag gtg gtg tct cga gaa ggc caa gga agg cag gag act cta      1056
Met Gly Gln Val Val Ser Arg Glu Gly Gln Gly Arg Gln Glu Thr Leu
            340                 345                 350
```

-continued

```
ttc cga tgt ata aga agt atg ccc tcc cac ccg gac cgg gcc tac aac     1104
Phe Arg Cys Ile Arg Ser Met Pro Ser His Pro Asp Arg Ala Tyr Asn
        355                 360                 365

agc tgc tat agc gca ggt gtc ttc cat tta cac caa ggg gat att ctg     1152
Ser Cys Tyr Ser Ala Gly Val Phe His Leu His Gln Gly Asp Ile Leu
    370                 375                 380

agt gtc ata att ccc cgg gca agg gcg aaa ctt aac ctc tct cca cat     1200
Ser Val Ile Ile Pro Arg Ala Arg Ala Lys Leu Asn Leu Ser Pro His
385                 390                 395                 400

gga acc ttc ctg ggg ttt gtg aaa ctg tga                             1230
Gly Thr Phe Leu Gly Phe Val Lys Leu
                405


<210> SEQ ID NO 18
<211> LENGTH: 409
<212> TYPE: PRT
<213> ORGANISM: Artificial Sequence
<220> FEATURE:
<223> OTHER INFORMATION: Description of Artificial Sequence: Synthetic
      construct polypeptide

<400> SEQUENCE: 18

Met Ala Ile Ile Tyr Leu Ile Leu Leu Phe Thr Ala Val Arg Gly Leu
1               5                   10                  15

Asp Lys Thr His Thr Cys Pro Pro Cys Pro Ala Pro Glu Leu Leu Gly
            20                  25                  30

Gly Pro Ser Val Phe Leu Phe Pro Pro Lys Pro Lys Asp Thr Leu Met
        35                  40                  45

Ile Ser Arg Thr Pro Glu Val Thr Cys Val Val Val Asp Val Ser His
    50                  55                  60

Glu Asp Pro Glu Val Lys Phe Asn Trp Tyr Val Asp Gly Val Glu Val
65                  70                  75                  80

His Asn Ala Lys Thr Lys Pro Arg Glu Glu Gln Tyr Asn Ser Thr Tyr
                85                  90                  95

Arg Val Val Ser Val Leu Thr Val Leu His Gln Asp Trp Leu Asn Gly
            100                 105                 110

Lys Glu Tyr Lys Cys Lys Val Ser Asn Lys Ala Leu Pro Ala Pro Ile
        115                 120                 125

Glu Lys Thr Ile Ser Lys Ala Lys Gly Gln Pro Arg Glu Pro Gln Val
    130                 135                 140

Tyr Thr Leu Pro Pro Ser Arg Asp Glu Leu Thr Lys Asn Gln Val Ser
145                 150                 155                 160

Leu Thr Cys Leu Val Lys Gly Phe Tyr Pro Ser Asp Ile Ala Val Glu
                165                 170                 175

Trp Glu Ser Asn Gly Gln Pro Glu Asn Asn Tyr Lys Thr Thr Pro Pro
            180                 185                 190

Val Leu Asp Ser Asp Gly Ser Phe Phe Leu Tyr Ser Lys Leu Thr Val
        195                 200                 205

Asp Lys Ser Arg Trp Gln Gln Gly Asn Val Phe Ser Cys Ser Val Met
    210                 215                 220

His Glu Ala Leu His Asn His Tyr Thr Gln Lys Ser Leu Ser Leu Ser
225                 230                 235                 240

Pro Gly Lys Arg Ser Pro Gln Pro Gln Pro Lys Pro Gln Pro Lys Pro
                245                 250                 255

Glu Pro Glu Gly Ser Leu Glu Val Leu Phe Gln Gly Pro Gly Ser Leu
            260                 265                 270

Gln His Ser Val Leu His Leu Val Pro Ile Asn Ala Thr Ser Lys Asp
```

```
        275                 280                 285

Asp Ser Asp Val Thr Glu Val Met Trp Gln Pro Ala Leu Arg Arg Gly
    290                 295                 300

Arg Gly Leu Gln Ala Gln Gly Tyr Gly Val Arg Ile Gln Asp Ala Gly
305                 310                 315                 320

Val Tyr Leu Leu Tyr Ser Gln Val Leu Phe Gln Asp Val Thr Phe Thr
                325                 330                 335

Met Gly Gln Val Val Ser Arg Glu Gly Gln Gly Arg Gln Glu Thr Leu
            340                 345                 350

Phe Arg Cys Ile Arg Ser Met Pro Ser His Pro Asp Arg Ala Tyr Asn
        355                 360                 365

Ser Cys Tyr Ser Ala Gly Val Phe His Leu His Gln Gly Asp Ile Leu
    370                 375                 380

Ser Val Ile Ile Pro Arg Ala Arg Ala Lys Leu Asn Leu Ser Pro His
385                 390                 395                 400

Gly Thr Phe Leu Gly Phe Val Lys Leu
                405


<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      linker region peptide

<400> SEQUENCE: 19

Pro Gln Pro Gln Pro Lys Pro Gln Pro Lys Pro Glu Pro Glu
1               5                   10


<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      protease cleavage site peptide

<400> SEQUENCE: 20

Leu Glu Val Leu Phe Gln Gly Pro
1               5


<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      tetrapeptide

<400> SEQUENCE: 21

Gly Ser Leu Gln
1


<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      hemagglutinin peptide

<400> SEQUENCE: 22
```

-continued

```
Met Ala Ile Ile Tyr Leu Ile Leu Leu Phe Thr Ala Val Arg Gly
1               5                   10                  15
```

PHARMACEUTICAL COMPOSITION COMPRISING EDA-1 FUSION PROTEIN

CROSS-REFERENCE TO RELATED APPLICATIONS

This application is a continuation of U.S. patent application Ser. No. 12/756,268 filed on Apr. 8, 2010 which is a continuation of U.S. patent application Ser. No. 10/503,999 filed on Oct. 25, 2004, which is a 35 U.S.C. §371 National Phase Entry Application of International Application No. PCT/EP2002/009354 filed Aug. 21, 2002, which designates the U.S., and which claims the benefit under 35 U.S.C. 119 of German Application No. 10205368.5 filed Feb. 10, 2002 and German Application No. 10205583.1 filed Feb. 11, 2002, the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Jul. 18, 2013, is named 053694-066696-C2 SL.txt and is 91,578 bytes in size.

The prior art discloses a large number of receptors which belong to the TNF receptor class and which in each case interact with at least one TNF ligand as the physiological ligand. The receptors of the TNF receptor family are type I membrane proteins (Nagata et al., Science, 267: 1449, 1995). An example of a well-investigated TNF receptor/TNF ligand system is the Fas receptor (Fas, FasR, CD95), which interacts with the natural ligand FasL and, in this way, induces an intracellular signal. The importance of the FasL/FasR system for cell-specific cell death has, in particular, been thoroughly investigated. The rat Fas ligand (Suda et al., Cell 75: 1169, 1993; Lynch et al., Immunity 1: 131, 1994) and the human form of the ligand (Takahashi et al., International Immunology 6: 1567, 1994) have been cloned at the cDNA level. As a member of the TNF ligand family, FasL belongs to the category of type II membrane proteins, i.e. FasL possesses an extracellular carboxyterminal domain and an intracellular aminoterminal domain. The proteins TNFa (tumor necrosis factor a) and TNFβ (tumor necrosis factor β, Eck et al., Journal Biological Chemistry 264: 17595, 1989), for example, also belong to the TNF ligand family. Each of the TNF ligands binds to its physiological TNF receptor. Other examples of these ligands from the prior art are OX40L (binds to OX40R), CD27L (binds to CD27R), CD30L (binds to CD30R), RANKL (binds to RANK-R), CD40L (binds to CD40R), TRAIL (binds to TRAIL-R1, R2, R3 or R4) and TWEAK (binds to Fn14).

However, the native forms of the ligands belonging to the type II membrane protein family are not suitable as such for medical use. As membrane proteins, they cannot be administered as such, either, because of the hydrophobic transmembrane domain, in particular. Attempts were therefore made, in the prior art, to make available TNF ligand fragments which might still be able to exhibit the physiological effect but which do not possess the intracellular segments or the transmembrane domain. For example, in-vitro and in-vivo experiments have been carried out using FasL fragments which only exhibit regions of the FasL domains which are disposed extracellularly in the native state (sFasL, i.e. soluble FasL). However, these protein fragments were only able to fulfil the physiological function of the ligands inadequately, particularly in the case of FasL, with the soluble extracellular FasL domain even sometimes being observed to exhibit unwanted effects which were the inverse of those of the FasL transmembrane protein, which is evidently present in active form as a trimer under physiological conditions.

The object of the present invention is therefore to make available sequences which not only imitate and reproduce the physiological effects of TNF ligands, for example FasL, but are also soluble and are therefore suitable for being used as pharmaceuticals, in particular for producing medicaments as well.

The invention makes available fusion constructs, i.e. both nucleotide sequences and the protein sequences which are derived from the nucleotide sequences, which also make it possible, in particular, to abolish the phenotype of genetically determined diseases, with it being possible to use specific therapeutic methods according to the invention for this purpose. Fusion constructs of the type according to the invention typically exhibit a structure as depicted in FIG. 1A to FIG. 1J. A construct according to the invention contains at least two components (A) and (B), namely a segment which is located N-terminally in the construct and which contains the sequence of the constant region of an immunoglobulin, or a fragment or a variant, for example a deletion mutant, substitution mutant or insertion mutant, (component A) and a sequence or part sequence of a ligand of the TNF ligand family (type II, component (B)), which is located more C-terminally in the fusion construct. According to the invention, the segment of the immunoglobulin (Ig), which is located N-terminally in the fusion construct, that is component (A), does not exhibit the variable region which is characteristic of immunoglobulins and which is responsible for antigen recognition but, instead, only exhibits domains, or segments of domains, of the immunoglobulin constant region, for example the domain(s) $CH_1$, $CH_2$ and/or $CH_3$. It is consequently possible, according to the invention, for segments of these CH domains, that is, for example, the domain $CH_1$ and the domain $CH_3$, to be linked to each other as component (A), in connection with which component (A) should not, according to the invention, lose its ability to bind to physiological Fc receptors during a treatment in utero. In the case of a postnatal treatment, the situation appears to be such that, where appropriate, it would be advantageous if the constructs according to the invention did not bind to Fc receptors. It can consequently be preferable, in the case of postnatal therapy, for component (A) to specifically no longer possess the property of binding functionally to Fc receptors. Such a loss of function can be achieved, for example, by means of inserting, deleting or replacing functional Fc sequences.

The immunoglobulin sequence which is derived from the Fc region and which is present as component (A) in the fusion construct according to the invention may be able to dimerize with another fusion construct or to be present as a monomer. Preference is given to component (A) being capable of dimerizing with a fusion construct according to the invention, which is preferably identical, or else, alternatively, with another fusion construct according to the invention, for example a fusion construct containing another component (B). The dimerization can take place by way of a disulfide bridge using the hinge region which, in a native state, is located between domain $CH_1$ and domain $CH_2$, or else also by way of an artificially introduced sequence (or else, for example, substitution/insertion of a cysteine) which is able to dimerize covalently (disulfide bridge) or noncovalently (for example leucine zipper or other sequence segments which are suitable for dimerizing). However, the fusion construct according to the invention can also be present as a single-chain antibody.

In a preferred embodiment, the constant region of the antibody in the fusion protein will be of human origin, for example originating from the antibody GI2765420, and belong to the immunoglobulin family derived from the IgG class of immunoglobulins, in particular from classes IgG 1, IgG2, IgG3 or IgG4, preferably from the class IgG2 or IgG4. It is also alternatively possible to use constant regions of immunoglobulins belonging to the IgG class from other mammals, in particular from rodents or primates; however, it is also possible, according to the invention, to use constant regions of the immunoglobulin classes IgD, IgM, IgA or IgE. Typically, the antibody fragments which are present in the construct according to the invention will comprise the Fc domain $CH_3$, or parts thereof, and at least one part segment of the Fc domain $CH_2$. Alternatively, it is also possible to conceive of fusion constructs according to the invention which contain, as component (A), the $CH_3$ domain and the hinge region, for the dimerization.

However, it is also possible to use derivatives of the immunoglobulin sequences which are found in the native state, in particular those variants which contain at least one replacement, deletion and/or insertion (combined here under the term "variant"). Typically, such variants possess at least 90%, preferably at least 95%, and very particularly preferably at least 98%, sequence identity with the native sequence. Variants which are particularly preferred in this connection are replacement variants which typically contain less than 10, preferably less than 5, and very particularly preferably less than 3, replacements as compared with the respective native sequence. Attention is drawn to the following replacement possibilities as being preferred: Trp with Met, Val, Leu, Ile, Phe, His or Tyr, or vice versa; Ala with Ser, Thr, Gly, Val, Ile or Leu, or vice versa; Glu with Gln, Asp or Asn, or vice versa; Asp with Glu, Gln or Asn, or vice versa; Arg with Lys, or vice versa; Ser with Thr, Ala, Val or Cys, or vice versa; Tyr with His, Phe or Trp, or vice versa; Gly or Pro with one of the other 19 native amino acids, or vice versa.

Very particular preference is given, for the treatment in utero, to those modifications of the abovementioned nature where the binding to membrane-located Fc receptors is at least not impaired but is, where appropriate, even optimized. However, when using constructs according to the invention for postnatal therapy, preference is given to minimizing or even abolishing the ability to bind to Fc receptors. Since fusion constructs according to the invention must contain, as component (A), sequences which have to retain the ability to bind to the respective physiological receptors for the constant segment of immunoglobulins, the amino acids at, in particular, positions 230 to 240, more preferably at positions 234 to 237, of domain $CH_2$ in the antibody fragment used as component (A) will consequently not be altered or only be provided with the sequence variations which leave the binding behavior with respect to Fc receptors, for example, unimpaired. On the other hand, preference is particularly given to replacements or deletions, as compared with the native sequence of immunoglobulin constant regions, at those positions which result in glycosylation sites being eliminated or inserted, disulfide bridges being inserted or eliminated, impair the stability or solubility, or improve passage through the cell membrane following binding following Fc receptors. Preference is given, in particular, to those variants which do not exhibit any structural changes, or only negligible structural changes, as compared with the three-dimensional folding of the native sequence. Such structural identity (and thus functional homology) can be determined by means of plotting appropriate spectra, for example a circular dichroism spectrum of the native sequence or of the given variant. The form of the spectrum, particularly in a measurement range between 190 and 240 nm wavelength, can always be used to establish structural identity. In this connection, the reader is referred, in particular, to the relevant literature of the manufacturers of instruments for measuring CD (e.g. Jasco, Japan).

C-terminally of the immunoglobulin fragment, a fusion construct according to the invention typically, but not necessarily, contains a transition region between components (A) and (B), which transition region can in turn contain a linker sequence, with this linker sequence preferably being a peptide sequence. This peptide sequence can have a length from between 1 and up to 70 amino acids, where appropriate even more amino acids, preferably from 10 to 50 amino acids, and particularly preferably between 12 and 30 amino acids. Examples of particularly strongly preferred transition sequences are depicted in FIGS. 1B to 1J (correspondingly labeled in these figures). The linker region of the transition sequence can be flanked by further short peptide sequences which can, for example, correspond to DNA restriction cleavage sites. Any restriction cleavage sites with which the skilled person is familiar from molecular biology can be used in this connection. Suitable linker sequences are preferably artificial sequences which contain a high number of proline residues (for example at every second position in the linker region) and, in addition to that, preferably have an overall hydrophilic character. A linker sequence which consists of at least 30% of proline residues is preferred. The hydrophilic character can preferably be achieved by means of at least one amino acid having a positive charge, for example lysine or arginine, or negative charge, for example aspartate or glutamate. Overall, the linker region therefore also preferably contains a high number of glycine and/or proline residues in order to confer on the linker region the requisite flexibility and/or rigidity.

However, native sequences, for example those fragments of ligands belonging to the TNF ligand family which are disposed extracellularly, but immediately act, i.e. in front of, the cell membrane, are also suitable for use as linkers, where appropriate after replacement, deletion or insertion of the native segments as well. These fragments are preferably the 50 AA which follow extracellularly after the transmembrane region or else subfragments of these first 50 AA. However, preference is given to these segments having at least 85% sequence identity with the corresponding natural human sequences, with very particular preference being given to at least 95% sequence identity and particular preference being given to at least 99% sequence identity in order to limit the immunogenicity of these linker regions in the fusion protein according to the invention and not elicit any intrinsic humoral defense reaction. Within the context of the present invention, the linker region should preferably not possess any immunogenicity.

However, as an alternative to peptide sequences which are linked to the antibody fragment and the TNF ligand, or a fragment of such a TNF ligand, by way of amide-like bonds, it is also possible to use compounds which are of a nonpeptide or pseudopeptide nature or are based on noncovalent bonds. Examples which may be mentioned in this connection are, in particular, N-hydroxysuccinimide esters and heterobifunctional linkers, such as N-succinimidyl-3-(2-pyridyldithio) propionate (SPDP) or similar crosslinkers.

In a fusion protein according to the invention, the transition region is typically followed carboxyterminally by a sequence of a member of the TNF ligand family, or a fragment or a variant thereof, as component (B) in a fusion construct according to the invention. Within the context of the present invention, preference is given to fragments which contain, in particular, the part of the extracellular segment of a member of the TNF ligand family which has the outermost carboxy-terminal location. The following TNF ligand family members, or variants or fragments thereof, are particularly preferred within the context of the present invention: FasL, TNFα/β, TRAIL, Tweak, LIGHT, CD40L, RANKL, CD30L, OX40L, CD27L, EDA1, BAFF and EDA2. The reader is referred to the corresponding entries in the SwissProt database (http://www.expasy.ch/sprot/sprot-top.html) with regard to the native sequences of the extracellular segments of the abovementioned proteins.

Preference is given, with regard to FasL, to fragments of amino acids 100 to 281 of the native sequence or fragments which are more truncated at the N terminus (e.g. AA 101 or 102 to 281), in particular 120 to 281 and very particularly 139 to 281, or fragments which are even more truncated at the N terminus, as component (B), or fragments which are even more truncated at the N terminus, while preference is given, with regard to EDA1, to fragments of amino acids 140 to 391, or fragments which are more truncated at the N terminus (e.g. 157, 160, 181 or 182 to 391), in particular 200 to 391, very particularly 245 to 391, or fragments which are even more truncated at the N terminus (e.g. 246 to 391), with regard to EDA2, to amino acids 180 to 389 or fragments which are more truncated at the N terminus (e.g. 181 or 182 to 389), or also preferably 200 to 389 and even more preferably 245 to 389 or fragments which are even more truncated at the N terminus, with regard to TNFa, to amino acids 50 to 228 or fragments which are more truncated at the N terminus (e.g. AA 51 or 52 to 228), more preferably 70 to 228, and most preferably 80 to 228, or fragments which are even more truncated at the N terminus, with regard to CD40L, to fragments of the segments 80 to 261 or fragments which are more truncated at the N terminus (e.g. 81 or 82 to 261), more preferably 100 to 261 and most preferably 116 to 261 or fragments which are more truncated at the N terminus (or fragments which are even more truncated at the N terminus), with regard to TRAIL, to amino acids 70 to 281 or fragments which are more truncated at the N terminus (e.g. AA 71 or 72 to 281), more preferably 80 to 281, and most preferably 95 to 281, or fragments which are even more truncated at the N terminus, with regard to BAFF, to amino acids 100 to 285 or fragments which are more truncated at the N terminus (e.g. AA 101 or 102 to 285), more preferably 120 to 285, and most preferably 137 to 285, or fragments which are even more truncated at the N terminus, and with regard to APRIL, to amino acids 80 to 233 or fragments which are more truncated at the N terminus (e.g. 81 or 82 to 233), more preferably 90 to 233, and most preferably 98 to 233, or fragments which are even more truncated at the N terminus. However, all the sequence segments which are located between the ranges which are in each case mentioned above as being preferred can also be used in the N-terminal region of the sequences which are present as component (B) in the fusion protein according to the invention, with a fusion protein according to the invention typically terminating C-terminally with the native C-terminal end of the TNF ligand. However, it is also possible, where appropriate, for at least one amino acid, typically from 2 to 10 amino acids, in rare cases even more than 10 amino acids, to be deleted in the C-terminal region of the extracellular TNF ligand fragment which is used as component (B) in the fusion protein according to the invention.

The TNF ligand which is present in the fusion protein according to the invention can also contain at least one replacement, deletion and/or insertion, as compared with the native sequence, for the purpose of expressing desired biological effects such as solubility, stability or altered immunogenicity. As an alternative to the native TNF ligand sequence, it is also possible, according to the invention, to use, as component (B) in the fusion protein according to the invention, a variant which typically exhibits at least 75%, preferably 85%, and particularly preferably at least 95%, sequence identity with the native sequence and which has the same biological effect and is consequently functionally homologous in this respect. Such structural identity (and thus functional homology) can be determined by means of plotting appropriate spectra, for example a circular dichroism spectrum of the native sequence or of the given variant. The form of the spectrum, particularly in a measurement range between 190 and 240 nm wavelength, can always be used to establish structural identity. In this connection, the reader is referred, in particular, to the relevant literature of the manufacturers of instruments for measuring CD (e.g. Jasco, Japan).

Variants which are particularly preferred in this connection are replacement variants which typically contain less than 10, preferably less than 5, and very particularly preferably less than 3, replacements as compared with the respective native sequence. Attention is drawn to the following replacement possibilities as being preferred: Trp with Met, Val, Leu, Ile, Phe, His or Tyr, or vice versa; Ala with Ser, Thr, Gly, Val, Ile or Leu, or vice versa; Glu with Gln, Asp or Asn, or vice versa; Asp with Glu, Gln or Asn, or vice versa; Arg with Lys, or vice versa; Ser with Thr, Ala, Val or Cys, or vice versa; Tyr with His, Phe or Trp, or vice versa; Gly or Pro with one of the other 19 native amino acids, or vice versa.

However, alternatively, and finally, it is also possible to use, as component (B), a substance which imitates the effects of physiological ligands, for example an organic molecule which has an agonistic effect on the corresponding TNF family receptor or an antibody which can bind agonistically to a TNF receptor and, after interaction with the receptor, induce the biological function of the physiological TNF ligand. As an example, mention may be made of the function of FasL, which function can also be achieved by an antibody, such as APO-1, as component (B), in a fusion construct according to the invention. Polypeptides which are able to introduce the physiological effect of TNF ligands can be identified, for example, by means of appropriate phage display methods (see U.S. Pat. No. 5,223,409, the entire teaching of which is hereby incorporated into the present disclosure by reference).

The invention also relates to a method for reversing genetically determined diseases or to a use of a fusion protein according to the invention for producing and formulating a pharmaceutical for a corresponding therapeutic method according to the invention. This method according to the invention can be used in connection with all Placentalia, that is vertebrates possessing a placenta, in particular in human and veterinary medicine. Following diagnosis of a genetically determined disease in an embryo, for example by means of chorion biopsy or amniocentesis, or when a genetically determined disease is suspected in an embryo on the basis of the genetic disposition of relations, in particular father and/or mother, the method according to the invention is suitable for already treating the embryo prophylactically and reversing its hereditary phenotype. The treatment is effected using a fusion protein according to the invention, as disclosed above, where appropriate in a corresponding formulation, and is ideally administered to the mother, or the mother animal, at the earliest possible time in the pregnancy. Such a fusion protein according to the invention is advantageously administered parenterally, preferably intravenously or intraarterially.

After a pharmaceutical has been administered, a fusion protein which is in accordance with the invention and which is of the previously described type binds, according to the invention, by way of its Fc moiety, as component (A), to the Fc receptors in the placenta and in this way, after having been internalized, reaches the embryo, typically by way of the placental vessels which connect the embryo to maternal blood circulation.

The dose depends on the genetic disease itself and on the time of the administration (that is on the developmental stage of the embryo), in connection with which the treatment should advantageously start at the earliest possible time in the development of the embryo. These Fc:ligand constructs according to the invention, e.g. Fc:EDA1 or Fc:EDA2, are administered at least once, more preferably regularly during the first, second and/or third month of the pregnancy, very particularly preferably, for example, on every second day for a period of at least 14 days in the case of a human embryo, where appropriate, however, at longer intervals as well depending on the dose which is chosen.

In principle, however, the dose of a fusion construct according to the invention depends on the method of treatment. In the case of treatment by the method according to the invention, that is during embryonic development, typical doses of the administered construct of less than one tenth, preferably less than one hundredth, and even more preferably less than one thousandth, of the native concentration of the TNF ligand in the neonate are recommended. When the neonate or the infant is being treated with a fusion protein according to the invention, the doses will be at least 1/100, more preferably at least 1/10 (always based on the TNF ligand activity) of the serum concentration which is typical for a healthy patient of the same age.

Very particular preference is given to a method according to the invention, or to the use of a fusion protein according to the invention for formulation as a pharmaceutical in such a method, when a fusion construct according to the invention is administered which carries an Fc moiety at the N terminus of the fusion construct and, as component (B) at the C terminus, a segment of the TNF ligand EDA1 or EDA2, in particular EDA1 or EDA2 of human origin, in particular an extracellular segment of these proteins which extends from at least amino acid 200 to amino acid 391 (EDA1) or up to amino acid 389 (EDA2), very particularly preferably from amino acid 245 to 391 (EDA1) and from amino acid 245 to 389 (EDA2). Those fusion constructs according to the invention as are depicted in FIGS. 1D and 1E are even more preferred for a method according to the invention or for a corresponding use.

In veterinary medicine, these fusion constructs according to the invention can be used to reverse the phenotype of the progeny of tabby mice by means of treating the mice, in accordance with the method, during pregnancy. Correspondingly, a method according to the invention, or the use of fusion proteins according to the invention for producing pharmaceuticals which are suitable for the method, can also be employed for therapeutic treatment of the analogous human disease, that is an hereditary disease which is based on the same genetic defect, namely X-coupled hypohydrotic ectodermal dysplasia (XLHED, Christ-Siemens-Touraine Syndrome), the most frequent form of ectodermal dysplasia. XLHED is due to a defect in the ED1 gene, with this defect corresponding, in human medicine, to the following clinical disease picture: hyposomia, varying degrees of dementia, saddle nose, anhidrosis, missing teeth or abnormal development of the teeth, hypertrichosis or alopecia, or dysfunction or lack of eccrine sweat glands, for which reason the affected patients are extremely susceptible to hyperthermia. Apart from XLHED, other ectodermal dysplasias, which are based on other hereditary causes, can also be treated in the manner according to the invention, either during embryonic development or else conventionally, by means of administration to the neonate or the infant.

The present invention consequently also relates to the use of fusion constructs according to the invention for treating genetically determined diseases in humans or animals, in particular by means of a method in accordance with the invention, as described above, or for producing a pharmaceutical. Fusion constructs according to the invention, in particular constructs which contain segments of the TNF ligand EDA1 or EDA2, for example the fusion constructs in accordance with FIG. 1D and FIG. 1E, are particularly suitable, in a general manner, for treating (or for producing a pharmaceutical for treating) genetically determined skin anomalies, in particular anomalies of the skin structure or else anomalies of ectodermal structures such as anomalies of the hair, of the teeth or of the glands (anhidroses or dyshidroses of varying genesis). An example which may be mentioned is the use of fusion proteins according to the invention in the cosmetic field, for example for treating alopecia, either acquired (for example in the form of alopecia areata, alopecia atrophicans, alopecia seborrhoeica or alopecia praematura) or congenital (especially as the syndrome of anhidrosis hypotrichotica) or hirsutism. However, fusion constructs according to the invention can also quite generally be used for treating, or for producing a pharmaceutical for treating, all forms of ectodermal dysplasia. For this reason, fusion constructs according to the invention, in particular those involving EDA1 or EDA2, are particularly suitable for treating, or for producing a pharmaceutical for treating, stimulation of hair growth or inhibition of hair growth, for treating disturbances in the growth of the teeth, or else for treating disturbances in gland function, including that of the sweat glands and/or sebaceous glands, or are suitable for promoting hair follicle formation or wound healing, in particular for promoting wound healing in patients for the purpose of ensuring appropriate growth of hair on the affected area of the skin. These fusion constructs can be used in a conventional manner, i.e. by preferably administering them to the patient postnatally, in human therapy very particularly preferably within the first year of life, even more preferably within the first 6 months of life, even more preferably within the first 2 months of life, even more preferably within the first 2 weeks of life and even more preferably within the first 3 days after birth, or else by means of the method described in accordance with the invention, i.e. by administering them to the pregnant mother or mother animal, e.g. by means of injection in utero. The fusion constructs according to the invention can consequently also be used for treating the abovementioned syndromes, genetic diseases or disturbances during embryonic development, by administering them to the mother or the mother animal.

When using constructs according to the invention for producing a pharmaceutical for treating, or treating, in particular, alopecia or, in particular, for promoting wound healing, for example following skin burns or inflammatory skin diseases, e.g. when treating neurodermitic or atopically affected areas of the skin, in particular of the scalp, it is also suitable to administer these constructs, where appropriate while using other auxiliary substances, carrier substances or additives, and also other active compounds where appropriate (e.g. when treating alopecia: Relaxin, substances having an anti-androgenic effect, e.g. finasteride, SKL-105657, oestrogen, cyproterone acetate, spironolactor, flutamide, minoxidil and/or RU58841) to adults, for example by means of intravenous or intraarterial or subcutaneous administration, following appropriate processing (formulation), or else orally or as a cream, lotion or ointment for topical use.

Another possible area of employment for constructs according to the invention is their use in producing skin tissue ex vivo. For example, items according to the invention, for example in the form of the proteins, the nucleic acids or the expression vectors, can be used in order to (re)generate the natural functionality of the skin of patients suffering from skin diseases (for example diabetic ulcers) or burns, with the formation of eccrine glands, hair follicles and hair. In this connection, items according to the invention are added to cells or tissues in vitro. For example, items according to the invention can be used in the traditional method of skin grafting; that is, for example, autologous, healthy skin tissue from the patient, allogenic skin tissue from deceased persons or donors, or animal tissue, can be stimulated, before being transplanted and by treatment with fusion constructs according to the invention, to form hair follicles or eccrine glands, for example within the context of a pretreatment or within the context of extracorporeal culture. However, it is also possible to isolate multipotent precursor cells from healthy skin tissue (or other tissue) from the patient himself. These cells are formed into skin tissue by adding appropriate differentiation factors. These multipotent precursor cells can, by means of appropriate transfections, be transfected with sequences or expression vectors according to the invention, or else fusion constructs can be added to them during the formation of skin tissue. In this way, it is possible to use items according to the invention in what is termed "tissue engineering" (tissue culture) before the cultured tissue is retransplanted into the patient. For this, the tissue to be transplanted (precursor cell, stem cell or tissue cell) (in particular keratinocytes of the epidermis) or embryonic stem cell (autologous or allogenic) is in principle first of all isolated and then cultured in an open system on a matrix (natural, synthetic or xenogenic) or a biodegradable framework, with the cells being supplied adequately with added nutrients, oxygen, growth factors and constructs according to the invention and with harmful metabolites being eliminated. The present invention consequently also relates to an in-vitro method for culturing skin tissue which exhibits eccrine glands and natural hair growth.

In principle, a large number of genetic diseases, in particular hereditary diseases which are due to faulty expression of members of the TNF ligand family, can be treated in the manner in accordance with the invention. An example of another genetic disease which using a fusion construct according to the invention which contains an Fc moiety and a biologically active segment of CD40L as component (B), is immunodeficiency associated with hyperIgM (HIGM1), which is X-chromosomally linked and is an immunoglobulin isotype switching defect which is characterized by an elevated concentration of serum IgM and reduced concentrations of other Ig isotypes. This disease is due to a defect in the TNFSF5 gene. The syndrome of HIGM1 which this causes is due to defective expression of the CD40 ligand, which results in a defect in immunoglobulin isotype switching. A genetic defect of this nature affects, in particular, male patients in their early years (within the first 5 years of life), with these patients being especially susceptible to opportunistic infections and therefore falling victim to an unfavorable survival prognosis. By using a fusion construct according to the invention which contains an active segment of the extracellular CD40L domain as component (B), it is possible, for example by employing a method according to the invention for treatment during embryonic development, to achieve partial reconstitution of the precursor T cells which are capable of expressing the functional CD40 ligands, with this resulting in the chemical symptoms of this genetic disturbance being relieved.

Another part of the subject-matter of the present invention is directed towards the recombinant DNA constructs on which the fusion proteins according to the invention are based. Within the context of the present invention, DNA and protein constructs are dealt with jointly under the term "fusion constructs". Thus, a nucleotide construct according to the invention can, for example, encode the CH2 and CH3 domains of IgG, as component (A), and, for example, CD40L or EDA1 or BAFF or FasL, where appropriate linked by a transition region containing a linker. Accordingly, the underlying recombinant nucleotide sequences according to the invention encode all the protein fusion constructs according to the invention which have previously been disclosed. Particular preference is given to the nucleotide sequences of the fusion constructs disclosed in FIG. 1A to FIG. 1J. The nucleotide constructs according to the invention can be obtained, as cDNA, genomic DNA or in synthetic form, using cloning methods or by way of chemical synthesis, with a large number of methods from the prior art being suitable. For example, with regard to the sequences of the immunoglobulin Fc moiety domain which can appear in a nucleotide construct according to the invention, the reader is referred, for example, to the publication "Sequences of Proteins of Immunologic Interest", $1^{st}$ Edition, Kabat et al., US Department of Health and Human Services, 1991", with the entire content of this publication hereby being incorporated into the present disclosure by reference.

The sequences which are contained in a nucleotide construct according to the invention will typically be present in segments which are assembled by means of restriction and ligation. A nucleotide sequence according to the invention will typically contain expression control sequences, including promoters, ribosome binding sites, polyadylation sites and/or transcription termination sites, and, where appropriate, enhancers, which are operably linked to the nucleotide sequence according to the invention for a fusion protein according to the invention. A fusion protein according to the invention can be expressed by transfecting DNA segments containing such regulatory elements, for example on plasmid vectors, into bacterial cells, yeast cells, plant cells, insect cells and, preferably, mammalian cells, for example using the calcium phosphate method, electroporation or similar techniques. For achieving expression in eukaryotic cells, use is made of the promoter and, where appropriate, the enhancer sequence of, for example, immunoglobulin genes, SV40, retroviruses, cytomegalovirus, elongation factor Iα, etc. Preferred host cell lines include CHO cells, COS cells, Hela cells, NIH3T3 cells and various myeloma or hybridoma cell lines, including P2/0 and NS/0. The present invention relates to such a DNA sequence according to the invention which encodes a recombinant fusion protein according to the invention, to expression vectors which contain such a DNA sequence according to the invention and to host cells which are transfected with such an expression vector according to the invention.

All the abovementioned indications can also be treated with the DNA constructs, expression vectors or host cells according to the invention. In particular, the reader is referred, in this connection, to the corresponding therapeutic methods used in in-vivo or ex-vivo gene therapy (for example transfection of bone marrow cells). In this connection, very particular preference is given to gene therapy methods used in the developing embryo, that is, for example, removal of embryonic cells, for example embryonic stem cells as well, with this being followed by ex-vivo transfection with material according to the invention, for example an expression vector according to the invention, for example a retroviral or adenoviral carrier, and reimplantation into the embryo. The DNA construct according to the invention is preferably located downstream of a regulable promoter.

The plasmid vector comprising a DNA construct according to the invention will generally contain a selectable marker, such as gpt, neo, hyg or DHFR, and an amp, tet, kan, etc. gene, for expression in *E. coli*. A large number of plasmid vectors which is suitable for expressing heterologous proteins is available in the prior art. A fusion protein according to the invention advantageously contains a N-terminal sequence, for example a hemagglutinin sequence and/or tag sequences and/or at least one further "LEADER" sequence at the amino terminus of the fusion protein, in order to facilitate secretion of the fusion proteins from the cell, in particular passage through the ER into the extracellular space or into the medium.

Methods for constructing nucleotide constructs according to the invention which encode protein constructs according to the invention, for their linking to expression control sequences and/or their insertion into plasmids, for transfection into cells and the selection and, if desired, gene amplification of the fusion protein-expressing cell line, can be carried out using methods which are known from genetic manipulation, including restriction enzyme digestion, ligation, oligonucleotide sequences and PCR reaction (Sambrook et al., Molecular Cloning: Laboratory Manual, $3^{rd}$ Edition, Cold Spring Harbor Laboratory Press, 2001), with the entire content of this publication hereby being incorporated by reference in this regard.

A transfected cell line which is expressing and secreting a fusion protein according to the invention is selected and can, where appropriate, be cultured in serum-free medium (hybridoma SFM), by being passed through a decreasing concentration of serum, and can finally be subcloned. A fusion protein according to the invention can be purified (from what is preferably serum-free medium) after having been secreted, with the expression cell line having been cultured. Standard methods for purifying proteins include filtration, precipitation, protein A affinity chromatography, gel filtration, ion exchange chromatography, electrophoretic methods or the like. Essentially pure fractions of the fusion protein, of at least 90 to 95% homogeneity and preferably of at least 98 to 99% or higher, homogeneity, are then preferably employed for the pharmaceutical use.

The production of a pharmaceutical which comprises the fusion protein according to the invention will typically include its formulation in a pharmaceutically acceptable carrier material. This carrier material will typically comprise aqueous carrier materials, with use being made of water for injection (WFI) or water buffered with phosphate, citrate or acetate, etc., and the pH being typically adjusted to 5.0 to 8.0, preferably 6.0 to 7.0. The pharmaceutically acceptable carrier will additionally and preferably contain salt constituents, e.g. sodium chloride or potassium chloride, or other components which make the solution isotonic. Furthermore, the carrier can contain additional components such as human serum albumin, polysorbate 80, sugars and amino acids. A composition according to the invention of this nature can be combined, in the form of an injection or as a kit, in an appropriately suitable combination with a pharmaceutically acceptable carrier material or a mediator, such as sterilized water or physiological sodium chloride solution, vegetable oils, mineral oils, higher alcohols, higher fatty acids and non-toxic organic solvents, and, where appropriate, be provided with further additives. Examples of further additives which are suitable are fillers (for example saccharides (lactose, sucrose, mannitol or sorbitol), calcium phosphate, cellulose or their derivatives), binders (for example starch, gelatine and polyvinylpyrrolidone), stabilizers, preservatives, antiadsorbents, surface-active substances, dyes, flavorings, emulsifiers, buffering agents, isotonic agents, antioxidants, analgesics or the like. Sodium alginate, polyethylene glycol and/or titanium dioxide are, for example, preferably worked into the formulations. Corresponding formulations of a pharmaceutical are disclosed in Remington (1980), to which the reader is referred in this regard.

The concentration of the fusion protein according to the invention in formulations of this nature can vary within a wide range of from 0.001 to 10 mg per ml, preferably in a range of from 0.5 to 5 mg/ml. The formulation is preferably injected into the patient or the pregnant mother parenterally, that is, for example, intravenously, intraarterially, subcutaneously or intramuscularly. Alternatively, when treatment is being carried out using a method according to the invention, it is also possible to introduce the formulation directly into the vascular system of the embryo placenta or inject it into the amniotic sac.

The present invention is clarified by means of the following figures:

FIG. 1 shows the nucleotide and amino acid sequences of Fc:ligand constructs which are in accordance with the invention and which are used in accordance with the invention. FIGS. 1B-1J disclose SEQ ID NOS 1-18, respectively, in order of appearance.

In this connection, FIG. 1A depicts, by way of example and diagrammatically, the sequence segments of particularly preferred Fc:ligand constructs according to the invention. A signal peptide is typically located in the N-terminal region of a fusion protein according to the invention, which is encoded by an underlying nucleotide sequence, with this signal peptide being followed by an IgG Fc segment (component (A)), which is in turn followed by an (optional) linker region and, more C-terminally, by an (optional) protease cleavage site sequence and, more C-terminally (and at the C terminus of a fusion construct according to the invention) by a sequence which typically constitutes a sequence of part of a member of the TNF ligand family (component (B)). This part sequence which serves as component (B) in turn typically includes the C-terminal moiety of the extracellular segment of a ligand from the TNF family.

Constituent FIGS. 1B to 1J show specific sequences of constructs according to the invention, with these constructs using different members of the TNF ligand family, namely FasL (FIGS. 1B (Nucleotide sequence disclosed as SEQ ID NO: 1; protein sequence disclosed as SEQ ID NO: 2) and 1C (Nucleotide sequence disclosed as SEQ ID NO: 3; protein sequence disclosed as SEQ ID NO: 4), with and without a protease cleavage site), EDA1 and EDA2 (FIGS. 1D (Nucleotide sequence disclosed as SEQ ID NO: 5; protein sequence disclosed as SEQ ID NO:6) and 1E (Nucleotide sequence disclosed as SEQ ID NO: 7; protein sequence disclosed as SEQ ID NO: 8)), TNFa (FIG. 1F (Nucleotide sequence disclosed as SEQ ID NO: 9; protein sequence disclosed as SEQ ID NO: 10)), CD40L (FIG. 1G nucleotide sequence disclosed as SEQ ID NO: 11; protein sequence disclosed as SEQ ID NO: 12)), TRAIL (FIG. 1H nucleotide sequence disclosed as SEQ ID NO: 13; protein sequence disclosed as SEQ ID NO: 14)), BAFF (FIG. 1J nucleotide sequence disclosed as SEQ ID NO: 15; protein sequence disclosed as SEQ ID NO: 16)) and APRIL (FIG. 1I (Nucleotide sequence disclosed as SEQ ID NO: 17; protein sequence disclosed as SEQ ID NO: 18)). The constituent sequences of the above-mentioned members of the TNF ligand family are all of human origin and in each case possess the C-terminally located extracellular sequence segments of the native ligands, up to the native C terminus. The Fc domain (component (A)), which is located N-terminally, is linked to the TNF ligand segment (component (B)), which is located C-terminally in the fusion protein, by way of a linker region containing the amino acids PQPQPKPQPKPEPE (SEQ ID NO: 19). In addition to this, the sequences of fusion constructs according to the invention as depicted in FIGS. 1B, 1I and 1J contain a protease cleavage site, in each case having the sequence LEVLFQGP (SEQ ID NO: 20), such that the protease PreSCISSION (Amersham-Pharmacia) can cut the fusion constructs which are designed with such a protease cleavage site and thereby separate the immunoglobulin domain of the fusion construct from the TNF ligand segment. However, all sequences which are at least 4 AA in length and which can be recognized by any protease, for example a cysteine or an aspartate protease, are suitable for use as a protease cleavage site sequence. However, typically short sequences, i.e. of from 2 to 8 amino acids in length, can be present between the Fc domain and the linker or between the linker and the TNF ligand domain. The sequences in constituent FIGS. 1B to 1J contain the amino acids ARG-SER between the Fc segment and the linker, and, in constituent FIGS. 1C, 1D, 1E, 1F, 1G and 1H, at least the tetrapeptide GSLQ (SEQ ID NO: 21), where appropriate extended by further amino acids C-terminally of Q, is located N-terminally of component (B). These fusion constructs which also contain a protease cleavage site, that is the fusion constructs in constituent FIGS. 1B, 1I and 1J, contain the above-mentioned tetrapeptide C-terminally of the protease cleavage site. The linker and the protease cleavage site are typically also separated from each other by at least two amino acids, in accordance with the figure by the dipeptide GS. The entire region between component (A) and component (B) is termed the transition region.

At the N-terminus, that is N-terminally of the Fc domain, all the fusion constructs shown in FIG. 1B to 1J contain a pentadecapeptide (MAIIYLILLFTAVRG) (SEQ ID NO: 22) which, in the cases depicted, corresponds to a hemagglutinin sequence. In all the cases depicted, this signal sequence is linked to the Fc segment of the fusion construct (component (A)) by way of the dipeptide LD.

The linking sequences in FIGS. 1B to 1J which are not framed typically correspond to restriction enzyme cleavage sites which are used to attach the individual sequence components to each other.

All the fusion constructs depicted in the constituent figures were cloned in a PCR-3 mammalian expression vector (Invitrogen).

Figure 2:
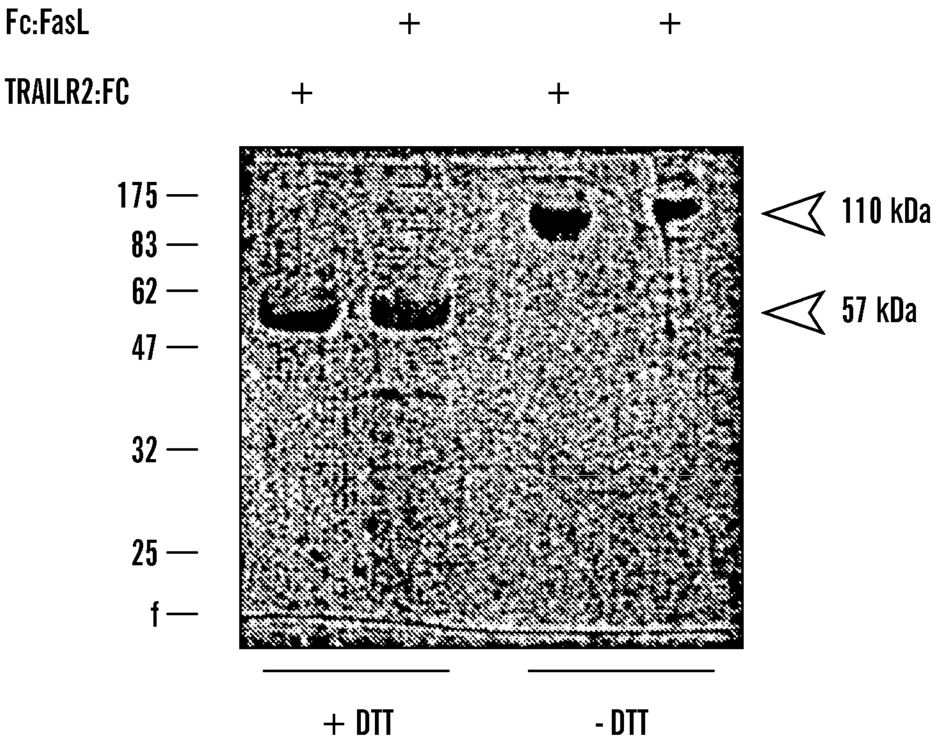

FIG. 2 shows a Western blot photograph which depicts the purification of the fusion construct Fc:FasL according to the invention. The purified protein (5 μg/lane) was examined on 12% SDS-page under reducing (+DTT) or nonreducing (−DTT) conditions and using the fusion construct TRAILR2:Fc (that is a construct containing an immunoglobulin domain and a TNF receptor) as a control in the lanes indicated by a (+) label above the Western blot. Molecular weight markers are indicated in kDa on the left-hand side of the Western blot, while the molecular weights (110 kDa and 57 kDa, respectively), which, as expected, vary in dependence on the formation of disulfide bridges (only under nonreducing conditions) between the Fc domains, which are indicated for the fusion construct Fc:FasL according to the invention are shown by arrows on the right-hand side of the Western blot.

Figure 3:
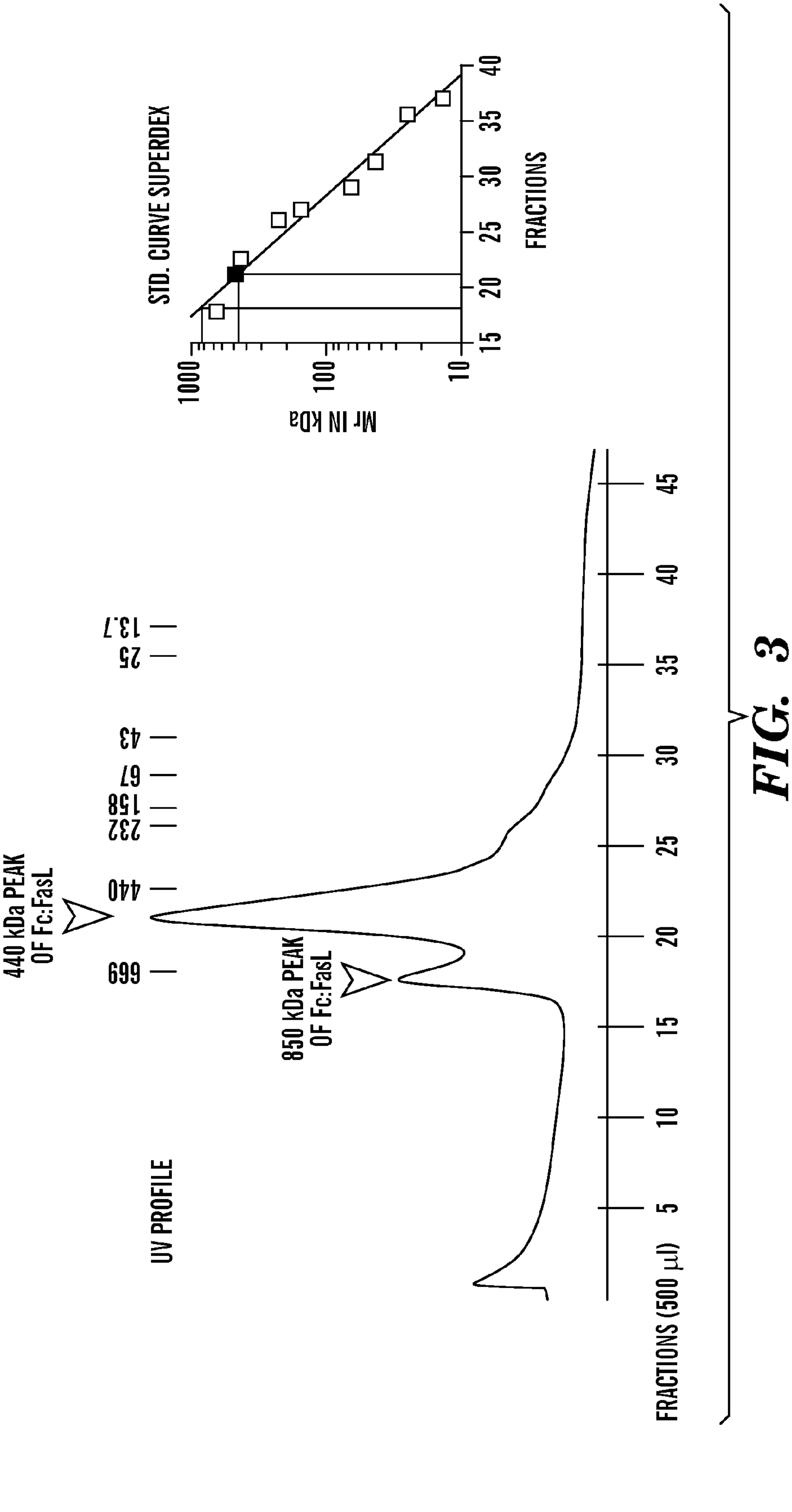

FIG. 3 depicts the result of the gel permeation chromatography of Fc:FasL according to the invention. For this, Fc:FasL (300 μg in 200 μl of PBS) was loaded onto a Superdex-200 column, which was equilibrated in PBS, and eluted at a rate of 0.5 ml/min. The UV profile was recorded online at 280 nm and 0.5 ml fractions were collected. The elution position is plotted below FIG. 3 and the molecular weight (in kDa), and the calibration standards, are plotted above the profile. The apparent molecular weights of the two Fc:FasL peaks were deduced from the calibration curve which is shown in the right-hand illustration in FIG. 3. The result is shown above the two peaks (850 kDa and, respectively, 440 kDa). Numbers of the investigated fractions are shown, in the order in which they were eluted, below the profile.

Figure 4A:
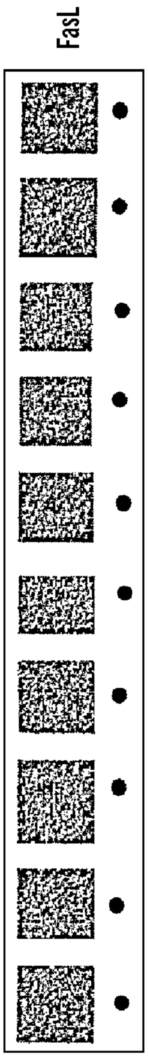
Figure 4B:
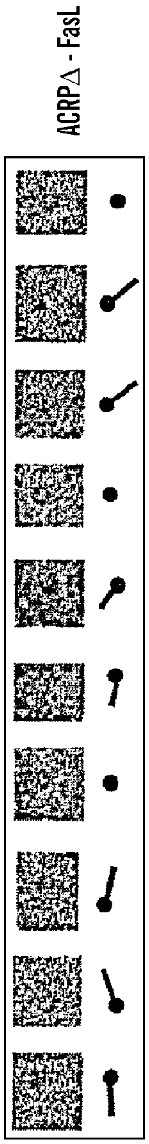
Figure 4C:
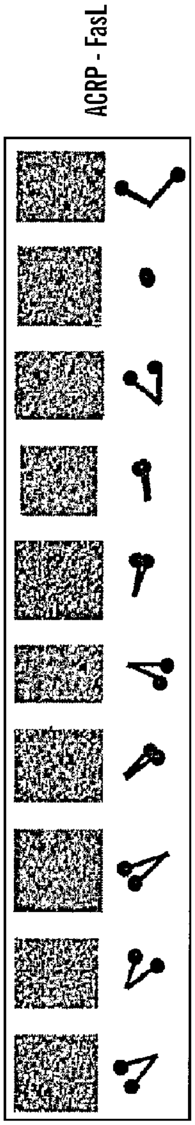
Figure 4D:
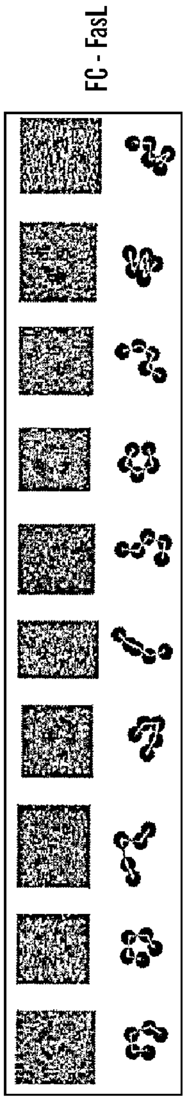

FIG. 4A to 4E shows electron microscopic photographs, i.e., in the order of the constituent figures, of FasL (FIG. 4A), of ACRPΔ-FasL (FIG. 4B), of ACRP-FasL (FIG. 4C) and, finally, of Fc-FasL (FIG. 4D). The individual constituent figures in each case contain different preparations of the injected amino acid sequences in alternative aspects, with a diagrammatic interpretation of the electron microscopically determined picture being depicted under each of the photographs. In this connection, the electron microscopic photographs shown in FIG. 4A result in a dot model in the case of FasL (3 ch, that is the expected trimer of multimerizing FasL), while, in the case of ACRPΔ:FasL (FIG. 4B), they result in a rod-shaped model having a dot end, with the dot marking the FasL component and the rod shape marking the collagen domain of ACRPΔ. FIG. 4C results, in the case of ACRP:FasL, in a twin cherry-like structure composed of two linked rods (ACRP30 collagen domain with an attached FasL domain. Finally, the structure of Fc:FasL according to the invention is shown in FIG. 4D, with the light dots representing FasL and the dark dots representing the Fc moiety of IgG1. The white line which links them depicts the connectivity between the different subunits.

Figure 4E:
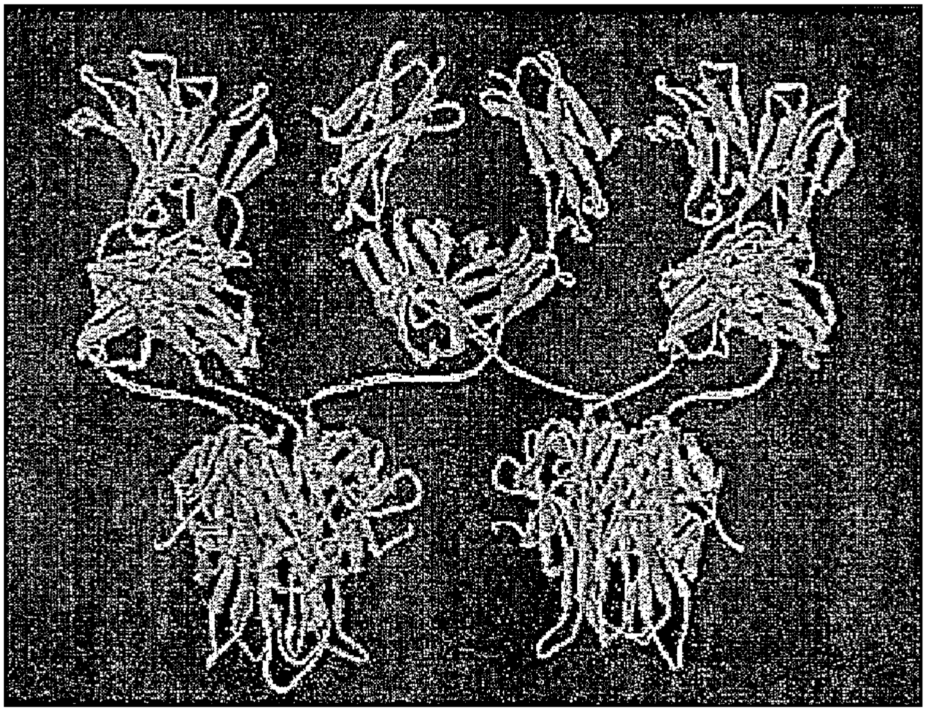

FIG. 4E is a depiction, in the form of a model, of the three-dimensional structure of an Fc:ligand complex according to the invention. The structure of Lymphotoxin A (PDB access number 1TNR) was selected as ligand while that of IgG 2a (PDB access number 1IGT) was selected as the Fc component.

Figure 5:
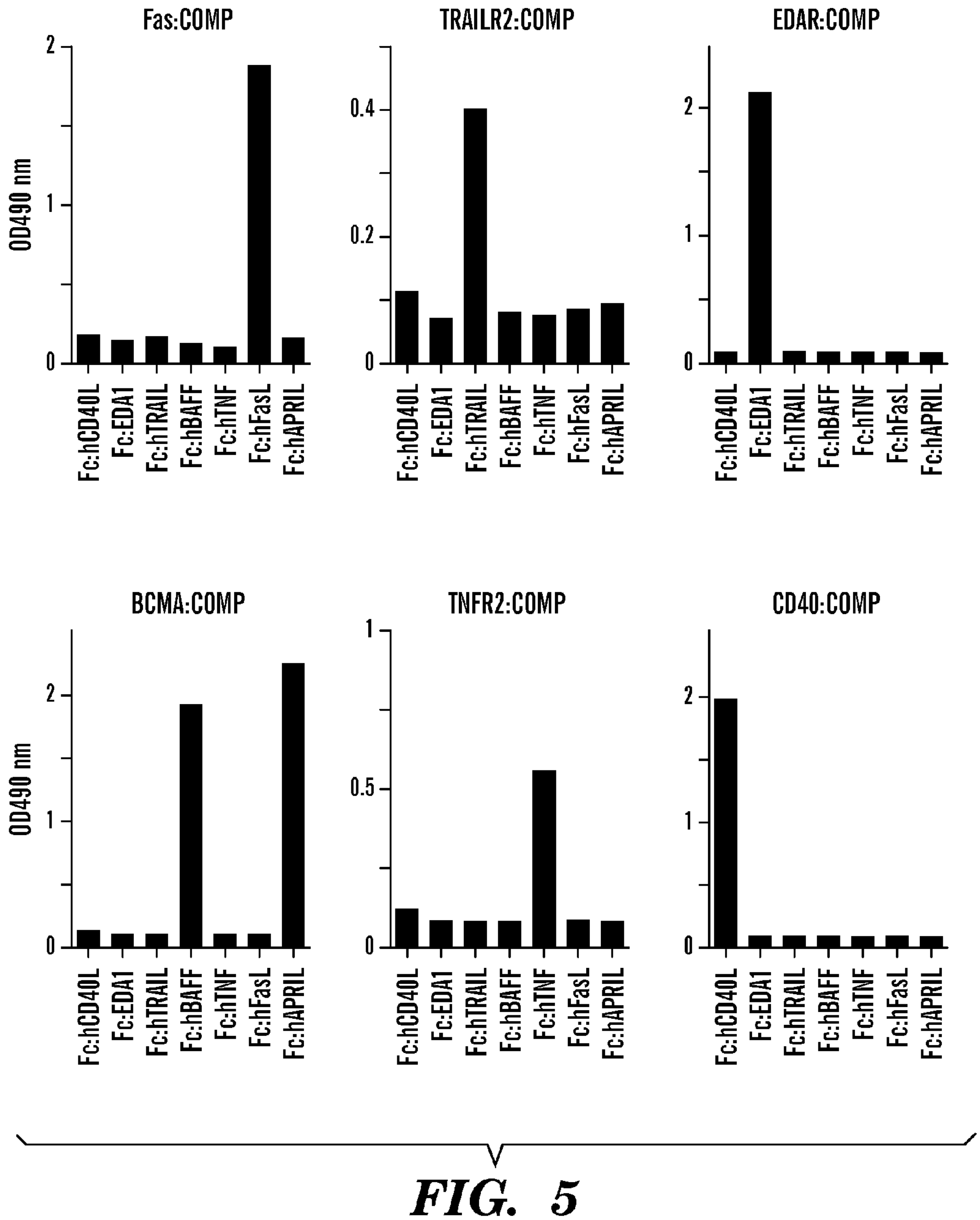

FIG. 5 shows the specificity of the binding of Fc ligands to their respective receptors. In this case, the binding of the ligands to their receptors (in the form of receptor:COMP fusion protein) was measured using an ELISA and employing the following steps: (a) coating with murine antihuman IgG, (b) adding the respective Fc ligands at the desired concentration (as a cell supernatant), (c) adding the respective receptor-COMP fusion construct (each of which carries a tag label and was also added as a cell supernatant), (d) adding biotinylated anti-tag monoclonal antibody, (e) adding horseradish peroxidase (HRP)-coupled streptavidin, and (f) developing the assay with OPD reagent and measuring the absorbence at 490 nm.

It can be clearly seen from the diagrams shown in FIG. 5 that the fusion constructs according to the invention have strong specificity for the respective TNF receptors which are specific for the ligands (or ligand segments) which are contained in the constructs according to the invention, namely with FasL having strong specificity for Fas, Trail for Trail R2, EDA1 for the EDA receptor, as expected BAFF and APRIL for the receptor BCMA, which is bifunctional in this respect, TNF for TNFR2 and CD40L for CD40R. Consequently, the preparation as a construct containing an Fc moiety has no effect on the behavior of the component (B) of a construct in regard to binding to the corresponding receptor.

Figure 6A:
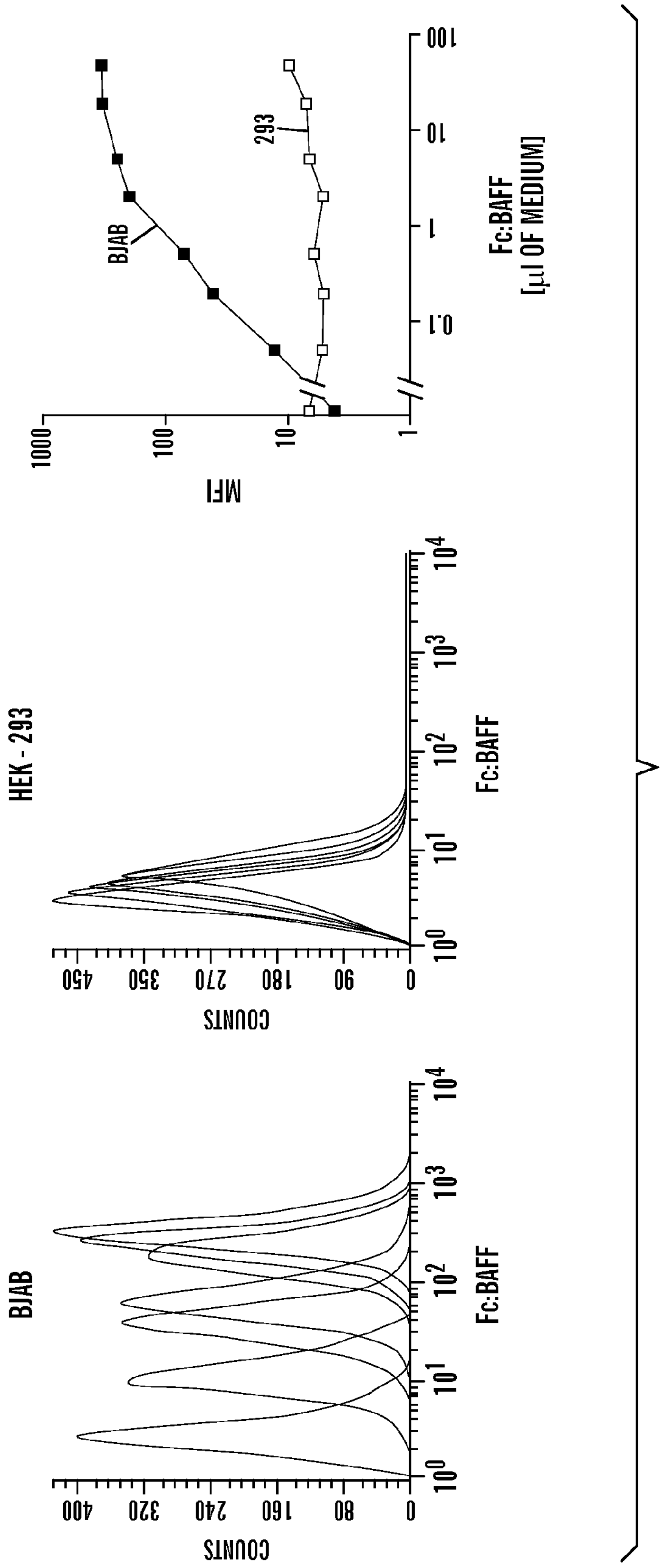
Figure 6B:
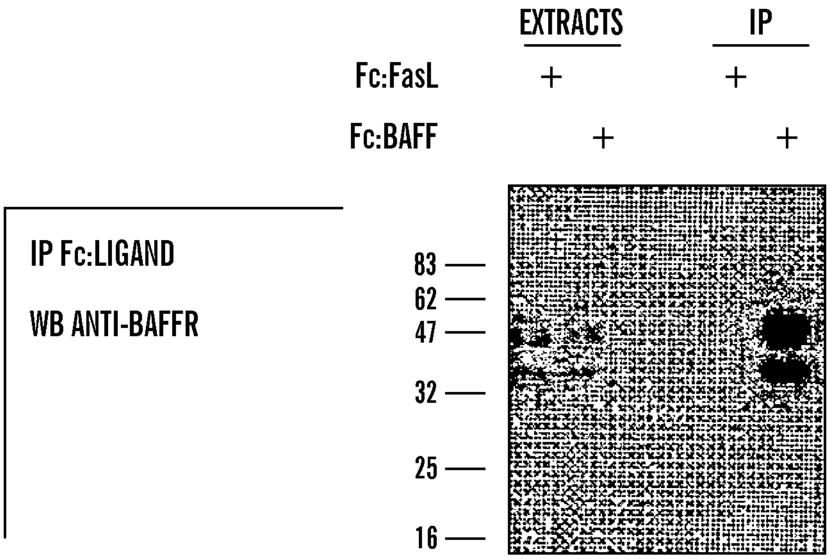

FIG. 6A to 6B shows the results of binding experiments using Fc:BAFF according to the invention. As shown in FIG. 6A, BJAB cells (BAFF-R-positive cells and HEK 293 cells (BAFF-R negative cells) were incubated with 0.05, 0.2, 0.5, 2.5, 20 or 50 μl of cell supernatants containing Fc:BAFF in a final volume of 100 microliters. Bound Fc:BAFF was identified using PE-conjugated anti-human Ig antibody and performing a FACS analysis. The result of quantifying the mean fluorescence (MFI) is shown in the right-hand diagram in FIG. 6A. In this connection, it is clearly seen that, after the direct plots for BJAB cells and HEK 293 cells have been analyzed in the secondary plot (far right in FIG. 6A), the mean fluorescence, as a measure of binding to the cells, increases markedly in the case of BJAB cells whereas the BAFF-R-negative HEK-293 cells do not exhibit any significantly increased mean fluorescence even when high concentrations of the Fc:BAFF according to the invention are present. Consequently, as was expected, Fc:BAFF does not bind to the BAFF-R-negative cells either, in contrast to the situation with regard to BAFF-R-positive cells.

FIG. 6B shows the results of immunoprecipitation experiments. For these, BJAB cells ($5 \times 10^7$ per assay) were incubated for 15 minutes in 2 ml of a medium in the presence of 3 μg of Fc:FasL or of Fc:BAFF. The cells were harvested, washed in PDS, lysed in a lysis buffer (containing 1% NP-40 and immunoprecipitated using protein A Sepharose. IPs and total cell extracts were analyzed by means of the Western blotting technique using a murine anti-hBAFF-R monoclonal antibody. In this connection, it was found that the BAFF-R-positive BJAB cells bind Fc:BAFF during the incubation (right-hand lane in FIG. 6B) and can therefore be detected with appropriate antibodies in the IP assay.

Figure 7:
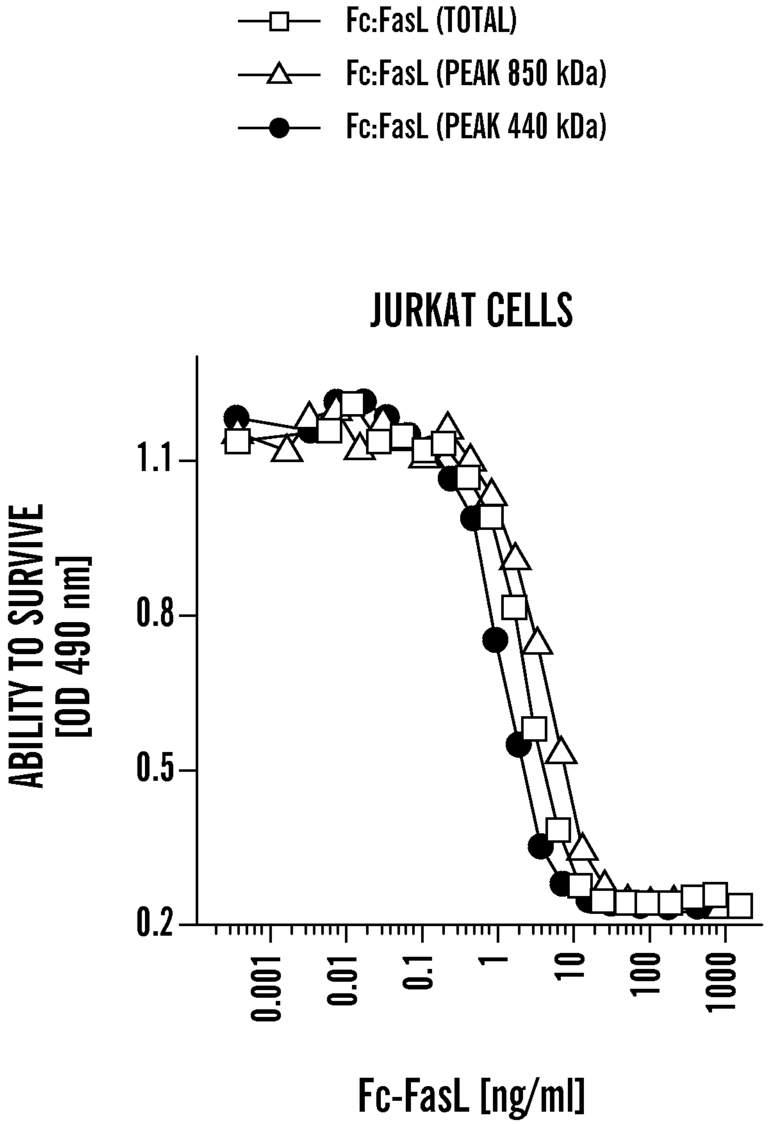

FIG. 7 shows the cytotoxicity of Fc:FasL when using serial dilutions of Fc:FasL according to the invention (as desired, the material loaded onto the column, the 850 kDa fraction or the 440 kDa fraction, as shown in FIG. 3). These serial dilutions were added to FasL-sensitive jurkat cells and were incubated at 37° C. for 16 hours. After that, the viability of the cells was examined using a PMS/MTS assay. In this connection, it was found that both the total fraction and the individual fractions have a very similar profile in regard to the ability of the cells to survive.

Figure 8A:
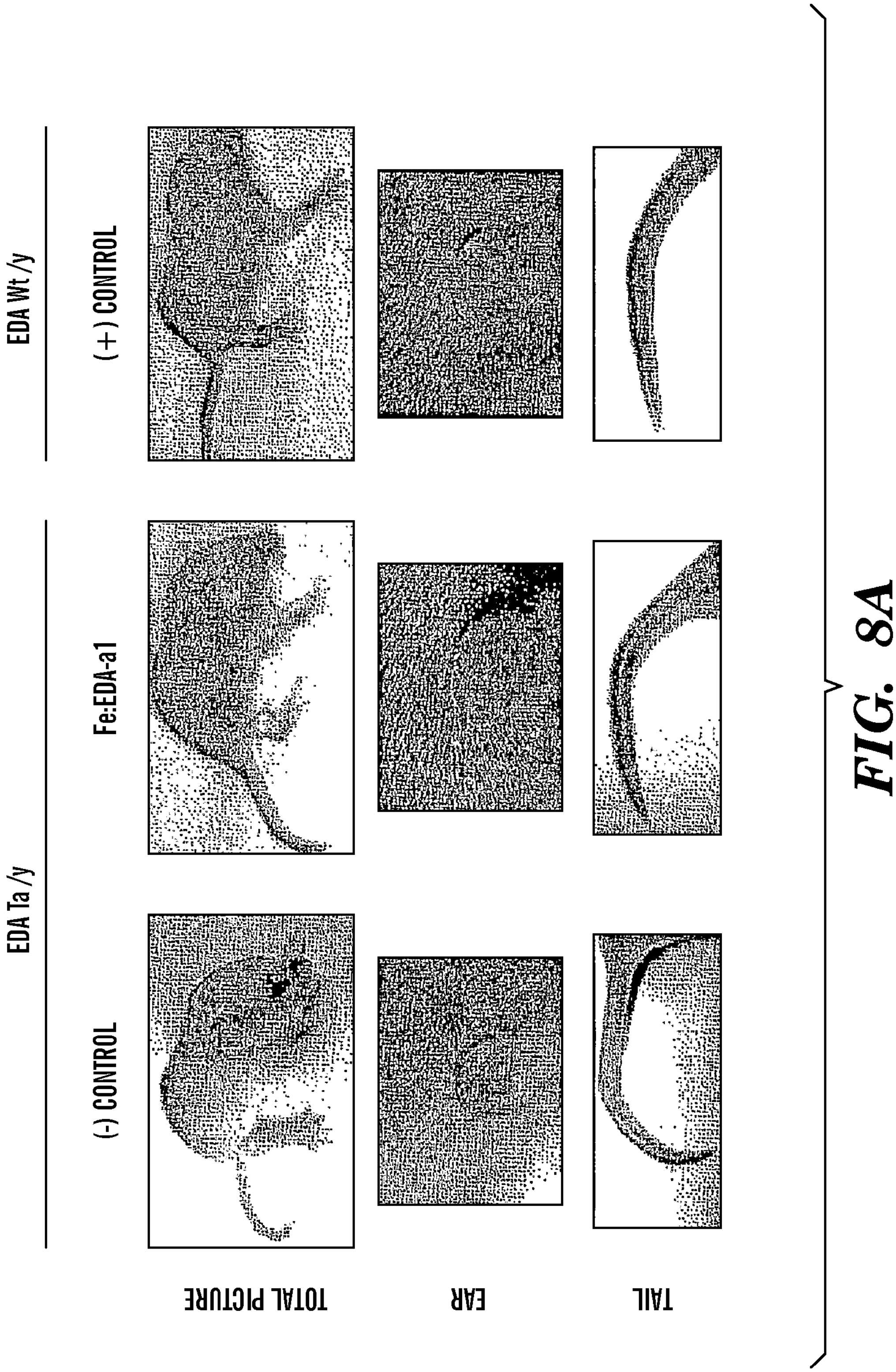
Figure 8B:
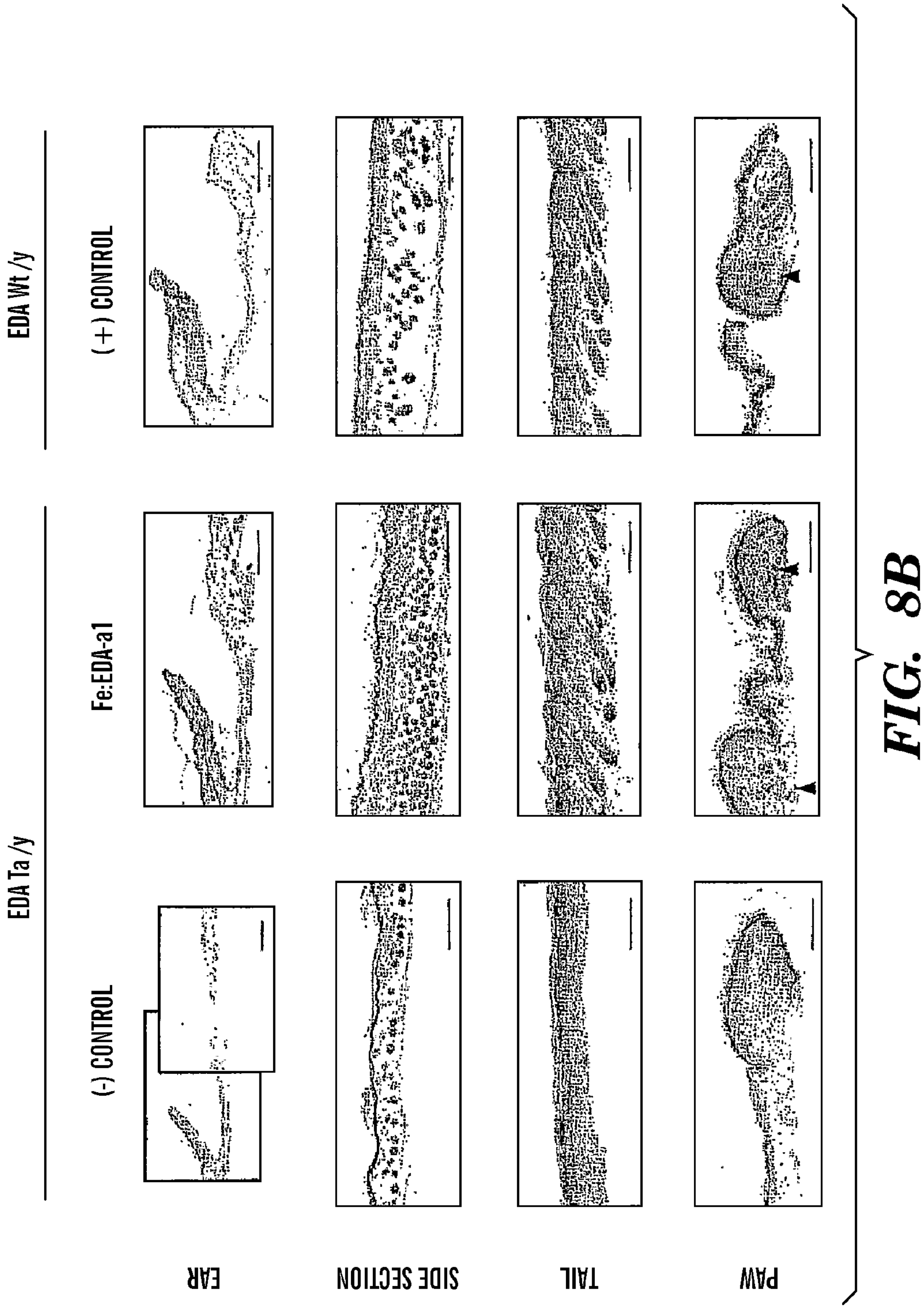

FIG. 8A to 8B shows the phenotypic differences between tabby mice which were treated, 10 days after birth, with Fc:EDA1 according to the invention (see FIG. 1D) or were left untreated. WT mice served as the control (right-hand side). For this, pregnant tabby mice were injected intravenously with 400 μg of Fc:EDA1 on days 11, 13 and 15 of the pregnancy. Progeny of treated tabby mice, untreated tabby mice and wild-type mice were examined. As shown in FIG. 8A, this examination took account of the appearance of the ear region, in particular of hair growths in the ear region. The growth of hair in treated animals corresponds to that in WT animals. The tail region in treated mice also exhibits hairiness which corresponds to that of WT mice, as well as the usual shape. The difference from untreated mice is immediately obvious.

FIG. 8B shows histological tissue section illustrations of the retrooricular region, of the side of the body, of the tail and of the paw in paraffin using hematoxylin/eosin staining. A pronounced bald region can be seen under the ears of untreated tabby mice. With respect to this, treated tabby mice phenotypically resemble the WT. The side of the body in treated tabby mice exhibits a WT-like increase in the number of hair follicles as compared with untreated tabby mice. In the tail region, the treated mice exhibit the hair growth seen in WT mice. On the other hand, untreated tabby mice lack hair in the tail region. As is also the case in the WT, sweat glands can be seen in the tissue of the paw in treated mice (middle), as indicated by the arrows. By contrast, untreated tabby mice do not develop any sweat glands. The following features were compared:

FIG. 9A to 9D shows a comparison of the results which were obtained when treating tabby mice in utero with the construct according to the invention shown in FIG. 1D with the results which were obtained in corresponding control animals.

Figure 9A:
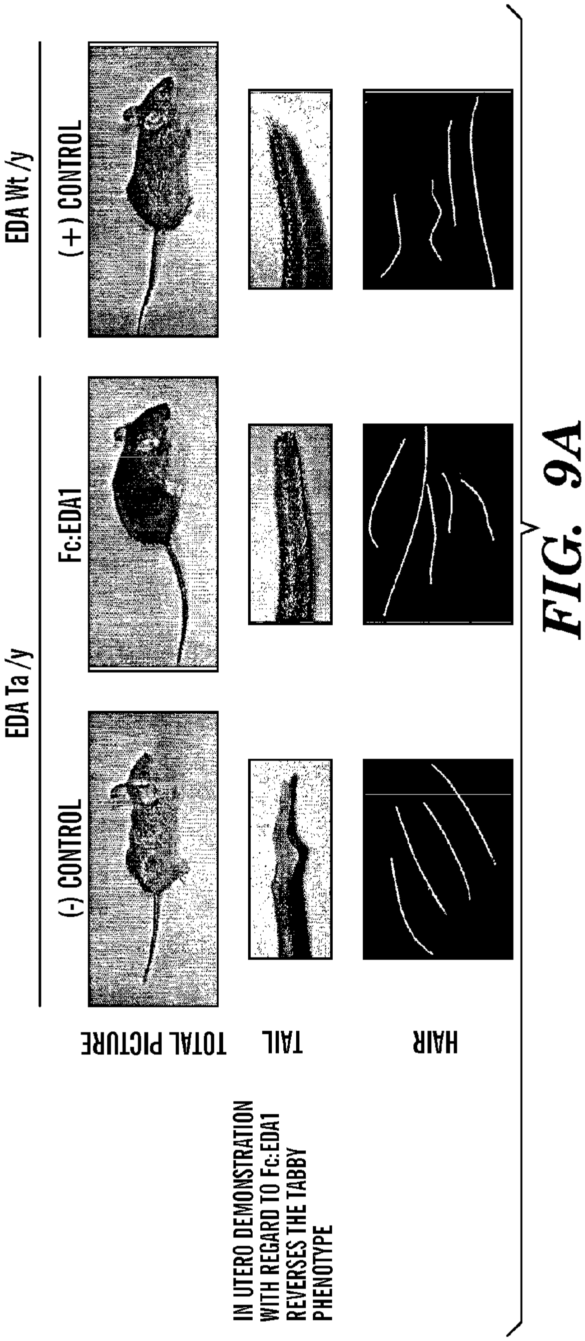

FIG. 9A shows a comparison of treated tabby mice (center) and untreated tabby mice (left) in adulthood (6 weeks after birth). The treatment took place as described in implementation example 4. The appearance of healthy mice, as a control, is recorded on the right. The treated animals possess a coat like that of the WT animals (including in the critical region of the tail); in the treated mice, the tail does not have any serrated appearance; the hair of treated mice exhibits the "monotrichous" hair type, which is typical for WT mice, in particular, especially long monotrichous covering hair which is entirely lacking in the untreated tabby mice.

Figure 9B:
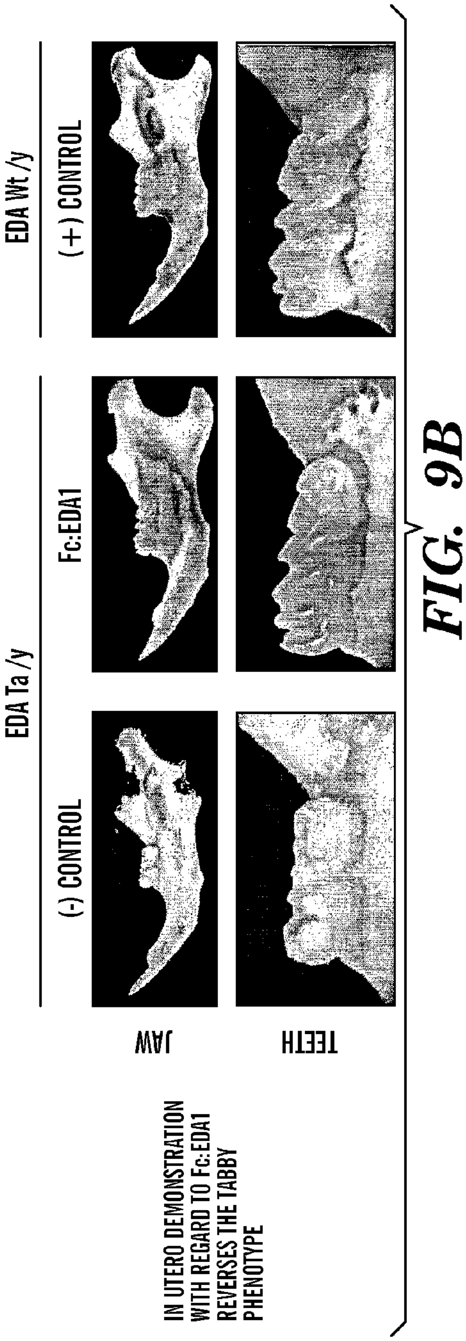

FIG. 9B compares the jaw and tooth structure of treated and untreated tabby mice and WT mice. The untreated tabby mice have an abnormal jaw structure and the teeth also exhibit deformities, in particular a lack of pronounced cusps. Treatment by a method according to the invention during pregnancy (treatment of the mother animal) restored the natural tooth form.

Figure 9C:
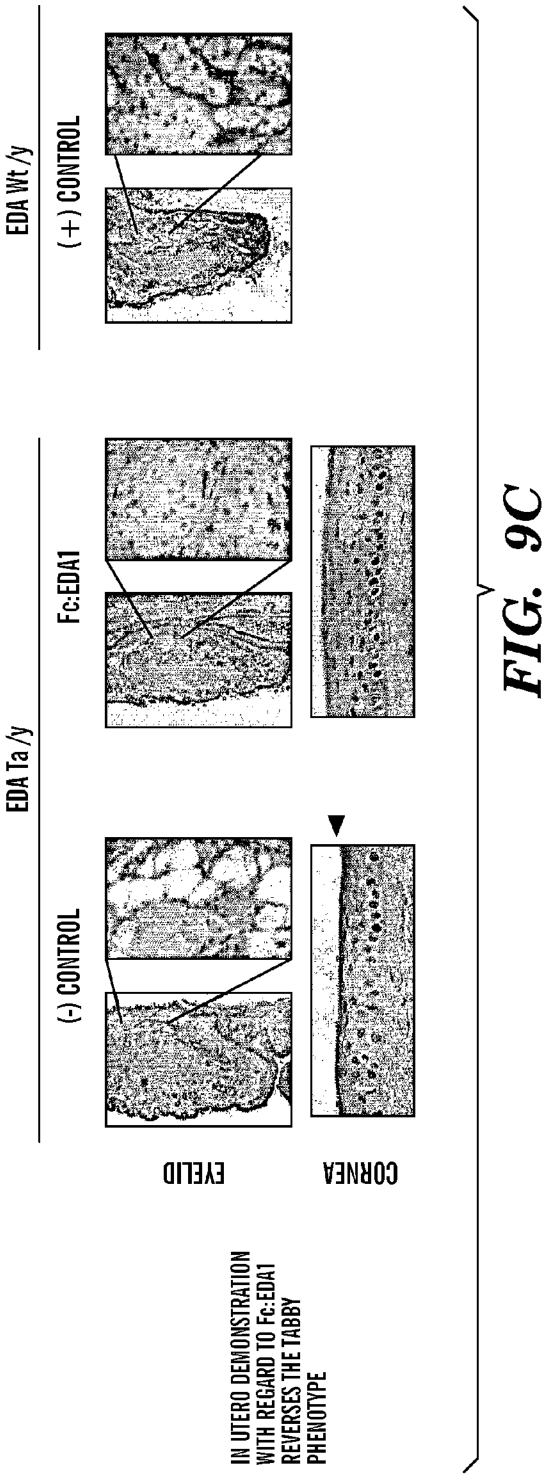

FIG. 9C shows tissue sections of the eyelid and the cornea in untreated tabby mice, in tabby mice treated, in accordance with the invention, with Fc:EDA1, and WT control animals. The untreated tabby mice characteristically lack the Moebius glands in the eyelid. However, these glands reappear after treatment in accordance with the invention. The regeneration of the Moebius glands also prevents the keratinization of the cornea which occurs, as can clearly be seen from the tissue section shown in FIG. 9C, in untreated tabby mice.

Figure 9D:
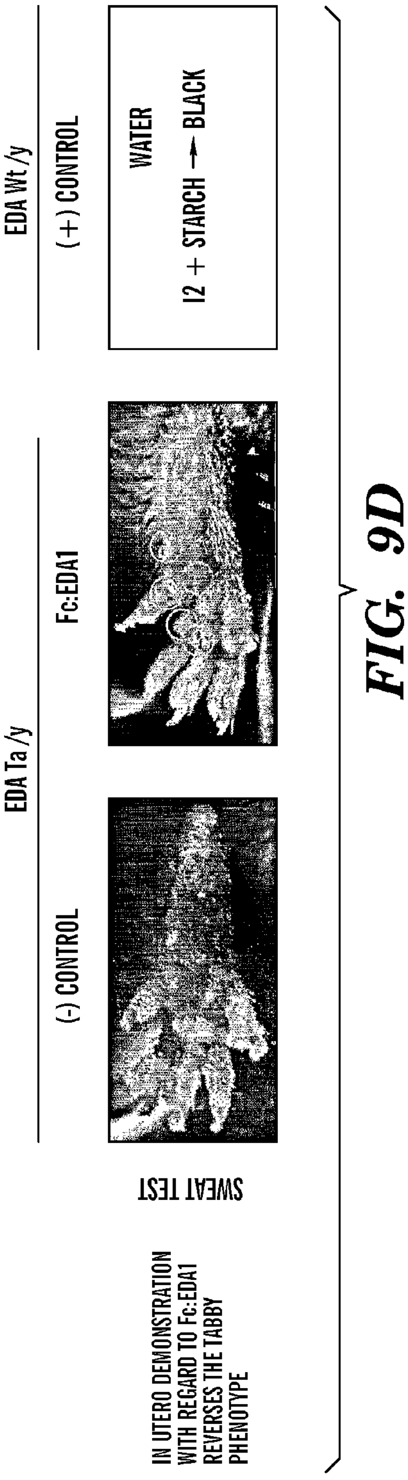

FIG. 9D depicts the results of the sweat test, which results show that functional sweat glands, which are absolutely lacking in untreated tabby mice, can be observed on the paw in the case of tabby mice which have been treated in accordance with the invention. These sweat glands, which have been regained following treatment with Fc:EDA1, make it possible to demonstrate the typical physiological reactions to stimuli such as heat and stress. The sweat test itself is described in implementation example 4.

Figure 10A:
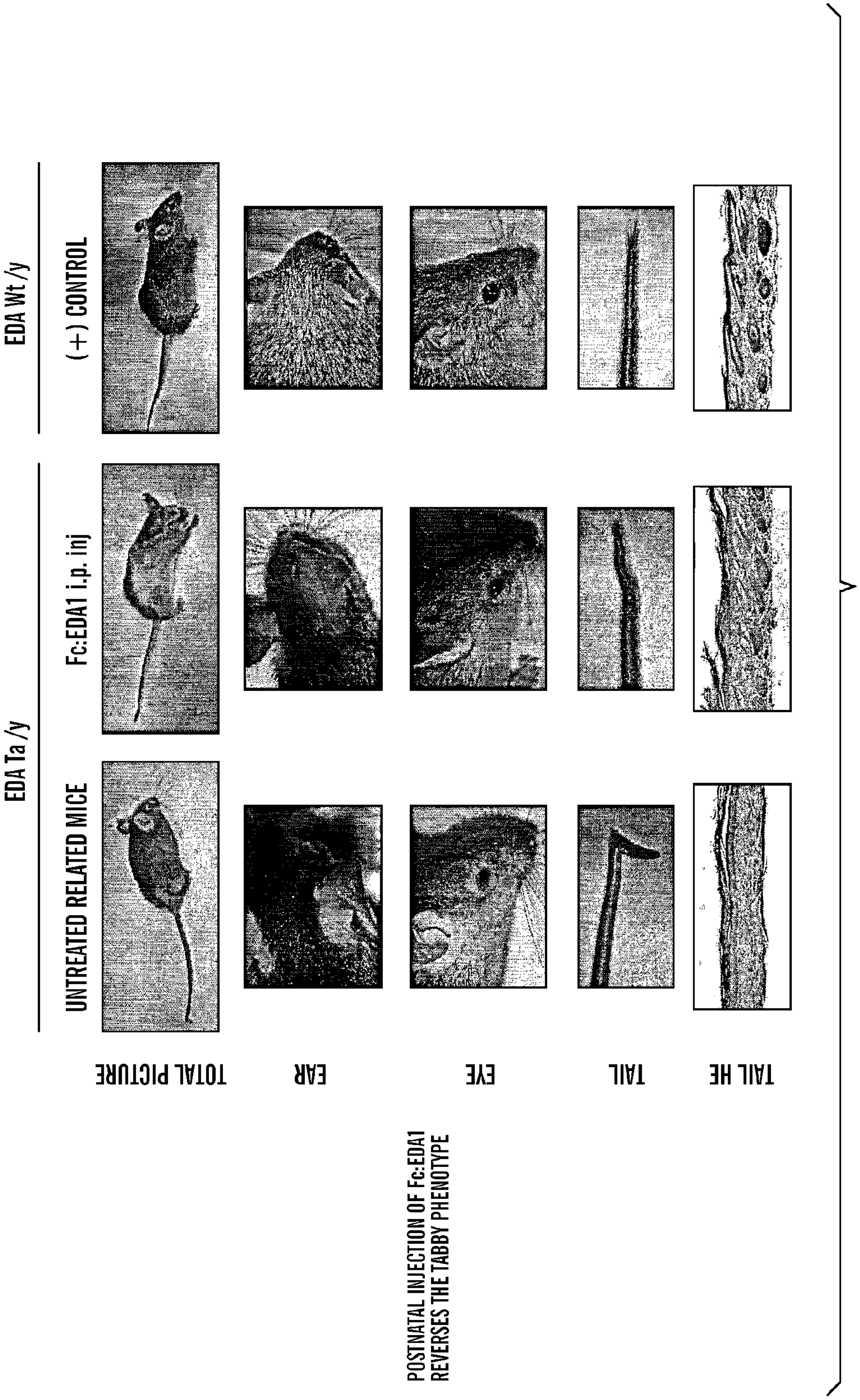
Figure 10B:
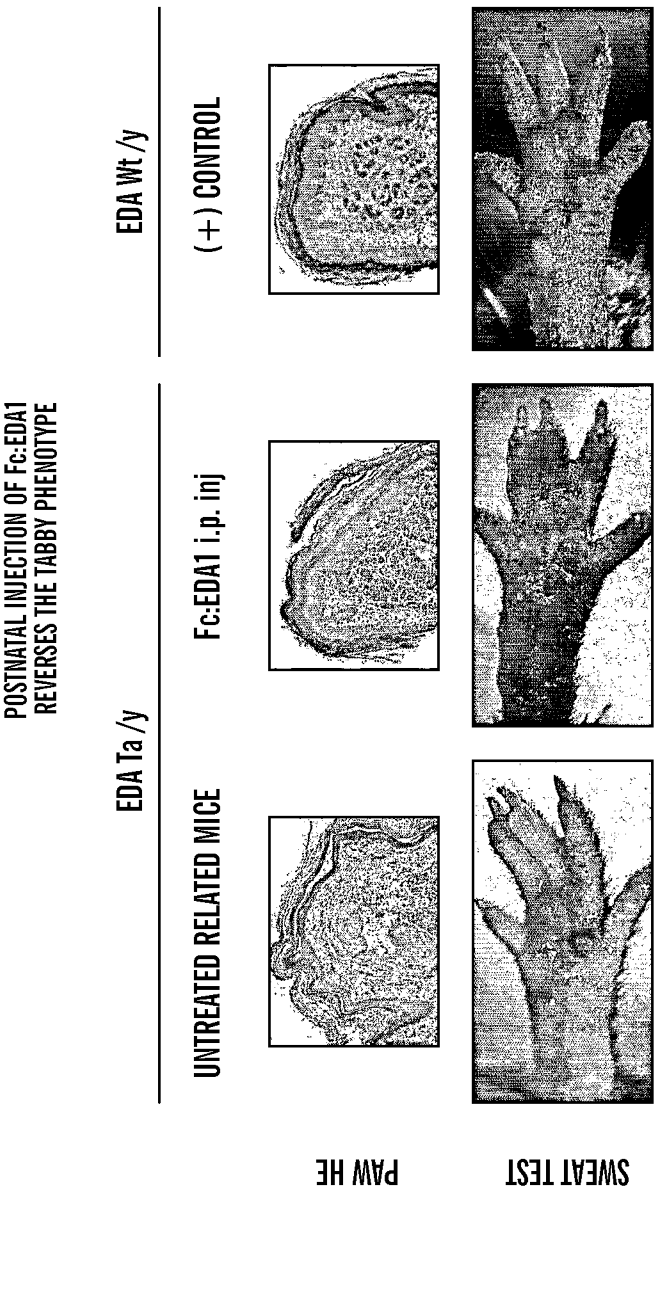

FIG. 10A to 10B shows a comparison of the results obtained following the postnatal intraperitoneal treatment of tabby mice with an Fc:EDA1 fusion construct according to the invention with the situation in untreated tabby mice and in WT control animals.

FIG. 10A compares different body regions in the above-mentioned three animal groups in regard to their phenotype. In contrast to the situation in the WT, the skin region behind the ears was not covered with hair in adult, postnatally treated animals, either. However, postnatal injection of Fc:EDA1 was able to almost completely restore tail hairiness as in the WT, on the one hand, and, on the other hand, the size of the eye aperture which is typical for the WT. The postnatal treatment according to the invention was able to virtually eliminate the "bent" tail form. In addition to this, tissue sections of the tail which were stained with hemotoxylin and eosin showed the presence of both numerous hair follicles and sebaceous glands associated with the hair follicles.

FIG. 10B shows, microscopically and macroscopically, the phenotypes of the three groups with regard to the sweat glands on the paws. A large number of sweat glands were observed on the paws of postnatally treated adult tabby animals, with these sweat glands being indistinguishable from the WT sweat glands, as FIG. 10B shows using tissue sections stained with hemotoxylin and eosin. These sweat glands in the treated tabby animals were found to be functional in an appropriate sweat test and reacted to physiological stimuli such as heat or stress.

In summary, therefore, it can be stated that, when treatment takes place in utero, the reversion of the phenotype which is observed following birth does not disappear in the adult animal just as the phenotypic reversions which are seen in the young animal in connection with postnatal treatment with substances according to the invention also persist in the adult animal.

The present invention is clarified by means of the following implementation examples.

IMPLEMENTATION EXAMPLES

1st Implementation Example

Preparing Fc:Ligand Fusion Proteins

Preferred fusion proteins according to the invention consist of an Fc moiety derived from human immunoglobulin (component (A)), with the underlying DNA sequence not containing the immunoglobulin stop codon, and a C-terminal segment of a fragment of a ligand belonging to the TNF family (component (B)) (containing the stop codon of the underlying DNA sequence). In this connection, preferred fusion proteins according to the invention have the following structure: a signal peptide at the N terminus, then an Fc segment, for example derived from IgG, a transition region containing a linker region and a protease cleavage site, and a C-terminal segment of a member of the TNF ligand family. A diagram of a preferred fusion protein according to the invention is shown in FIG. 1A.

In order to prepare a fusion protein according to the invention, for example a fusion protein having a preferred structure as shown in FIG. 1A, in particular the sequences depicted in FIGS. 1B to 1J (SEQ ID NOS: 1-18), nucleic acid constructs were cloned into mammalian expression vectors and expressed in stable human embryonic kidney cell lines (in HEK-293 or in CHO (Chinese hamster ovary) cells). The secreted recombinant fusion proteins were isolated from the conditioned medium by means of affinity chromatography on a Protein A Sepharose column. The yields amounted to several mg per lited of the medium employed.

2nd Implementation Example

Characterizing Fc:FasL Biochemically

FasL was characterized biochemically by means of SDS-PAGE analysis, with apparent molecular weight os 57 kDa and approximately 110 kDa being determined under reducing and nonreducing conditions, respectively. This demonstrated the presence of disulfide bridge-linked dimers (2 ch), as was to be expected of Fc-containing fusion proteins possessing a hinge region (see FIG. 2 as well).

A corresponding investigation carried out by means of gel permeation chromatography showed that two well defined peaks of Fc:FasL, having apparent molecular weights of approximately 440 kDa (main peak) and, respectively, approximately, 850 kDa (subsidiary peak) eluted (see FIG. 3). On the assumption that Fc:FasL has a globular form, the calculated multimer structure of FasL was 7.7 (7.7 ch) for the main species in the elution profile. However, if the protein is not typically globular in an ideal manner, this calculation is very probably based on an overestimate of the molecular weight, which means that a dimeric ligand structure (6 ch) would be perfectly possible. The form of Fc:FasL corresponding to the 440 kDa peak was examined in the electron microscope, using FasL (3 ch), oligomeric ACRP30:FasL (6+ ch) and a deletion mutant of ACRP30:FasL, namely ACRPΔ:FasL (3 ch), for comparison. FasL (3 ch) has a ball-like form (see FIG. 4A), while ACRPΔ:FasL (3 ch) has a ball-like form with a "handle" (see FIG. 4B) and ACRP30:FasL has the appearance of a "twin cherry", which, as has been shown, tallies with a dimeric FasL (6 ch) structure (see FIG. 4C).

Fc:FasL according to the invention regularly assumes a ring structure possessing 5 "balls" or an open structure possessing 5 "balls" (see FIG. 4D). This in turn corresponds to a dimeric FasL (6 ch), with two of the balls being FasL and the remaining 3 balls being the IgG Fc components (3 polypeptide dimers: 6 ch). A model representation of an Fc-ligand was developed using the known crystal structure of lymphotoxin a (a member of the TNF family) and the Fc component of IgG2a (PDB access numbers 1TNR and 1IGT), with the linker region being drawn in as a continuous line (see FIG. 4E). This representation shows unambiguously that the ligands and the Fc moieties are of approximately similar sizes, in agreement with the observed 5-ball structure of Fc:FasL. All in all, these results indicate that the 440 kDa peak of Fc:FasL is a dimeric FasL (6 ch).

In the present disclosure, the designation "ch" stands for "chain" and thereby reflects the number of chains of the TNF ligand (for example APRIL, FasL, BAFF, EDA or Tweak) in the molecule (independently of whether a fusion construct is being considered or not). If a TNF ligand is present in trimeric form, it has three chains (3 ch), while a dimer of a ligand (for example as a result of the Fc construction according to the invention) has 6 ligand chains (6 ch).

The other fusion protein sequences according to the invention depicted in FIGS. 1B to 1J were characterized in an analogous manner.

3rd Implementation Example

Biological Activity of the Fc:Ligand Constructs According to the Invention In Vitro According to the invention, an ELISA-based assay was developed in order to investigate the biological properties of Fc:ligand constructs, namely their ability to bind to their corresponding receptors. In this assay, the Fc:ligand constructs were initially captured by a murine anti-human IgG monoclonal antibody. In a second step, the soluble receptors were fused to the oligomerizing domain of the cartilage oligomeric matrix protein (COMP) (see DE 19963859 and DE 10122140, the entire content of which is in each case hereby incorporated into the present disclosure), and a flag sequence was added. Receptors possessing bound ligands were identified by means of their respective flag tags (see FIG. 5). By means of using this modified ELISA assay approach, it was shown that the Fc:ligand constructs according to the invention did in fact bind to their respective native receptors, that is they do not lose their binding ability as a result of the construct structure, and the binding also takes place with a high degree of selectivity.

It was furthermore demonstrated, according to the invention, that the Fc-ligand constructs according to the invention are also able to bind to surface-expressed, endogenous receptors. It was demonstrated experimentally that, while Fc:BAFF constructs according to the invention label BAFF-R-positive BJAB cell lines in a dose-dependent manner, they do not label the BAFF-R-negative Jurkat cell line (see FIG. 6A). In addition, it was shown that Fc:BAFF is able to specifically immunoprecipitate the endogenous BAFF receptor in BJAB cells (see FIG. 6B).

In addition, the cytotoxicity of Fc:FasL on a FasL-sensitive Jurkat cell line was investigated. Fc:FasL was found to be highly cytotoxic on Jurkat cells, with an $Ic_{50}$ of 1 ng/ml (see FIG. 7). Furthermore, it was found, in accordance with the invention, that there were no significant differences, in regard to the specific activity, between the complete preparation of Fc:FasL according to the invention and the dimeric form of Fc:FasL (6 ch) which was isolated in the 440 kDa peak and/or the oligomeric form of Fc:FasL (12 ch) which was identified in the 850 kDa peak. These results demonstrate that dimeric FasL (6 ch) is already a fully active molecule and that larger complexes do not increase the activity in this regard any further.

4$^{th}$ Implementation Example

Biological Activity of Fc:Ligand Constructs According to the Invention In Vivo The fusion proteins Fc:FasL and Fc:EDA were tested in vivo.

Injecting Fc:FasL into mice showed that this fusion protein exhibited cytotoxicity in vivo.

Fusion construct Fc:EDA: EDA is a member of the TNF ligand family which is physiologically responsible for the development and function, and also, in particular, for the morphogenesis, of ectodermal structures, very particularly for sweat glands, hair and teeth as epithelial structures of the ectoderm. Conversely, it is known that malfunction of EDA causes the (XL)HED syndrome in humans while, in mice, malfunction of EDA leads to what is termed the Tabby phenotype, which is essentially characterized by (i) the coat having an abnormal structure, (ii) absence of the different native hair types, (iii) loss of hair on the tail and in the region of the skin behind the ears, (iv) absence of sweat glands in the paws, (v) abnormal tooth formation and tooth eruption (vi) characteristic distortion at the tip of the tail, (vii) absence of Moebius glands (glands in the eyelid which secrete a thin film of fat for protecting the cornea from drying out; the cornea therefore becomes keratinized) and other glands, (viii) reduction in the size of the eye aperture, and (ix) lower increase in weight in young mice.

In accordance with the invention, 400 μg of Fc:EDA1 were injected in utero into female tabby mice on the 11$^{th}$, 13$^{th}$ and 15$^{th}$ days of pregnancy. This fusion protein was extremely well tolerated and no contraindicating effects were observed in the treated mice. While the Fc:EDA1 treatment did not give rise to any recognizable effects in the treated female adult mice themselves, a definite and powerful reversion of the tabby phenotype was observed in the progeny of the treated pregnant mother animals. This phenotype reversion was evident on the 10$^{th}$ day after birth. The size of the progeny of the tabby mice which were treated during pregnancy was substantially greater than those of the control mice while their coats were smooth, black and shiny (see FIGS. 8A to 9A). In contrast to the situation in the tabby mice, the retroauricular region in the treated tabby mice was also found to be hairy and these latter mice have normal, unbent hairy tails possessing a large number of hair follicles and the corresponding sebaceous glands, which it was possible to observe on the skin in the tail region (see FIG. 8B).

In addition, it was possible to discern eccrine sweat glands, which were indistinguishable from the corresponding wild-type sweat glands, in tissue sections of the paws of treated, but not untreated, tabby mice (see FIG. 8B). In the tabby mice which were treated in the embryonic stage in utero, these sweat glands were also still functional in adulthood. A sweat test was carried out for the purpose of determining the functional ability of the glands: for this, a 3.5% (w/v) solution of $I_2$ in ethanol was rubbed into the paws of the investigated animals and then left to dry. After that, a 50% (w/v) solution of starch in mineral oil was applied to the paws. A photograph was then taken after applying moderate heat using a hairdryer (5 s). Animals were sacrificed and tissue sections of the eyelid and the cornea stained with hemotoxylin and eosin were prepared.

The reverted phenotype was stable, as it was possible to confirm by analyzing treated tabby mice in the adult state (see FIG. 9A to FIG. 9D). These mice were significantly larger than tabby mice and their coats possess, in particular, the longer, monotrichous, wild-type hair variety which is completely lacking in the tabby mice. These treated mice had no bald patches in the retroauricular region and the paws possessed eccrine sweat glands which were indistinguishable from those of the wild type. In addition to this, these sweat glands were functional (FIG. 9A), as demonstrated in the above-described sweat test. Following treatment, the Moebius glands, which are always missing in tabby mice, were once again present and enabled normal, nonkeratinized cornea to be formed, with this providing proof of the functional competence of the Moebius glands (FIG. 9C). The teeth of treated tabby mice were of a normal size and exhibited a wild-type pattern of tooth cusps. The third molar is small in wild-type mice and absent in tabby mice. This third molar was also missing in treated tabby mice. The results demonstrate that, when administered to pregnant mice, Fc:EDA1 according to the invention, as shown in FIG. 1D, is able to gain access to the developing embryo, via placental Fc receptors, and to trigger induction, at EDA receptors, of the formation of native epithelial structures. In this regard, the dimerization of EDA1 (6 ch) is very probably of central importance since genetic and biochemical investigations indicate that the oligomerization of EDA is essential for its activity. It was furthermore demonstrated, in accordance with the invention, that, following the induction and establishment of epithelial structures in the developing embryo, functional EDA no longer needs to be supplied to the adult animal in order to maintain the reverted native phenotype.

5$^{th}$ Implementation Example

In this example, an investigation was carried out to determine the extent to which a late, postnatal administration of Fc:EDA1 according to the invention was able to relieve the symptoms of the tabby phenotype in mice. Fc:EDA1 was therefore administered intraperitoneally to the young mice on the 2$^{nd}$ (40 μg), the 4$^{th}$ (40 μg), the 6$^{th}$ (60 μg), the 8$^{th}$ (100 μg) and 10$^{th}$ (100 μg) days (or, in an alternative experimental set-up: on the 5$^{th}$ (40 μg), on the 7$^{th}$ (60 μg), on the 9$^{th}$ (60 μg), on the 11$^{th}$ and on the 13$^{th}$ (in each case 100 μg) days after birth); a control group of tabby mice was left untreated.

The appropriately treated mice, or mice from the control group, were examined for the following phenotypic features (i) "bent" tail, (ii) formation of hair on the tail and/or behind the ear region, and (iii) eye shape. In addition, a sweat test was carried out in adult mice and tissue sections from the paw and tail skin regions of 25-day-old mice were examined.

In the case of this postnatal administration of Fc:EDA1 as well, it was possible to bring about a large number of symptoms of the tabby phenotype, in particular the restoration of the tail hair and sweat glands. It was possible to observe the tail hair on the 15th day (already on the 2nd day after birth) in the case of the Fc:EDA1-treated tabby mice (instead of on the 7th to 9th day after birth in the case of WT mice). In the case of the mice which were treated for the first time on the 5th day after birth, hair formation was observed on the 18th day. In the case of the treated tabby mice, the hair is initially formed on the ventral side of the tail. In all the treated tabby mice, irrespective of the time at which the treatment began, the structure and density of the tail hair did not differ from that of the tail hair in WT animals. This belated hair formation in the treated tabby mice can be readily explained by the later induction of the formation of hair follicles, as triggered by the Fc:EDA1 according to the invention which was administered. The experimental approaches described in this implementation example were unable to relieve the lack of hair (alopecia) behind the ears.

While the postnatal therapy was unable to completely revert the bent tail form, it was able to do so to a large extent. While the eye aperture of the treated tabby mice was significantly enlarged as compared with that of the untreated tabby mice, it was not precisely as large as in the WT mouse (FIG. 10A). Functional sweat glands developed in the paws of the treated tabby mice, as was demonstrated in tissue section taken from 25-day-old treated tabby mice (FIG. 10B). Sweat tests carried out in adult treated tabby animals demonstrated the functional ability of the sweat glands which developed in adult animals as a result of the treatment.

In summary, it can be stated that the experiments according to the invention are able to illicit an almost complete reversion of a phenotype which is to be genetically attributed to the absence of the TNF ligand EDA. The best curative successes were observed in the case of the tabby mice which were already treated with recombinant fusion protein according to the invention in utero. However, postnatal administration of fusion proteins according to the invention, e.g. Fc:EDA1, to genotypically affected animals also results in considerable curative success, i.e. in a (partial) reversion of the phenotype, in particular in the development of sweat glands (especially in the paws) and tail hair, and in an enlargement of the eye aperture.

What is claimed:

1. A pharmaceutical composition for treating a symptom of X-coupled hypohydrotic ectodermal dysplasia in a patient diagnosed with or suspected of having X-coupled hypohydrotic ectodermal dysplasia, wherein the symptom of X-coupled hypohydrotic ectodermal dysplasia is selected from the group consisting of: missing teeth, abnormal development of teeth, dysfunction or lack of sweat glands, lack of Moebius glands, lack of sebaceous glands, and alopecia and wherein the patient is in utero and the pharmaceutical composition is administered to the patient's mother, said pharmaceutical composition comprising a recombinant fusion protein and at least one pharmaceutically acceptable carrier material, wherein said recombinant fusion protein comprises (a) an Fc fragment of an immunoglobulin consisting of amino acids 18-243 of SEQ ID NO: 6, and (b) an extracellular moiety of Ectodysplasin (EDA1) comprising amino acids 266-412 of SEQ ID NO: 6.

2. The pharmaceutical composition of claim 1, wherein the pharmaceutical acceptable carrier is an aqueous carrier.

3. The pharmaceutical composition of claim 2, wherein the aqueous carrier is water for injection (WFI) or water buffered with phosphate, citrate or acetate.

4. The pharmaceutical composition of claim 3, wherein the pH of the pharmaceutical composition is around 5.0 to around 8.0.

5. The pharmaceutical composition of claim 4, wherein the pH of the pharmaceutical composition is around 6.0 to 7.0.

6. The pharmaceutical composition of claim 1, wherein the pharmaceutical composition further comprises human serum albumin, polysorbate 80, sugars, or amino acids.

7. The pharmaceutical composition of claim 1, wherein the pharmaceutical composition is injectable.

8. The pharmaceutical composition of claim 7, wherein the pharmaceutical composition further comprises at least one injectable pharmaceutical carrier selected from sterilized water, physiological sodium chloride, vegetable oils, mineral oils, higher alcohols, higher fatty acids, and non-toxic organic solvents.

9. The pharmaceutical composition of claim 8, wherein the pharmaceutical composition further comprises fillers, binders, stabilizers, preservatives, antiadsorbants, surface-active substances, dyes, flavorings, emulsifiers, buffering agents, isotonic agents, antioxidants, or analgesics.

10. The pharmaceutical composition of claim 1, wherein the pharmaceutical composition further comprises sodium alginate, polyethylene glycol, or titanium dioxide.

11. The pharmaceutical composition of claim 1, wherein the recombinant fusion protein concentration is in a range of from about 0.001 to about 10 mg/ml.

12. The pharmaceutical composition of claim 11, wherein the recombinant fusion protein concentration is in a range of from about 0.5 to about 5 mg/ml.

13. The pharmaceutical composition of claim 1, wherein the pharmaceutical composition is isotonic.

14. The pharmaceutical composition of claim 13, wherein the pharmaceutical composition comprises salt constituents.

15. The pharmaceutical composition of claim 14, wherein the salt constituents are sodium chloride or potassium chloride.

* * * * *